United States Patent
Suda et al.

(10) Patent No.: US 10,242,157 B1
(45) Date of Patent: Mar. 26, 2019

(54) SYSTEM AND METHOD FOR PROVIDING DENTAL TREATMENT RECOMMENDATIONS

(71) Applicant: Smile Brands, Inc., Irvine, CA (US)

(72) Inventors: George Joseph Suda, Fullerton, CA (US); Dan Chi Ta, Rancho Cucamonga, CA (US); Phong Trung Pham, Placentia, CA (US); Marlin H. Clark, Aliso Viejo, CA (US)

(73) Assignee: Smile Brands, Inc., Irvine, CA (US)

( * ) Notice: Subject to any disclaimer, the term of this patent is extended or adjusted under 35 U.S.C. 154(b) by 371 days.

(21) Appl. No.: 15/200,795

(22) Filed: Jul. 1, 2016

Related U.S. Application Data

(63) Continuation of application No. 14/210,093, filed on Mar. 13, 2014.

(60) Provisional application No. 61/785,592, filed on Mar. 14, 2013.

(51) Int. Cl.
*G06F 19/00* (2018.01)
*A61C 7/00* (2006.01)
*G16H 10/60* (2018.01)

(52) U.S. Cl.
CPC ............ *G06F 19/325* (2013.01); *A61C 7/002* (2013.01); *G16H 10/60* (2018.01)

(58) Field of Classification Search
None
See application file for complete search history.

(56) References Cited

U.S. PATENT DOCUMENTS

| 8,160,899 B2* | 4/2012 | Rhodes | G06F 19/322 705/2 |
| 8,407,066 B2 | 3/2013 | Gentry et al. | |
| 8,412,537 B1 | 4/2013 | Fenton et al. | |
| 8,548,937 B2* | 10/2013 | Saigal | G06N 5/048 706/52 |
| 2002/0042725 A1* | 4/2002 | Mayaud | G06F 19/3456 705/2 |
| 2004/0236608 A1* | 11/2004 | Ruggio | G06Q 10/10 705/2 |

(Continued)

OTHER PUBLICATIONS

AdvantEdge Specialty Billing Software in 2 pages.

(Continued)

*Primary Examiner* — Michael Tomaszewski
(74) *Attorney, Agent, or Firm* — Knobbe, Martens, Olson & Bear, LLP

(57) ABSTRACT

Systems and methods described herein can provide clinicians with a dental office management service that can programmatically provide treatment recommendations and streamline the patient record building process. These systems and methods can enable clinicians to select from a short list of recommended treatments based on the existing condition and pathology of a tooth, for example, as the dentist is giving instructions and treatment recommendations. A list of recommended treatments for a patient may be automatically compiled based on the treatment recommendations selected by the clinician as the dentist was examining the patient's teeth one by one. Further, systems and methods described herein can enable clinicians to take notes and thereby build a patient record efficiently using one or more completed treatment templates.

20 Claims, 49 Drawing Sheets

(56) References Cited

U.S. PATENT DOCUMENTS

| | | | |
|---|---|---|---|
| 2005/0027172 A1* | 2/2005 | Benavides | G06Q 50/22 600/300 |
| 2006/0149140 A1 | 7/2006 | Eldridge | |
| 2007/0129967 A1 | 6/2007 | Thompson et al. | |
| 2007/0226005 A1* | 9/2007 | Smith | G06F 19/324 705/2 |
| 2007/0239488 A1* | 10/2007 | DeRosso | G06F 19/321 705/3 |
| 2008/0033754 A1* | 2/2008 | Smith | G06F 19/324 705/2 |
| 2008/0140371 A1* | 6/2008 | Warner | A61B 5/0002 703/11 |
| 2008/0189139 A1* | 8/2008 | Sachdeva | G06F 19/3481 705/3 |
| 2009/0171696 A1 | 7/2009 | Allard et al. | |
| 2010/0036682 A1* | 2/2010 | Trosien | G06Q 10/10 705/3 |
| 2010/0070297 A1 | 3/2010 | Kharraz Tavakol et al. | |
| 2011/0130635 A1 | 6/2011 | Ross | |
| 2013/0166318 A1 | 6/2013 | Lathem et al. | |

OTHER PUBLICATIONS

CareCloud—Key Features in 2 pages.
Curve Dental print out of webpage in 5 pages.
Daisy Dental Software webpage print out in 3 pages.
Dentsio iPad app—Dental Practice Management Software. <http://www.dentsio.com/app.html> Printed Feb. 28, 2014 in 2 pages.
MOGO, Inc. brochure in 5 pages.
ProDental Billing—Frequently Asked Questions in 3 pages.

* cited by examiner

SYSTEM AND METHOD FOR PROVIDING DENTAL TREATMENT RECOMMENDATIONS

CROSS-REFERENCE TO RELATED APPLICATIONS

This application is a continuation of U.S. patent application Ser. No. 14/210,093, filed Mar. 13, 2014, titled "SYSTEM AND METHOD FOR PROVIDING DENTAL TREATMENT RECOMMENDATIONS," which claims the benefit of the filing date of U.S. Provisional Patent Application No. 61/785,592, filed Mar. 14, 2013, titled "SCALABLE DENTAL OFFICE MANAGEMENT SYSTEM," all of which are hereby incorporated by reference in their entireties, including the appendices filed therewith.

BACKGROUND

With the advent of computers, more and more tasks are being performed electronically in an office environment, including a dental office. There are many software programs that aid dental professionals with various tasks performed in the dental office, such as scheduling appointments, maintaining patient files, and submitting insurance claims. Such software programs can save time for the dental professionals by either automatically performing the tasks or greatly simplifying the steps that needed to be taken in order to perform those tasks. For example, by maintaining patient files electronically, the dental professionals can browse or search the files without going through physical files one by one, and they can easily create, expand, delete, or rearrange the files, thereby saving both time and energy.

SUMMARY

Systems and methods described herein can provide clinicians with a dental office management service that can programmatically provide treatment recommendations and streamline the patient record building process. These systems and methods can enable clinicians to select from a short list of recommended treatments based on the existing condition and pathology of a tooth, for example, as the dentist is giving instructions and treatment recommendations. A list of recommended treatments for a patient may be automatically compiled based on the treatment recommendations selected by the clinician as the dentist was examining the patient's teeth one by one. Further, systems and methods described herein can enable clinicians to take notes and thereby build a patient record efficiently using one or more completed treatment templates.

For purposes of summarizing the disclosure, certain aspects, advantages and novel features of several embodiments are described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

BRIEF DESCRIPTION OF THE DRAWINGS

Throughout the drawings, reference numbers are re-used to indicate correspondence between referenced elements. The drawings are provided to illustrate embodiments described herein and not to limit the scope thereof.

DETAILED DESCRIPTION

I. Introduction

Figure 1:
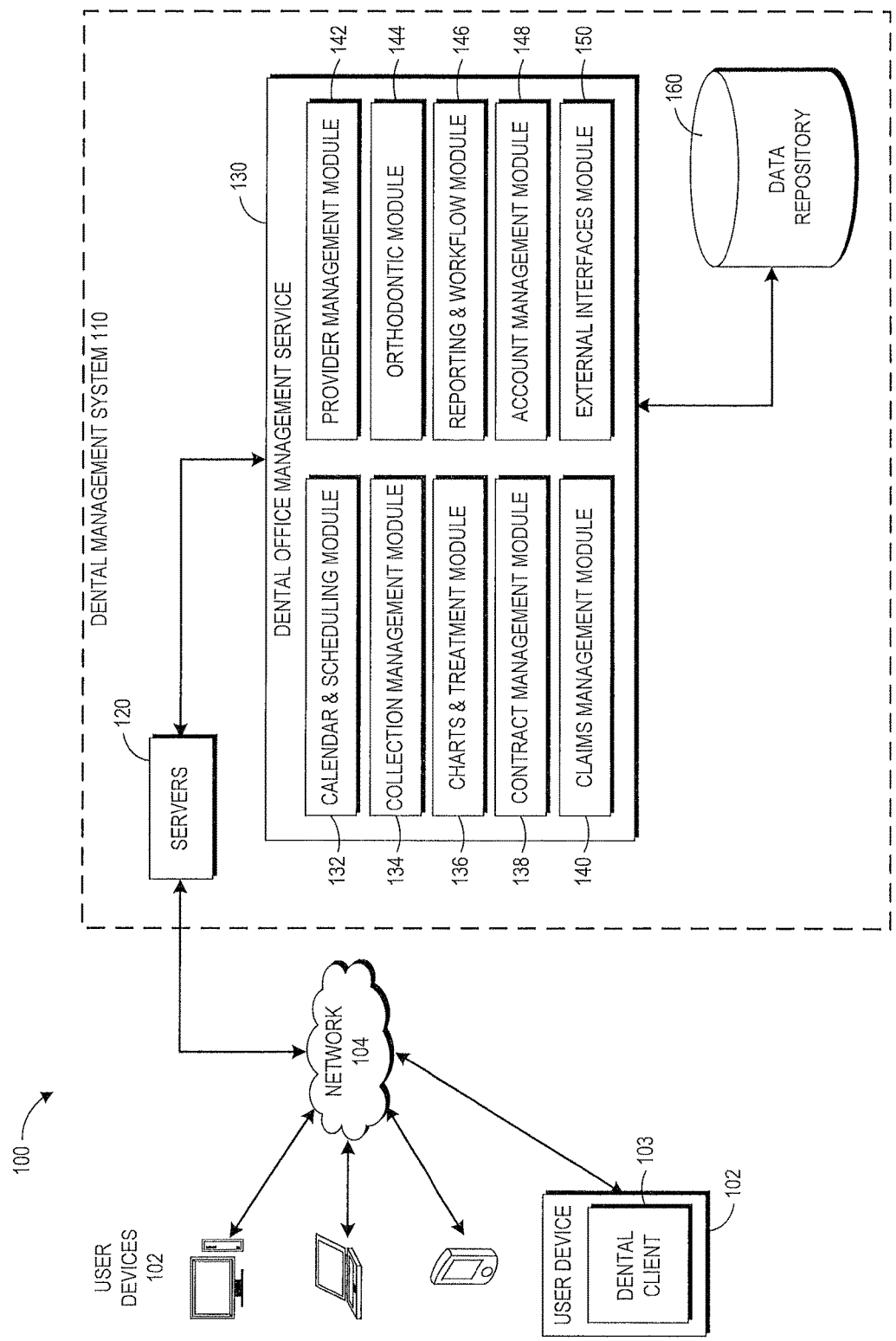
FIG. 1 depicts an embodiment of a computing environment that provides users with access to an dental management system that provides various dental office management services to a clinician.

Despite the convenience provided by existing dental practice management software programs, some tasks performed by clinicians via such programs are still time-consuming and inefficient. For example, when a patient is being examined by a dentist, the dentist may give various instructions and treatment recommendations for his or her dental assistant to record and transfer onto the dental software. The dental assistant may take hand-written notes on the instructions and treatment recommendations given by the dentist, go to his or her computer, and enter the dentist's instructions and treatment recommendations. The dental assistant may be expected to compile a list of recommended treatments so that he or she can review them with the patient and answer any questions.

Due to human error, it is easy for the dental assistant to miss important details in compiling treatments for a patient. As a result, patient care outcomes can be adversely impacted should one of those treatments not be later performed as originally prescribed by the clinician. Further, an incomplete or incorrect record of treatments can result in difficulties in obtaining insurance payments for completed treatments. Insurers typically require detailed explanatory notes, complete with approved American Dental Association (ADA) codes, in order to process payment. If a patient's record is incomplete, whether missing an ADA code (or having an improper code) for a treatment or missing details of a treatment, an insurer may legitimately refuse payment. The current system of compiling hand-written notes by dental assistants is therefore inefficient, prone to errors, and potentially costly in both financial terms and patient care terms. Thus, a more efficient method for compiling a list of recommended treatments is desired to improve patient outcomes and improve insurance compliance and collections.

Accordingly, embodiments of systems and methods described herein provide clinicians with a dental office management service that can programmatically provide treatment recommendations and streamline the patient record building process. These systems and methods can enable clinicians to select from a short list of recommended treatments based on the existing condition and pathology of a tooth, for example, as the dentist is giving instructions and treatment recommendations. A list of recommended treatments for a patient may be automatically compiled based on the treatment recommendations selected by the clinician as the dentist was examining the patient's teeth one by one. Further, systems and methods described herein can enable clinicians to take notes and thereby build a patient record efficiently using one or more completed treatment templates.

For purposes of illustration, the processes disclosed herein are described primarily in the context of an dental management system that presents users with various functionalities for dental office management via one or more user interfaces. The dental management system can be implemented as a network resource or application, which may be a website with one or more web pages, a mobile application, a combination of the same, or the like. As will be apparent, the disclosed processes can also be used in other types of systems.

Although described herein primarily with respect to dentists, the techniques described herein may also be used in other contexts, such as with doctors other than dental doctors. For example, family physicians or other physicians may wish to use the techniques, processes, systems, and a combination and/or a version thereof to manage their practices.

In the present disclosure, the term "clinician," in addition to having its ordinary meaning, may include a dentist, a dental doctor, a dental hygienist, a dental assistant, a dental professional, an orthodontist, an endodontist, a periodontist, a prosthodontist, any other type of dental specialist, and the like. Further, many aspects of the systems described herein that may be used by a clinician may also be used by dental office staff. Thus, some examples of users that can use the dental management system described herein can include clinicians and dental office staff.

II. Dental Management System Overview

Turning to FIG. 1, an example computing environment 100 is shown, in which access to an dental management system 110 is provided to user devices 102 over a network 104. The dental management system 110 can represent a hardware platform or software platform (that is implemented using computer hardware) for which users can access the various functionalities of the dental management system 110.

When users of the user devices 102 connect to the dental management system 110 over the network 104, the dental management system 110 can provide the users with a variety of functionalities that may be used in a dental practice. For example, such functionalities may include calendaring and scheduling, collections management, charts and treatment, contract management, claims management, provider management, orthodontic management, reporting and workflow management, account management, external interfaces, and the like. Certain of these functionalities are described below in more detail. For example, the dental management system 110 may provide one or more user interfaces that enable a user to enter treatment and pathology notes for a patient, select from a list of recommended treatments for the patient, and enter post-treatment narratives based on one or more completed treatment templates.

In the embodiment illustrated in FIG. 1, an dental client 103 installed on an example one of the user devices 102 can access the dental management system 110, and the user of the user device 102 can access the various functionalities provided by the dental management system 110 via the dental client 103. The dental client 103 may be a mobile application installed on the user device 102, which may be a tablet, phone (e.g., smartphone), laptop, desktop, or the like. For example, the mobile application can be used by a dental assistant to allow the quick recording of information dictated by the dentist at the time of the patient exam. In other embodiments, the dental client 103 may be a browser or another software program installed on the user device 102. The dental client 103 may provide access to any of the functionalities described herein in connection with the dental management system 110. For example, the dental client 103 may be able to access and display patient restorative and periodontal charts stored by the dental management system 110, allow clinicians to enter treatment and pathology notes, and perform any other task described herein.

By way of illustration, various example user devices 102 connecting to the dental management system 110 are shown, including a desktop computer, laptop, and a mobile phone. In general, the user devices 102 can be any computing device such as a desktop, laptop, mobile phone (or smartphone), tablet, and the like. The user devices 102 can access the dental management system 110 over a network 104. The network 104 may be any wired network, wireless network, or combination thereof. In addition, the network 104 may be a personal area network, local area network, wide area network, over-the-air broadcast network (e.g., for radio or television), cable network, satellite network, cellular telephone network, or combination thereof. Thus, the network 104 can be a local area network (LAN), wide area network (WAN), an intranet, the Internet, or any portion thereof. The network 104 can use protocols and components for, communicating via the Internet or any of the other aforementioned types of networks. Further, the dental management system 110 may be implemented in hardware and/or software and may, for instance, include one or more physical or virtual servers implemented on physical computer hardware configured to execute specific computer executable instructions for performing various features that will be described herein. The one or more servers may be geographically dispersed or geographically co-located, for instance, in one or more data centers.

In the depicted embodiment, the dental management system 110 includes servers 120, which can communicate with the user devices 102 over the network 104 and which can provide access to a dental office management service 130 of the dental management system 110. The dental office management service 130 can be implemented as one or more software components executing in physical computer hardware on the servers 120 or in separate computing devices. Moreover, the processing of the various components of the dental management system 110 can be distributed across multiple machines, networks, or other computing resources. The various components of the dental management system 110 can also be implemented in one or more virtual machines or in a hosted computing environment, such as in a cloud computing platform (e.g., the Amazon Elastic Compute Cloud™ or Microsoft Azure™ platforms), rather than in dedicated servers. Likewise, one or more data repositories shown (e.g., data repository 160) can represent local and/or remote, physical and/or logical data storage, including, for example, storage area networks or other distributed storage systems. In some embodiments, the connections between the components of the dental management system 110 represent possible paths of data flow, rather than actual connections between hardware. Executable code modules that implement various functionalities of the dental management system 110 can be stored in the memories of the servers 120 and/or on other types of non-transitory computer-readable storage media. While some examples of possible connections are shown, any subset of the components shown can communicate with any other subset of components in various implementations.

The dental office management service 130 can provide functionalities that may facilitate and/or simplify one or more tasks that are typically performed in a dentist's office. In the example of FIG. 1, the dental office management service 130 includes a calendar and scheduling module 132, a collection management module 134, a charts and treatment module 136, a contract management module 138, a claims management module 140, a provider management module 142, an orthodontic module 144, a reporting and workflow management module 146, an account management module 148, and an external interfaces module 150. However, the configuration and the components of the dental office management service 130 are not limited to such modules, and in other embodiments, modules that provide other dental office management functionalities may be included in addition to, or in lieu of, those shown in FIG. 1.

The calendar and scheduling module 132 may provide functionalities associated with scheduling patient appointments and managing such appointments for one or more dental professionals using a calendar. The collection management module 134 may provide functionalities associated with collecting fees from the patients.

The charts and treatment module 136 may provide functionalities associated with entering existing tooth conditions and tooth pathology for a patient, maintaining patient history in a chart format, making treatment recommendations based on the existing tooth conditions and tooth pathology entered by a clinician, and providing completed treatment templates for editing by a clinician. The functionalities provided by the charts and treatment module 136 (e.g., providing treatment recommendations and post-treatment narrative recordation) are described in greater detail below with reference to FIGS. 2 and 3.

The contract management module 138 may provide functionalities associated with managing various contracts entered into by the clinicians and/or patients. The claims management module 140 may provide functionalities associated with filing dental insurance claims. The provider management module 142 may provide functionalities associated with managing dental service providers (e.g., dentists). The orthodontic module 144 may provide functionalities associated with performing, recording, and managing orthodontic procedures. The reporting and workflow management module 146 may provide functionalities associated with preparing status reports, managing the workflow among the clinicians, and distributing the workload among the clinicians. The account management module 148 may provide functionalities associated with managing patient and/or clinician accounts. Furthermore, the external interfaces module 150 may provide functionalities associated with interfacing with programs outside the dental office management service 130.

By using one or more of these modules, the dental office management service 130 enable users of the dental management system 110 to perform tasks associated with a dental practice more efficiently and effectively.

Figure 2:
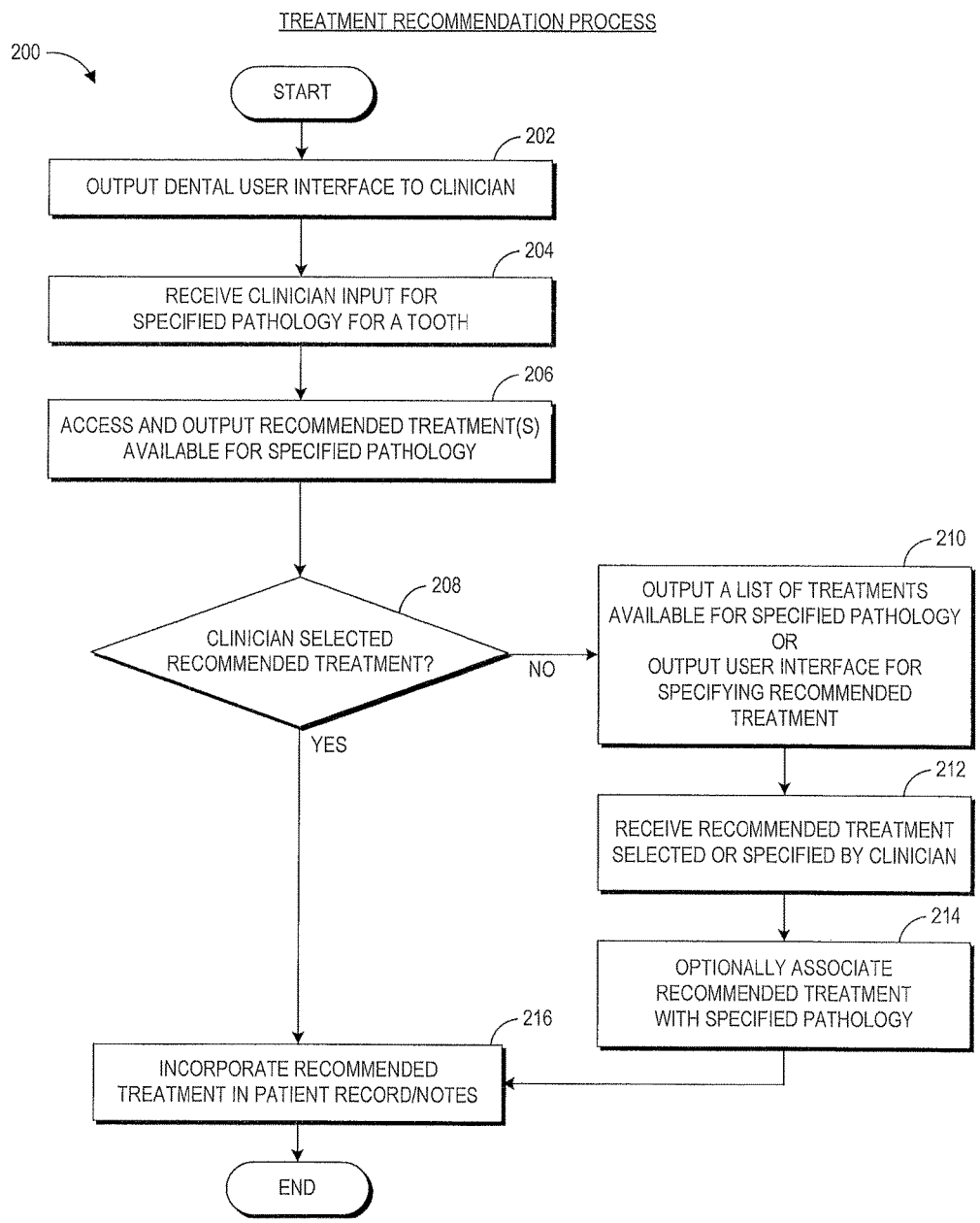
FIG. 2 depicts an embodiment of a treatment recommendation process.
Figure 3:
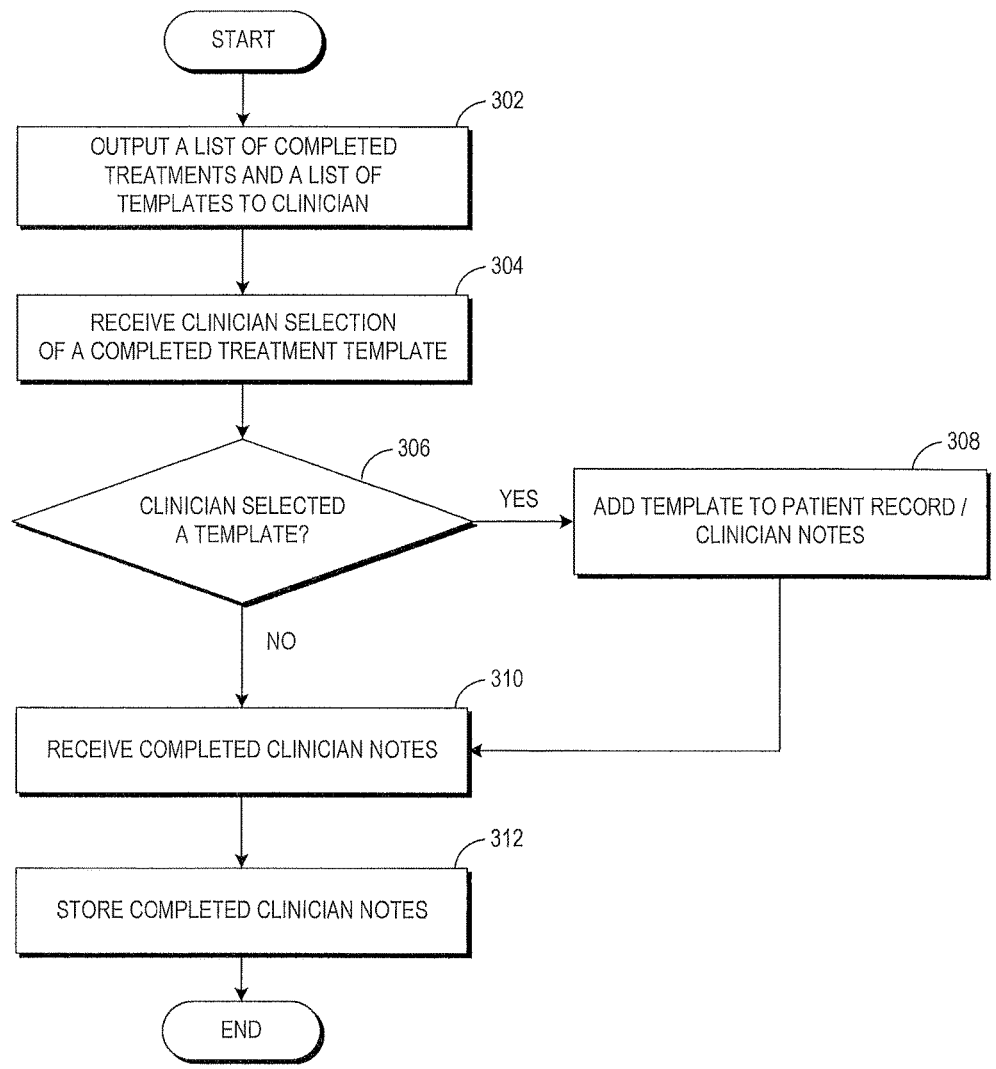
FIG. 3 depicts an embodiment of a post-treatment narrative recordation process.

The data repository 160 of the dental management system 110 can store data that is utilized in connection with one or more of the modules illustrated in FIG. 1. For example, the data repository 160 may store various charts (e.g., periodontal or restorative charts), treatment databases (e.g., recommended treatments stored in association with tooth pathology), completed treatment templates (e.g., preconfigured or user-generated), and the like In addition, the data repository 160 may store patient data including the patient's profile information, treatment history, past and future appointments, insurance information, and the like III. Example Dental Office Management Processes Turning to FIGS. 2 and 3, example processes 200 and 300 that may be implemented by the dental management system 110 are shown. In particular, FIG. 2 depicts a treatment recommendation process 200, and FIG. 3 depicts a post-treatment narrative recordation process 300. For convenience, the processes 200 and 300 will be described in the context of the devices and systems shown in FIG. 1. However, it should be understood that the processes 200 and 300 can be implemented by any computing device and not just the computing devices shown in FIG. 1.

With specific reference to FIG. 2, in the treatment recommendation process 200, a clinician using one of the user devices 102 can input the pathology for one or more teeth of a patient and select from a list of recommended treatments to quickly generate a report or patient record including, for example, the tooth pathology, recommended treatment, any billing or insurance code(s) (e.g., the ADA code) associated with the treatment, cost to the patient, and the like.

Figure 5A:
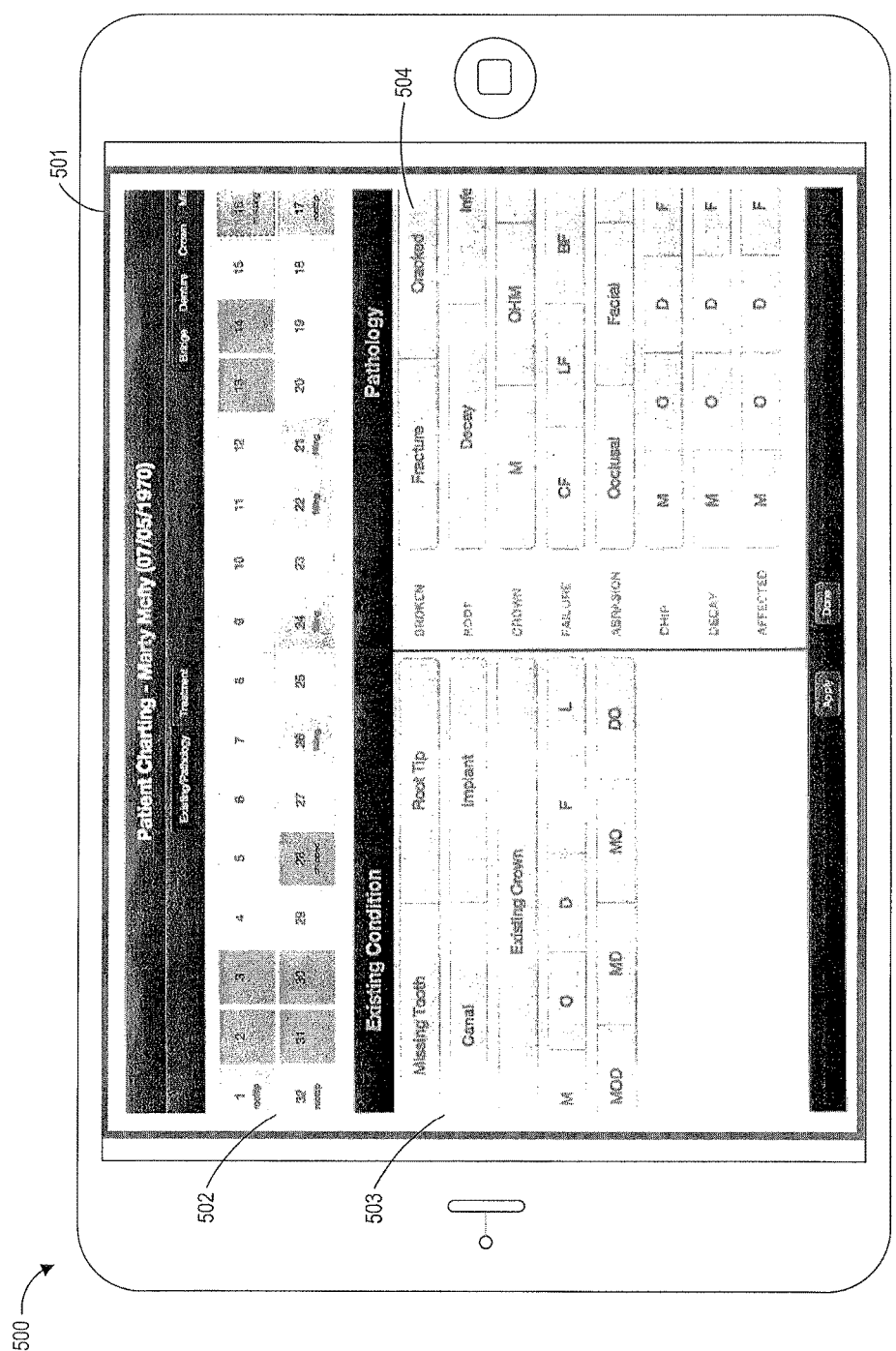
FIGS. 5A-5I depict example user interfaces that provide treatment recommendations.

At block 202 of the process 200, the chart and treatment module 136 outputs a dental user interface to the clinician using the user device 102. The dental user interface can include user interface controls having one or more buttons or the like that the clinician can select to indicate the existing condition and/or pathology of a tooth. For example, as illustrated in FIG. 5A (described in greater detail below), the controls may include a plurality of icons corresponding to the respective teeth of the patient (e.g., icons 514 that are labeled 1 through 32), one or more buttons 503 for specifying the existing condition of the tooth (e.g., missing tooth, root tip, canal, implant, existing crown) and the location/direction of the existing condition (e.g., mesial, occlusal, distal, facial, lingual, and the like), and one or more buttons 504 for specifying the pathology of the tooth (e.g., broken, root, crown failure, abrasion, chip, decay, affected, and the like).

In some embodiments, the chart and treatment module 136 allows the clinician to distinguish between pre-existing conditions and currently observed conditions. For example, a pre-existing condition may include something that happened to a tooth (e.g., cavity) that led to a treatment that has already been completed (e.g., a crown or a filling). A currently observed condition may include something that happened to a tooth (e.g., cavity) for which no treatment has yet been performed. At block 204, the chart and treatment module 136 receives the clinician input for the specified pathology for a tooth. For example, the clinician may activate the one or more icons and buttons (e.g., by touch-activating them in a case that the user device 102 includes a touch-sensitive display) to specify the tooth and the existing condition and pathology for the tooth. Once the chart and treatment module 136 receives the specified pathology for the tooth, at block 206, the chart and treatment module 136 can access and output corresponding recommended treatments available for the specified pathology. The chart and treatment module 136 may access the data repository 160 to determine a list of recommended treatments for the specified pathology. In one embodiment, the existing condition(s) of the tooth are taken into account for generating the list of recommended treatments.

In one embodiment, the list of recommended treatments is generated based on the location of the tooth, the surface of the tooth, tooth pathology specified by the clinician, and/or existing conditions specified by the clinician. One or more of such factors may help condense the database of available treatments down to a shorter list. Thus, rather than having to type out the treatment recommended by the dentist or look through the entire database of available treatments to select the treatment recommended by the dentist, the dental assistant can choose from a shorter list output by the chart and treatment module 136. The data repository 160 may comprise one or more databases including available treatments.

In one embodiment, more than one treatment is grouped together such that if one treatment in the group is selected by the clinician, other treatments in the same group are also automatically selected and stored in the patient record. For example, the chart and treatment module 136 may know that for a tooth with an infected root, a root canal can be recommended, but also a crown and a build-up. If a root canal is selected for the tooth by the clinician from the dental user interface, a crown and a build-up may also be automatically selected. In another embodiment, if one treatment in the group is selected, the chart and treatment module 136 seeks approval (e.g., via a pop-up window) to add other treatments in the same group. In yet another embodiment, if one treatment in the group is selected, before the list of treatments is finalized to be shown to the patient, the chart and treatment module 136 may alert the clinician of any missing treatments not selected, based on the existing selections by the clinician, and optionally suggest adding the missing treatments. Further, in certain embodiments, the chart and treatment module 136 may suggest one or more additional treatments based on the treatment selected by the clinician. As an example, if a root canal is selected, the chart and treatment module 136 may also suggest tooth removal as a possible treatment. If tooth removal is selected by the clinician, the chart and treatment module 136 can further suggest a dental implant or bridge as a treatment option. Thus, the chart and treatment module 136 may make treatment recommendations according to a decision tree stored in memory or data storage, where the decision tree includes logic that dictates successive treatment recommendations based on input pathology, tooth, surface, and/or previous selected treatment.

In one embodiment, any information entered into the dental management system 110 is shared among some or all the processes and modules shown in FIG. 1, such that they are performed in a consistent manner across the dental management system 110. For example, if one clinician has previously indicated in the periodontal chart of a patient that the third molar was missing, another clinician examining the same patient would not be able to perform or recommend any treatments on the third molar.

In one embodiment, the chart and treatment module 136 maintains a record of treatments that were previously recommended to the patient (e.g., a treatment history), and adjusts the list of recommended treatments based on the record of treatments. For example, if the record indicates that the doctor recommended an inlay (e.g., an intermediate procedure to crowning the tooth) 6 months ago but the patient elected to forgo the treatment, the chart and treatment module 136 may now also include the full crown in the list of recommended treatments, since the condition of the tooth may have gotten worse.

At block 208, the chart and treatment module 136 determines whether the clinician selects a recommended treatment from the list of recommended treatments. If the chart and treatment module 136 determines that the clinician has selected a recommended treatment from the list of recommended treatments (e.g., YES at block 208), the chart and treatment module 136 incorporates or stores the recommended treatment, for example, in a record of patient notes for the patient. For example, the chart and treatment module 136 may determine that the clinician has selected a recommended treatment from the list of recommended treatments if the chart and treatment module 136 receives input from the clinician selecting one of the recommended treatments from the list of recommended treatments output by the chart and treatment module 136.

Alternatively, the chart and treatment module 136 may determine that the clinician does not select a recommended treatment from the list of recommended treatments. Instead, the chart and treatment module 136 may receive input from the clinician activating a button for choosing or specifying a recommended treatment that is not listed in the list of recommended treatments output by the chart and treatment module 136. An example of such a button is illustrated in FIG. 5H as a button 582. If the chart and treatment module 136 determines that the clinician does not select a recommended treatment from the list of recommended treatments (e.g., NO at block 208), the chart and treatment module 136 outputs, at block 210, a list of treatments available for the tooth pathology specified by the clinician. For example, the list may be a longer or complete list of treatments available in the database (e.g., the data repository 160 shown in FIG. 1). An example of a list of treatments is illustrated in FIG. 5I, which is further described below. In another embodiment, instead of outputting the list of treatments, the chart and treatment module 136 may output a separate user interface (or update the current user interface) for specifying a new treatment to the clinician. The user interface may also allow the clinician to enter text specifying the ADA code, cost of treatment, or other information to be associated with the new treatment.

Figure 6A:
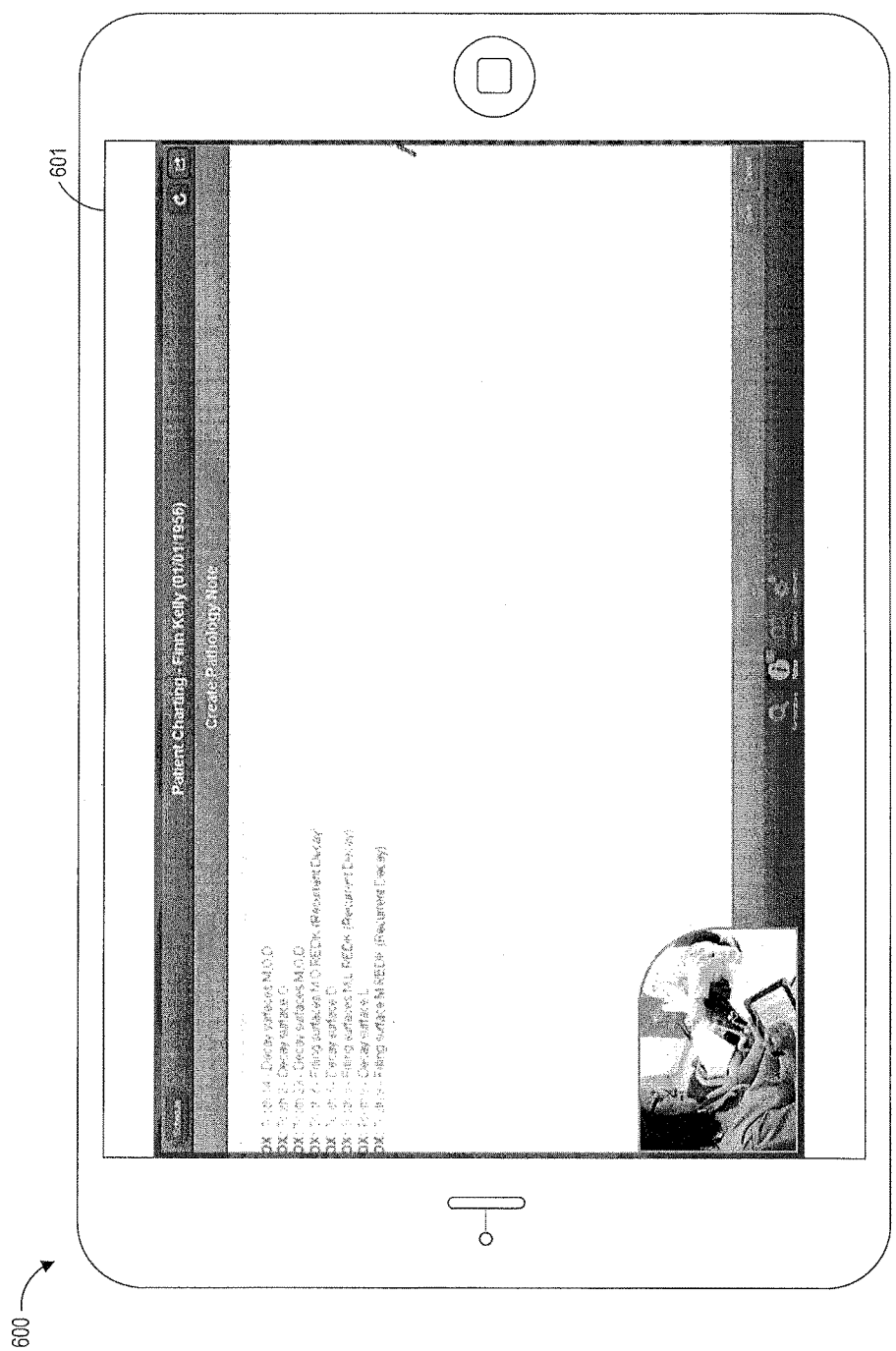
FIGS. 6A-6C depict example user interfaces that provide functionality for inputting pathology/clinician notes.
Figure 6B:
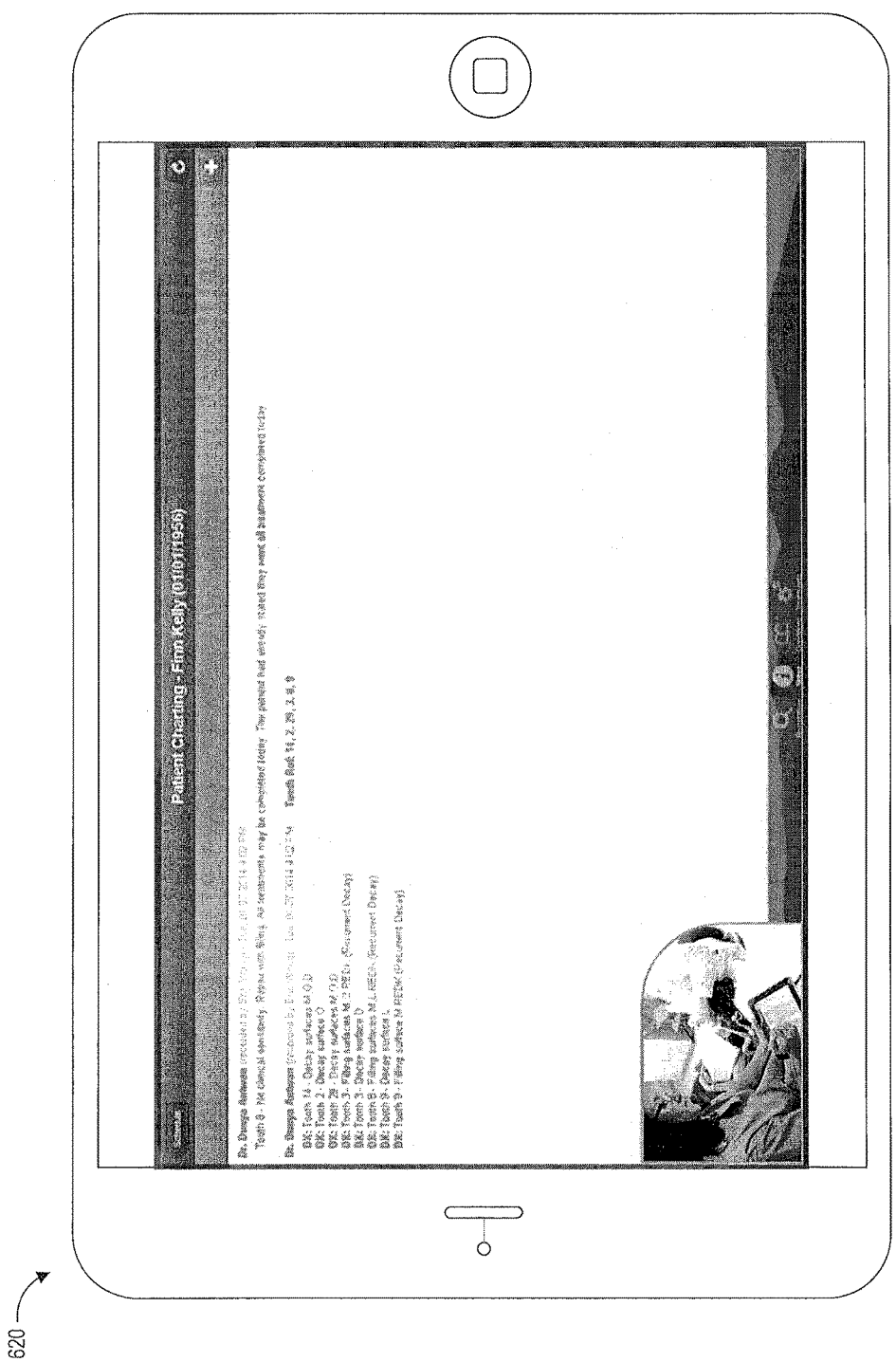
Figure 6C:
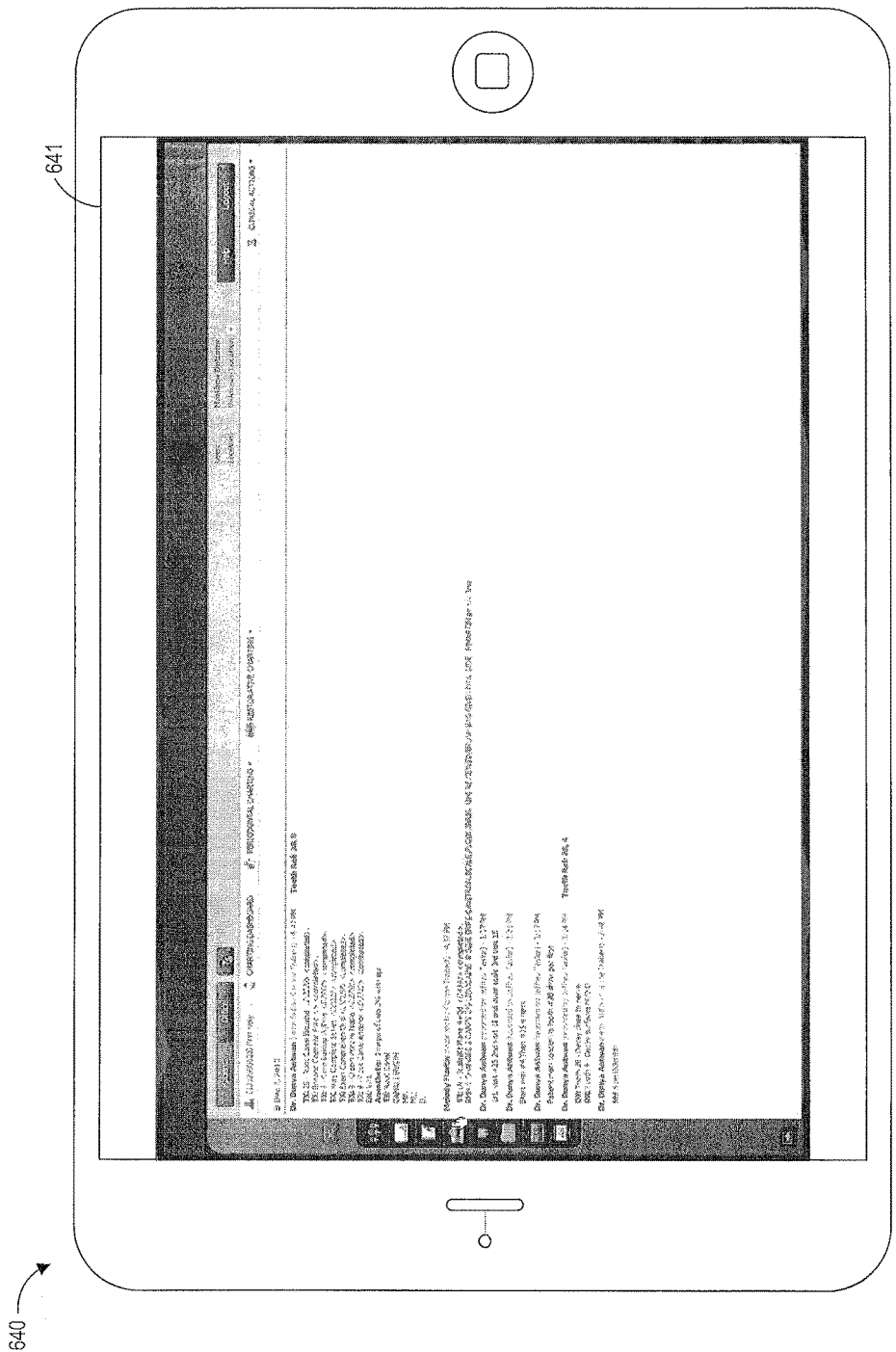

At block 212, the chart and treatment module 136 receives a recommended treatment either selected by the clinician from the list of treatments or specified by the clinician via the user interface output by the chart and treatment module 136. At block 214, the chart and treatment module 136 optionally associates the recommended treatment with the tooth pathology specified by the clinician, such that the recommended treatment may be included in the initial list of recommended treatments (e.g., output by the chart and treatment module 136 at block 206). The recommended treatment received by the chart and treatment module 136 is incorporated or stored in the patient notes at block 216. Examples of the patient notes are shown in FIGS. 6A-6C, which are further described below. The incorporated or stored list of treatments may be presented to the patient for approval, and the approval status (e.g., whether or not the patient elected to proceed with the recommended treatment) of the treatments may also be incorporated or stored along with the list of recommended treatments (e.g., one or more treatments called out by the dentist during the examination and selected by the dental assistant).

Turning to FIG. 3, a post-treatment narrative recordation process 300 is shown. The clinician may wish to add notes to a patient record regarding a completed treatment. These notes can facilitate building a record that an insurer would find acceptable for reimbursing patient treatments. Further, these notes can provide clinicians with a detailed patient record that enables clinicians to more accurately recall treatment details to further improve patient outcomes at later patient visits.

The post-treatment narrative recordation process 300 can allow the clinician to view a list of completed treatments and add details regarding one or more of the completed treatments using available templates provided by the chart and treatment module 136 or templates created by the clinician. For example, a template may be a block of text or a form that includes details of a completed treatment (e.g., anesthetic used, irrigant used, canal length, hygiene, restorative existing conditions and treatments, next visit, and the like). The template may also include fields or blanks to be filled in by the clinician. Such fields may be have default values that the clinician can modify after adding the template to the clinician notes. The chart and treatment module 136 can also enable clinicians to create their own templates, which they can use subsequently like the default templates provided by the chart and treatment module 136. Different dental practitioners may have different styles and preferences (e.g., particular drug mixtures used in a certain treatment), and the templates can be customized to suit their individual needs and facilitate the record building process. By enabling the clinician to use templates, the post-treatment narrative recordation process 300 allows the clinician to quickly add notes related to a treatment upon completing the treatment.

At block 302 of the process 300, the chart and treatment module 136 outputs to the clinician a list of completed treatments along with a list of templates. At block 304, the chart and treatment module 136 receives a completed treatment selected by the clinician. After the clinician has selected a completed treatment, the clinician may be provided a text box in which he or she can type in notes related to the selected treatment. The text box may display any existing notes associated with the completed treatment. The list of templates output to the clinician may include any standard templates or customized templates created by the clinician. The templates may be stored in the data repository 160.

Figure 7A:
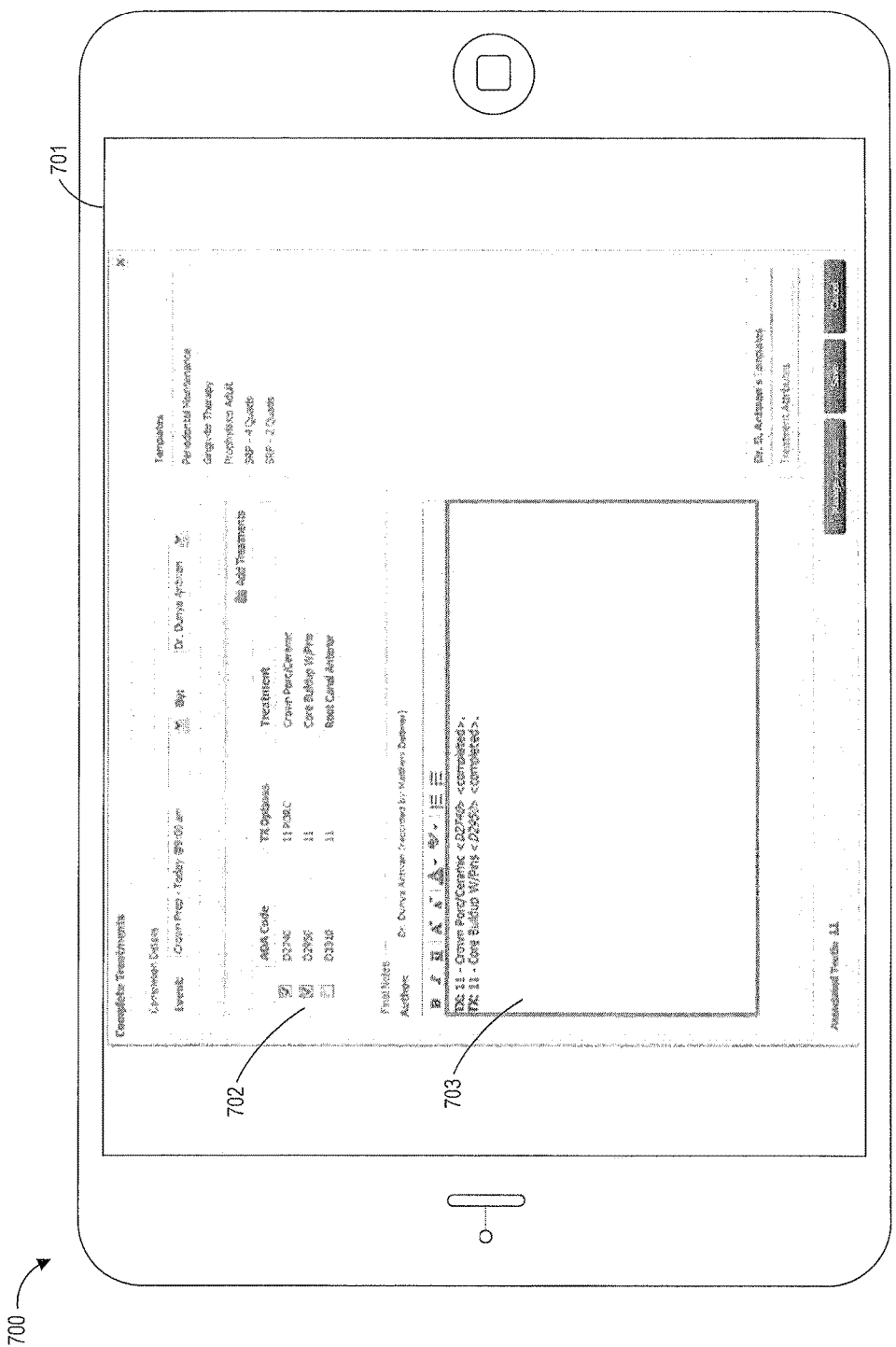
FIGS. 7A and 7B depict example user interfaces that provide post-treatment narrative recordation features.
Figure 7B:
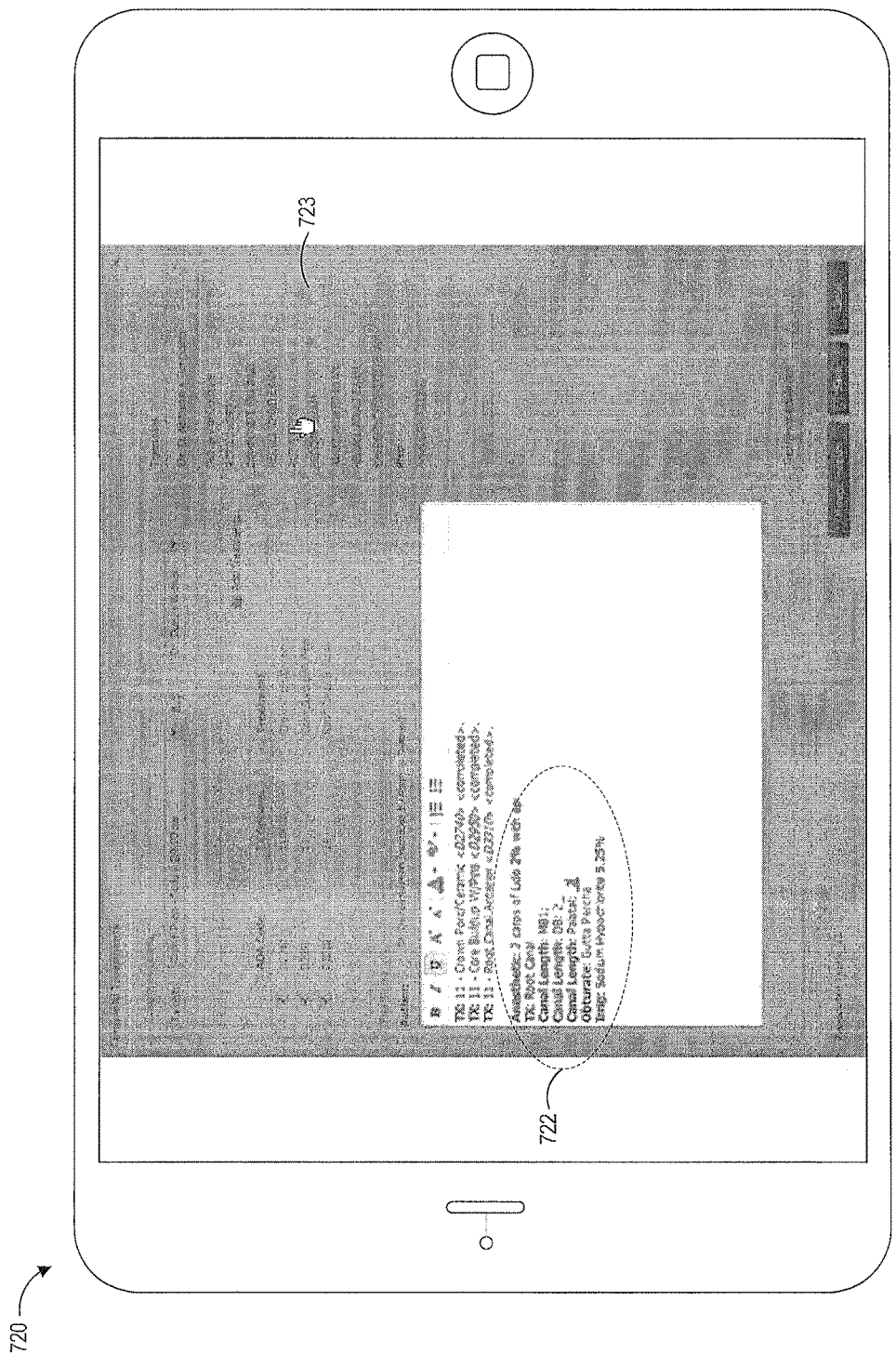

At block 306, the chart and treatment module 136 determines whether a template has been selected by the clinician. If the chart and treatment module 136 determines that a template has been selected by the clinician, the chart and treatment module 136 can add the template to a text box or create a new user interface with the added template. The clinician may select a template using drag and drop functionality to drag a template to clinician notes or a patient's record. For example, the chart and treatment module 136 may add the block of text associated with the template and insert it into a current cursor location in the text box. For example, as illustrated in FIGS. 7A and 7B, when the clinician clicks on the "RCT" (e.g., root canal treatment) template, the chart and treatment module 136 adds the block of text associated with the template (e.g., "Anesthetic," "TX," "Canal Length," "Obturate," and "Irrig" in the example of FIG. 7B. The clinician may further modify the box of text to fill in any blanks or modify any default values. In the example of FIG. 7B, the canal lengths have highlighted blanks, which can be filled in by the clinician.

When the clinician is done adding the notes, the chart and treatment module 136 receives, at block 310, the completed clinician notes associated with the completed treatment. At block 312, the chart and treatment module 136 incorporates or stores the completed clinician notes in association with the completed treatment and/or the patient record. The completed clinician notes may be stored in the data repository 160 shown in FIG. 1.

Although the post-treatment narrative recordation process 300 is described in the context of entering clinician notes for completed treatments, the embodiments of the present disclosure are not limited as such, and techniques and methods described herein may apply to any note taking or narrative-recording generally.

IV. Example Dental Office Management Service Interfaces

FIGS. 4 through 12 depict various user interfaces for providing a dental office management service to clinicians. Each of the user interfaces shown includes one or more user interface controls that can be selected by a user, for example, using a browser or other application software (including mobile application software). The user interface controls shown are merely illustrative examples and can be varied in other embodiments. For instance, buttons, dropdown boxes, select boxes, text boxes, check boxes, slider controls, and other user interface controls shown, may be substituted with other types of user interface controls that provide the same or similar functionality. Further, user interface controls may be combined or divided into other sets of user interface controls such that similar functionality or the same functionality may be provided with different looking user interfaces. Moreover, each of the user interface controls may be selected by a user using one or more input options, such as a mouse, touch screen input, or keyboard input, among other user interface input options. For illustrative purposes, many of these user interfaces are shown implemented in a tablet computing device, such as a tablet that may be used by a dental assistant or other clinician. However, any of these user interfaces may be implemented in any other computing device, examples of which are provided above.

Figure 4:
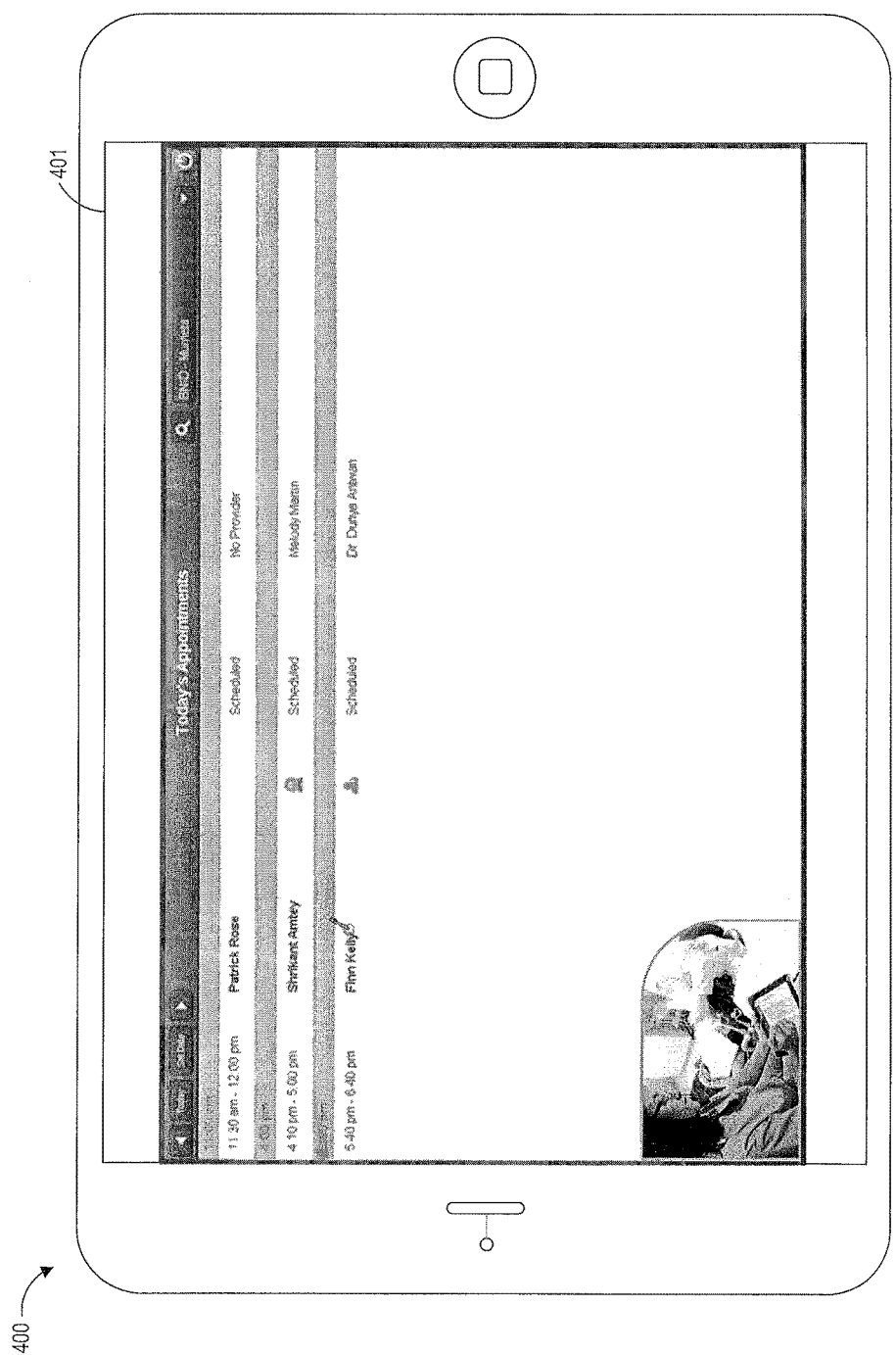
FIG. 4 depicts an example user interface that provides a patient schedule.

Turning to FIG. 4, an example user interface 400 that may be presented in a mobile application 901 (or other application) is shown. The mobile application 401 may be installed on a user device such as one of the user devices 102. FIG. 4 shows a list of patient appointments with the corresponding dentists. After the dentists review the treatment and review the automated clinical notes, they can save the notes. They can then add restorative and clinical services notes to direct the treatment counselor on the order, priority, and options for treatment. In FIG. 9B, an example user interface 920 shows the notes for a patient that have been added by multiple clinicians.

Figure 5B:
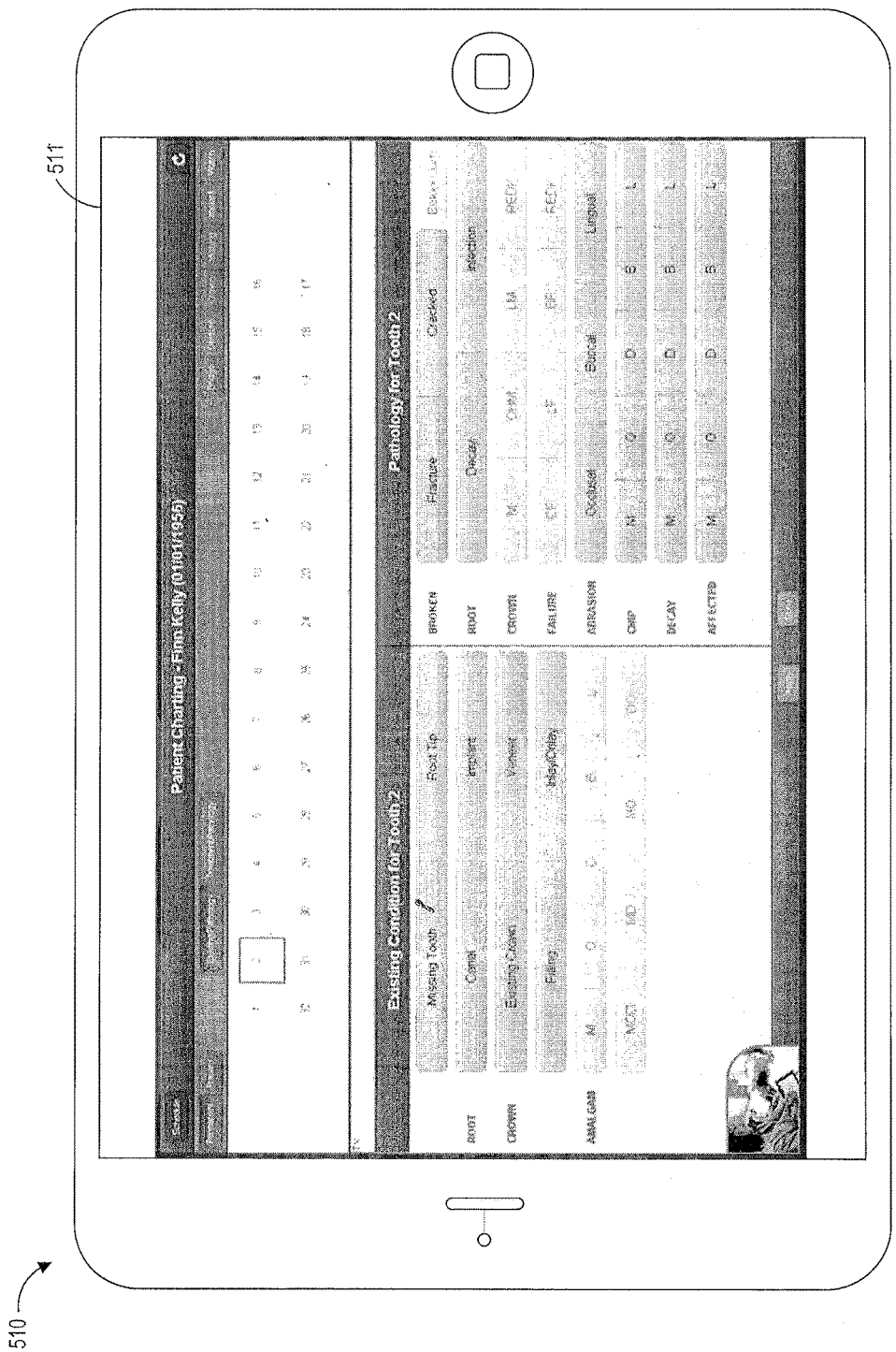
Figure 5C:
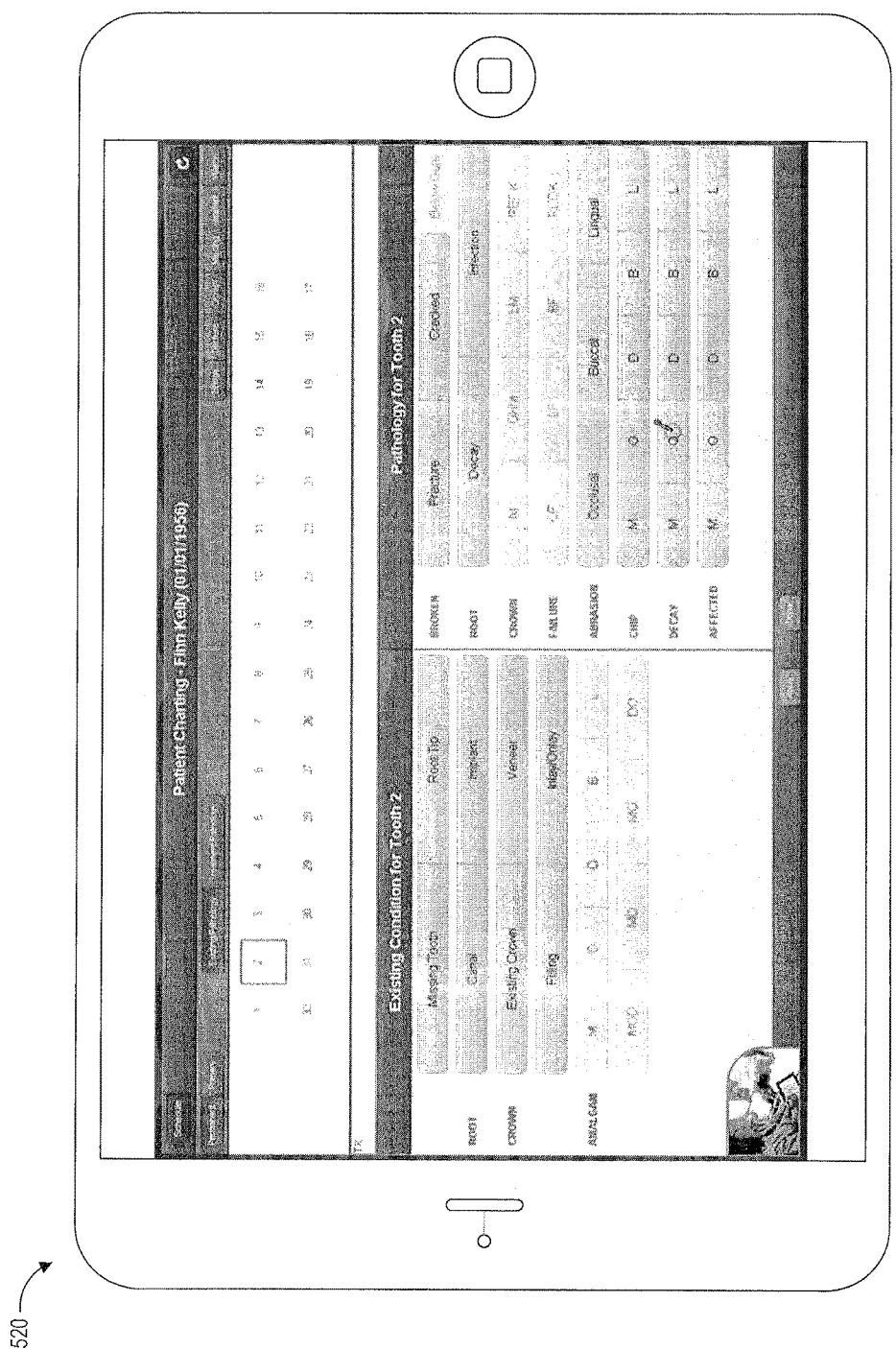
Figure 5D:
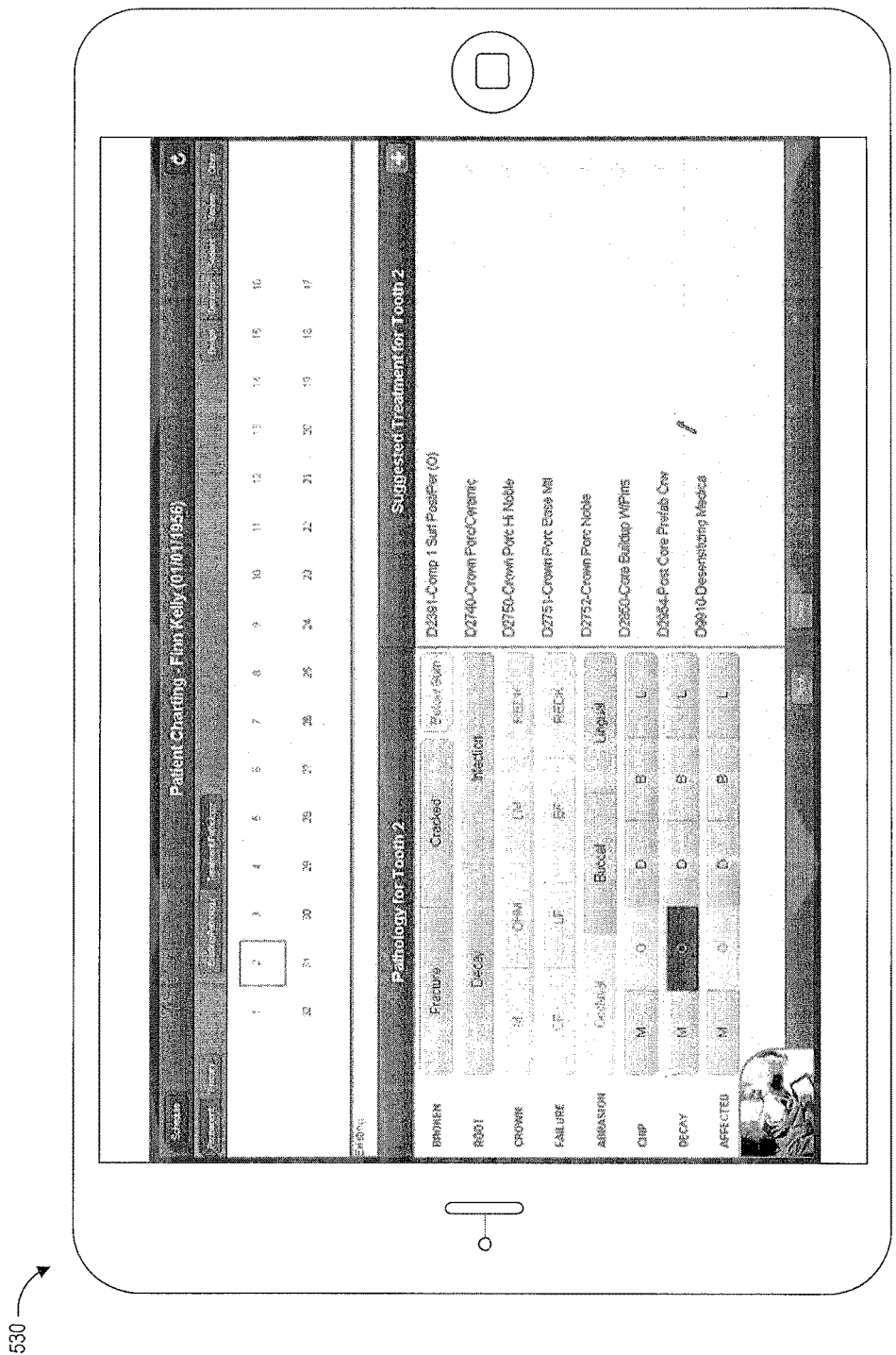
Figure 5E:
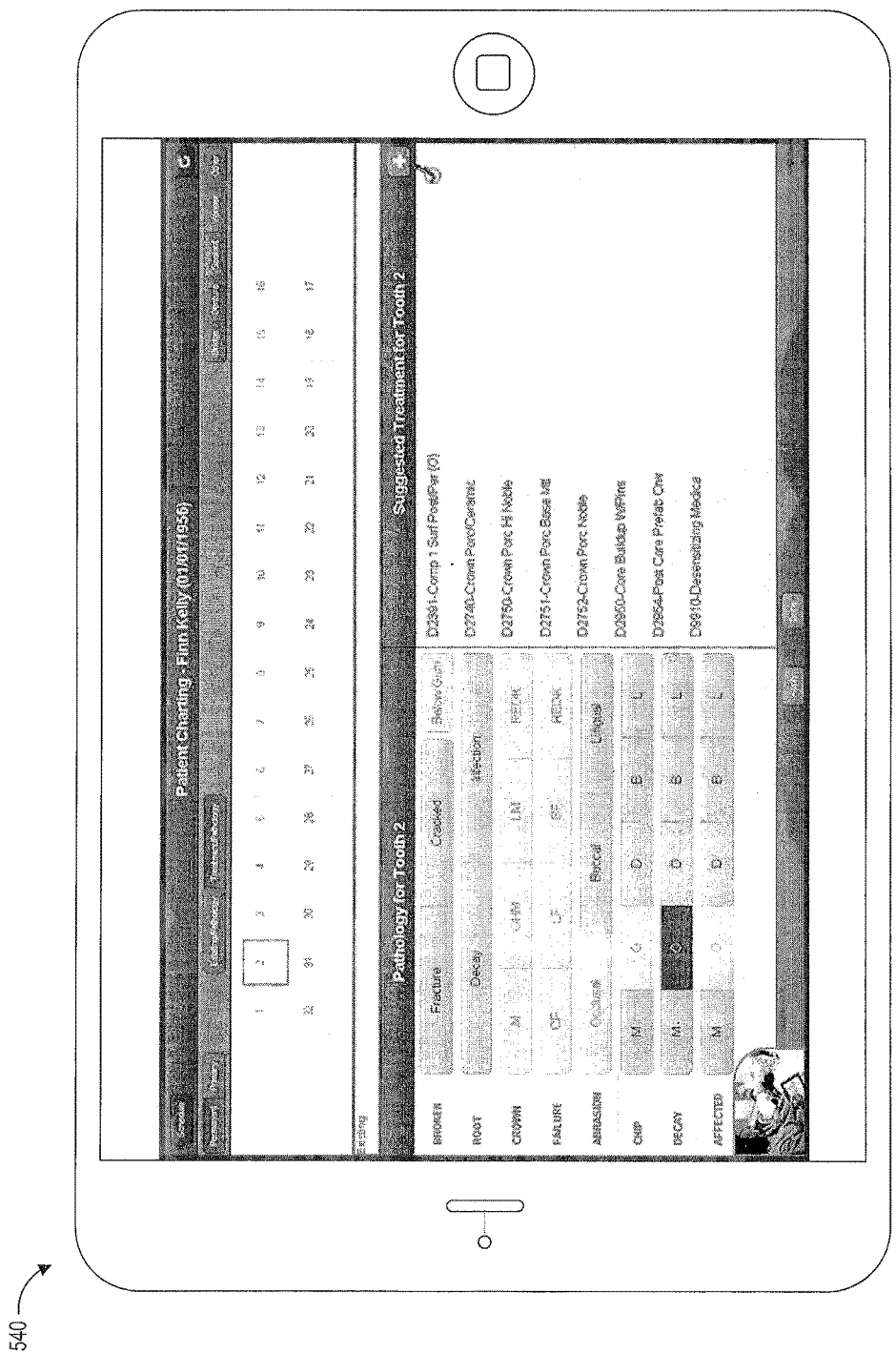
Figure 5F:
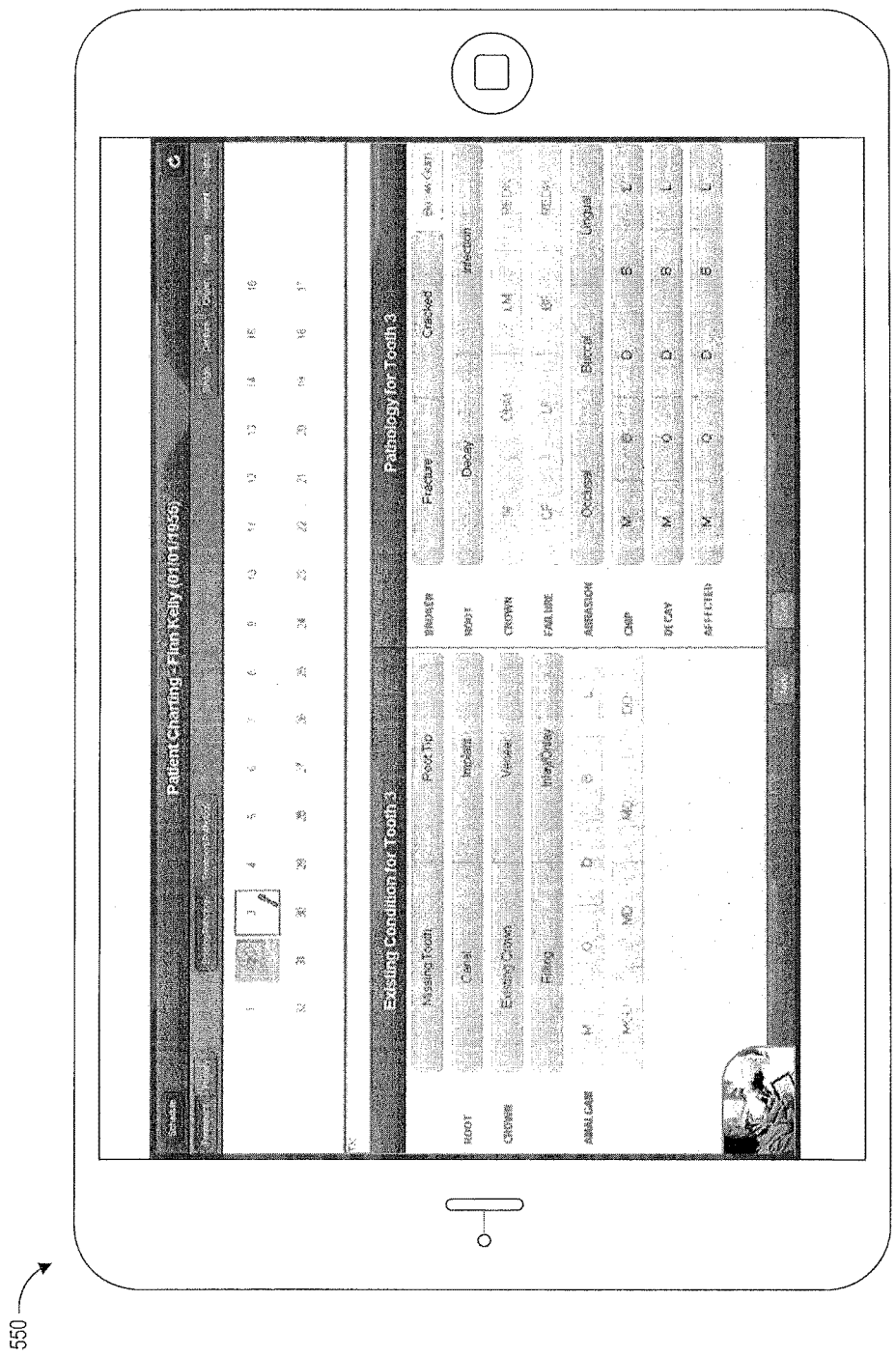
Figure 5G:
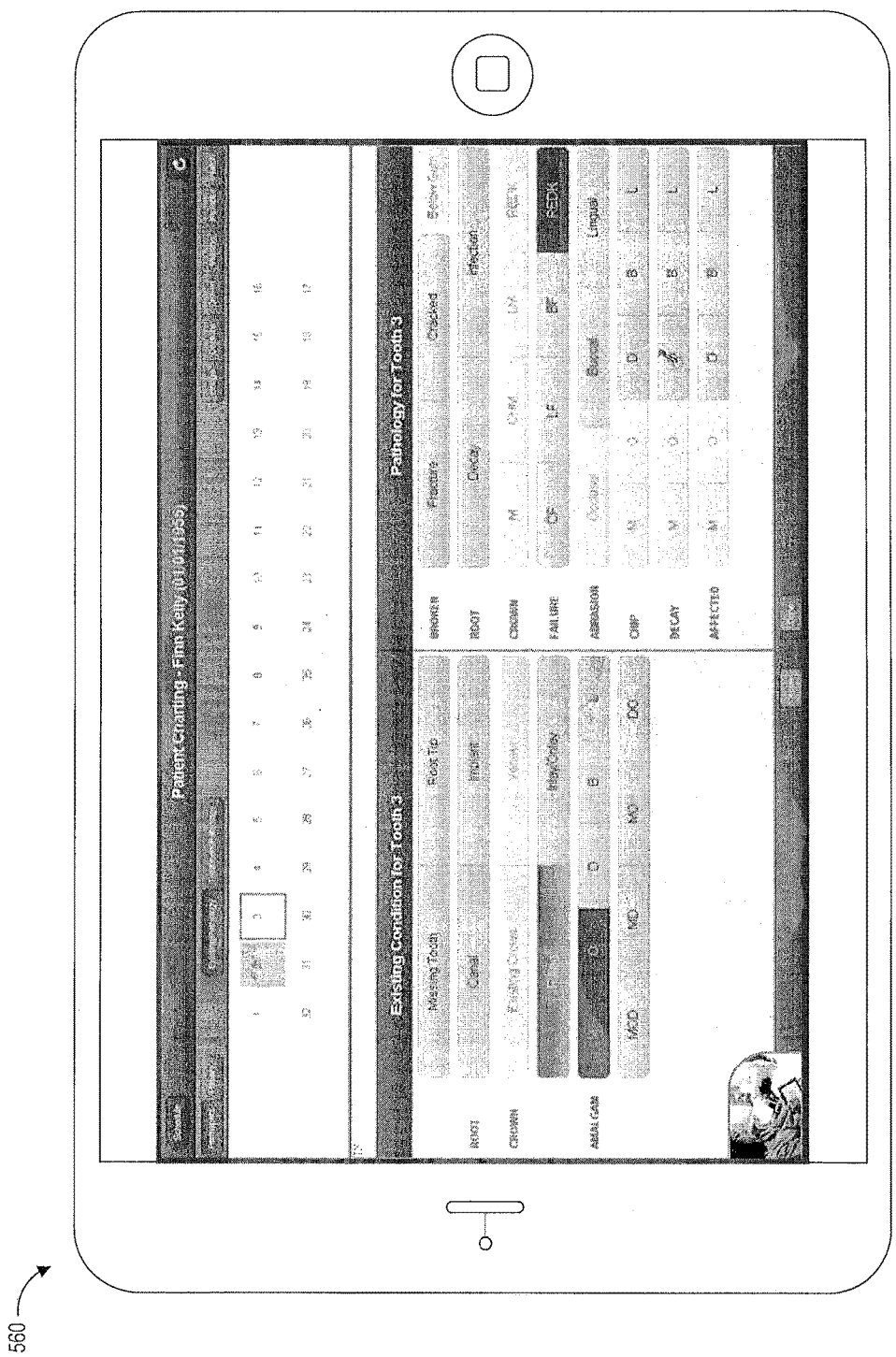
Figure 5H:
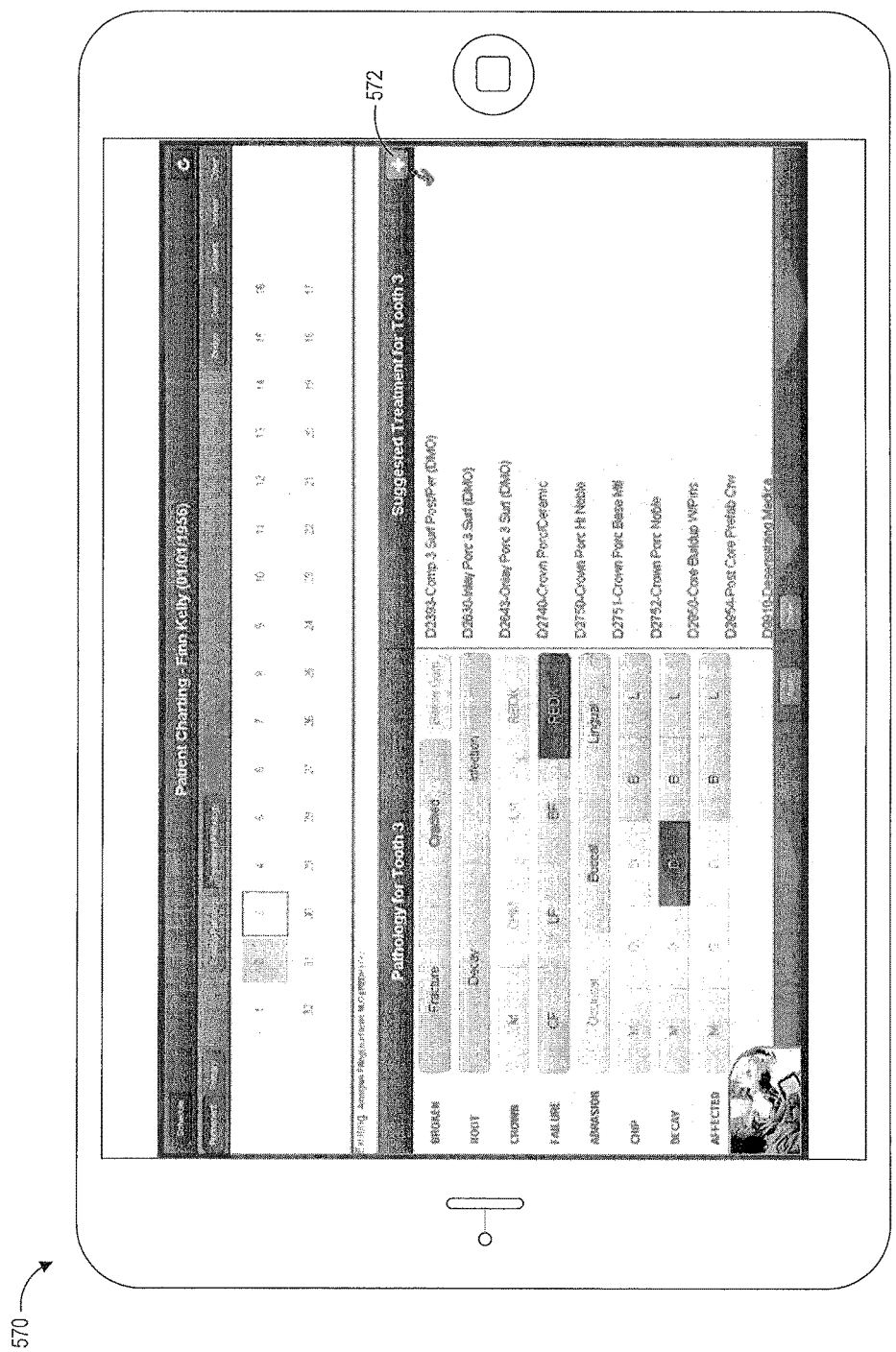
Figure 5I:
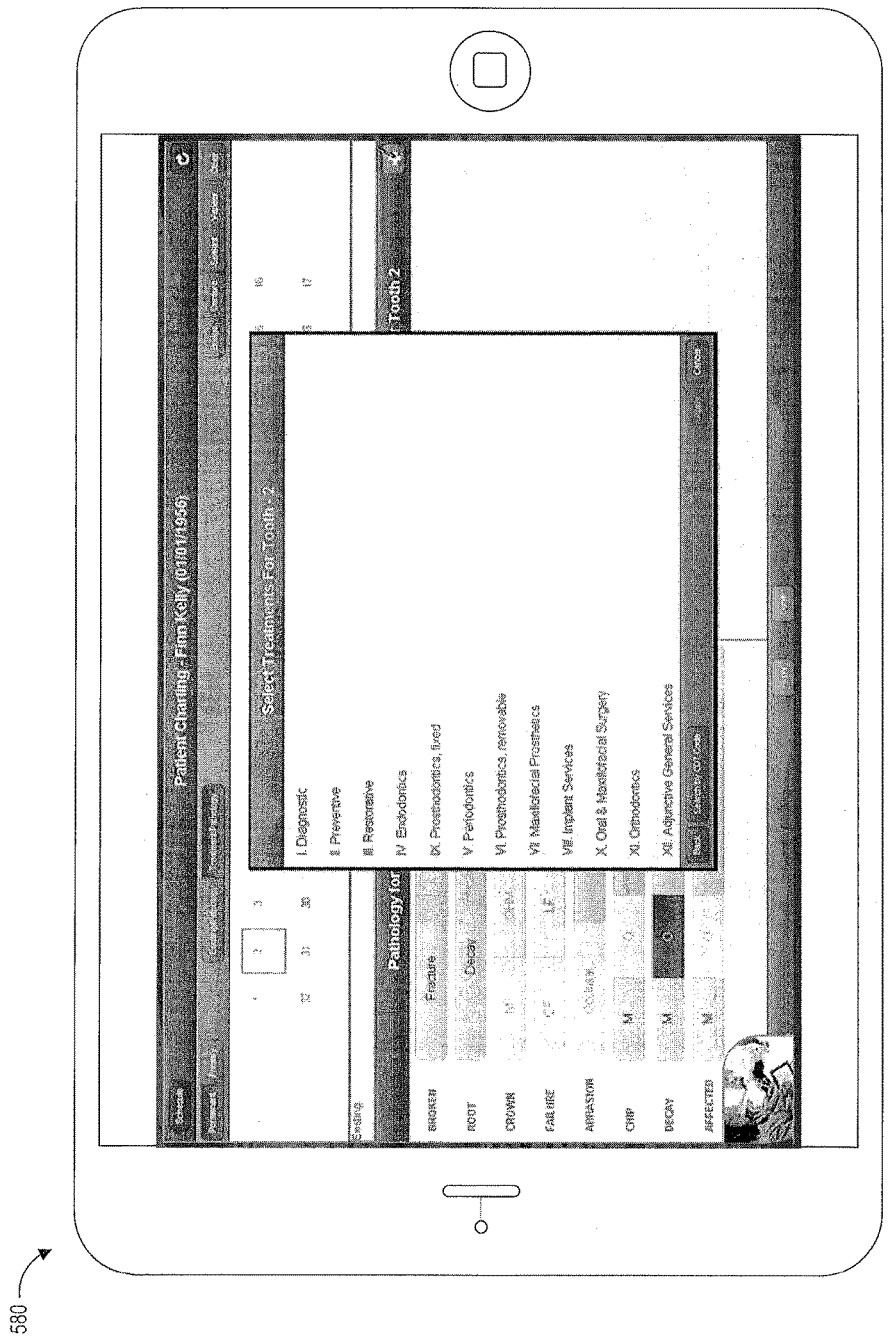

With reference to FIGS. 5A-5I, example user interfaces for providing treatment recommendations based on existing conditions and pathology are described. In FIG. 5A, an example user interface 500 that may be presented in a mobile application 501 (or other application) is shown. The mobile application 501 may be installed on a user device such as one of the user devices 102. FIG. 5A provides user interface (UI) controls for a clinician to be able to specify the existing conditions and pathology of a patient's teeth. As discussed in connection with FIG. 2, the controls may include a plurality of icons corresponding to the respective teeth of the patient (e.g., icons 502 that are labeled 1 through 32), one or more buttons 503 for specifying the existing condition of the tooth (e.g., missing tooth, root tip, canal, implant, existing crown) and the location/direction of the existing condition (e.g., mesial, occlusal, distal, facial, lingual, and the like), and one or more buttons 504 for specifying the pathology of the tooth (e.g., broken, root, crown, failure, abrasion, chip, decay, affected, and the like). In the example of FIG. 5A, the icons 502 also indicate the current status of the tooth (e.g., root tip, chipped, filling, missing, and the like). FIG. 5B shows another example user interface 510 that may be presented in a mobile application 511 (or other application). The user interface 510 provides additional user interface (UI) controls (e.g., veneer, inlay/overlay, filling, and the like). In the example of FIG. 5B, the current statuses of the teeth are not shown.

For example, the clinician, who may be a dental assistant, may be in the operatory room with the dentist as the dentist is examining the patient. The dentist may say, "Tooth #2 has occlusal decay, which can be addressed with a one surface composite or tooth colored filling." In response, the dental assistant may select Tooth 2 from the controls provided at the top of the screen of FIG. 5B, and then select "O" in the "Decay" row, as shown in user interface 520 of FIG. 5C. After the dental assistant selects the "O" (or "occlusal") button, a user interface 530 shown in FIG. 5D is displayed on the screen. As shown in FIG. 5D, a list of suggested treatments for Tooth 2 is displayed on the bottom right side of the screen. In response to the dentist's comment (e.g., " . . . which can be addressed with a one surface composite or tooth colored filling"), the dental assistant may select the button corresponding to "D2391-Comp 1 Surf Post/Per (O)." In the example of FIG. 5D, each of the suggested treatments is associated with an ADA code that is used for insurance purposes. Thus, in certain embodiments, the clinician does not have to enter the ADA codes separately after a suggested treatment is selected. The suggested treatments may include one or more abbreviations commonly used among dental professionals. When the clinician selects one of the suggested treatments, a check mark may be displayed next to the selected treatment, as shown in FIG. 5E. In addition, as shown in the top right corner of the user interface 540 of FIG. 5E, the dental office management service 130 may allow the dental assistant to record any bridge, denture, sealants, veneers, or the like.

Continuing on with the same example, the dentist may then examine Tooth 3 of the patient. The dentist may say to the dental assistant, "Tooth 3 has an old silver filling with decay. I am recommending a 3-surface composite or a tooth colored filling." In response, the dental assistant may select Tooth 3 from the controls provided at the top of the screen as shown in user interface 550 of FIG. 5F, and then select "Filling," "M," and "O" in the existing conditions section, and select "REDK" in the "Failure" row and "D" in the decay row, as shown in user interface 560 of FIG. 5G. After the dental assistant selects the "D" button, a user interface 530 shown in user interface 570 of FIG. 5H is displayed on the screen. As shown in FIG. 5H, a list of suggested treatments for Tooth 3 is displayed on the bottom right side of the screen. In response to the dentist's comment (e.g., "I am recommending a 3-surface composite or a tooth colored filling."), the dental assistant may select the button corresponding to "D2393-Comp 3 Surf Post/Per (DMO)."

In some cases, the treatment recommended by the dentist may not appear on the list of suggested treatments. In such cases, the clinician can select the "+" button 572 shown in FIG. 5H. When the clinician selects the "+" button 572, a list of available treatments may be displayed on the screen, as shown in user interface 580 of FIG. 5I. The list may be a list of categories of available treatments, and upon selection by the clinician, the categories may further expand into further categories or a list of selectable treatments. As discussed in connection with FIG. 2, when the clinician selects a treatment from the list of available treatments, the selected treatment may be associated with the corresponding existing conditions and/or the pathology of the tooth such that when the clinician specifies similar conditions and/or pathology in the future, the selected treatment may be included in the list of suggested treatments. Thus, through this treatment list customization feature, in certain embodiments, the clinician may not have to browse through the complete list of available treatments to find the same custom treatment again. More generally, any custom treatment added by a clinician corresponding to a specific tooth pathology for one patient can be stored by the charts and treatment module 136 for subsequent recommendation as a potential treatment for another patient having the same or similar tooth pathology.

Turning now to FIGS. 6A-6C, an example user interface for displaying some or all the existing conditions, pathology, and treatment information is described. In FIG. 6A, an example user interface 600 that may be presented in a mobile application 601 (or other application) is shown. As shown in FIG. 6A, the user interface 600 displays the list of tooth conditions and pathology. For example, the list of tooth conditions and pathology may be automatically generated by the dental office management service 130, based on the input by the clinician via the user interface controls (e.g., in the example of FIGS. 5A-5I). FIG. 6B illustrates user interface 620, which shows additional notes added by the clinician. Thus, the dentist may use the user interfaces shown in FIGS. 6A and 6B to verify that the dental assistant has entered all the existing conditions, pathology, and treatment information accurately, and the dentist may add additional notes. FIG. 6C illustrates user interface 640, which shows another view in which the suggested treatments selected by the clinician are saved in a list format.

With reference to FIGS. 7A and 7B, example user interfaces for adding post-treatment clinician notes are shown. After the treatments recommended by the dentist and approved by the patient are completed, the dentist may wish to add additional notes in association with one or more of the completed treatments. In FIG. 7A, an example user interface 700 that may be presented in a mobile application 701 (or other application) is shown. The mobile application 701 may be installed on a user device such as one of the user devices 102. As shown in FIG. 7A, the user interface 700 may display to the clinician a list of completed treatments for a particular patient. As the clinician checks the checkboxes 702 next to one or more of the completed treatments, the notes associated with the completed treatments can be added to the textbox 703 for drafting final notes. FIG. 7B shows an example user interface 720 that shows a block of text 722 added to the text box after the clinician has selected one of the templates 723 (either default or previously customized by a clinician) located on the right hand side of the screen. In the example of FIG. 7B, after the clinician activates the button labeled "RCT (UPPER)" by a mouse click or a touch, the block of template text 722 for quickly adding notes about a completed root canal treatment is added to the text box. The block of text 722 added to the text box may have one or more fields or blanks to be filled in by the clinician and/or one or more default values that can be modified by the clinician before being saved in association with the patient record.

Figure 8:
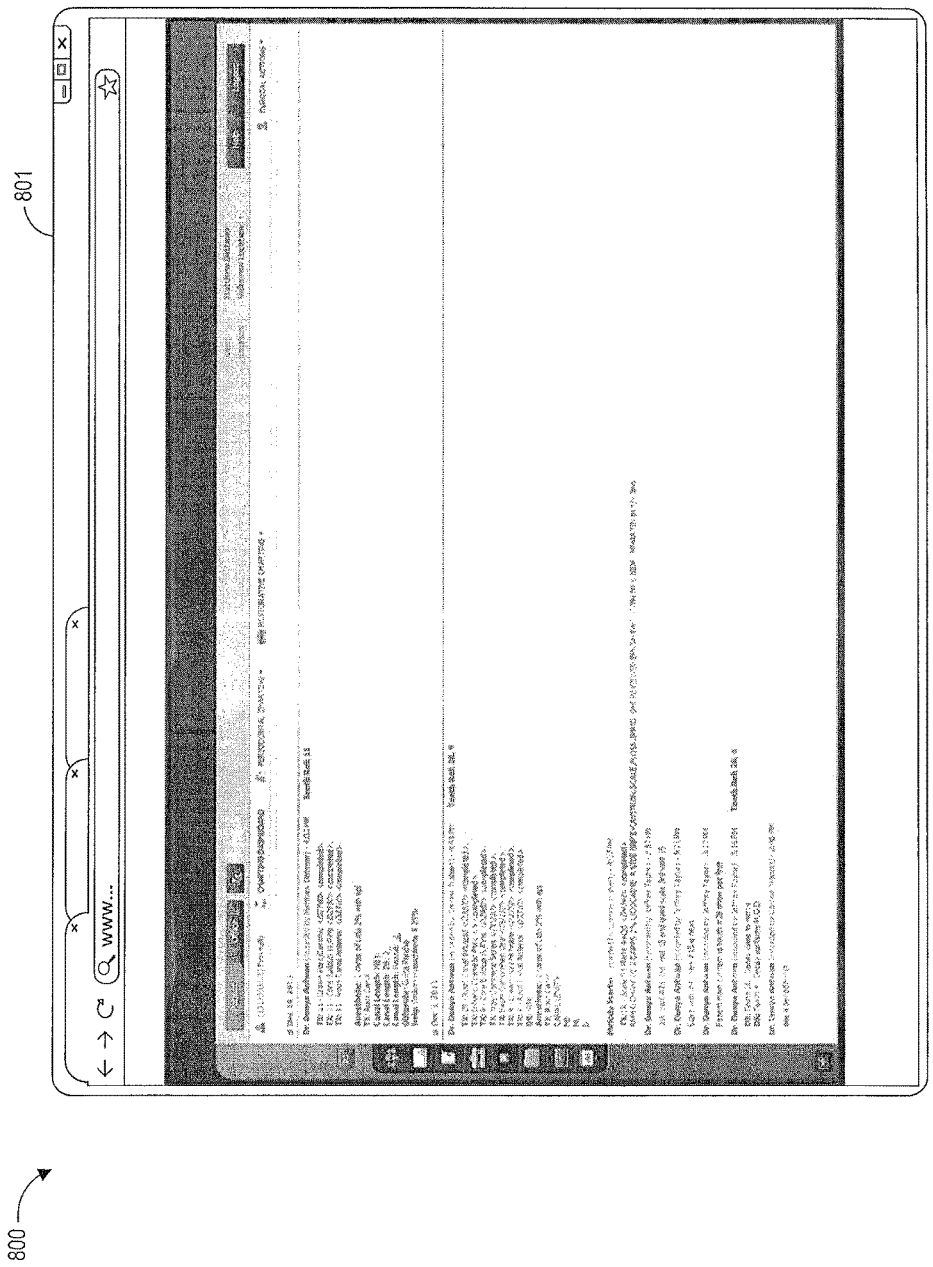
FIG. 8 depicts an example user interface that provides a history of clinician notes.

Turning to FIG. 8, an example user interface 800 that may be presented in a browser 801 (or other application) is shown. The browser 801 may be installed on a user device such as one of the user devices 102. FIG. 8 shows some or all the notes that have been added in association with a particular patient. The notes shown in FIG. 8 also include the post-treatment notes of Dec. 19, 2013, which was completed using a template, as discussed above with reference to FIGS. 7A and 7B. In the example of FIG. 8, the template had fields or blanks that were filled in by the clinician, as indicated by the highlighted "2".

Figure 9A:
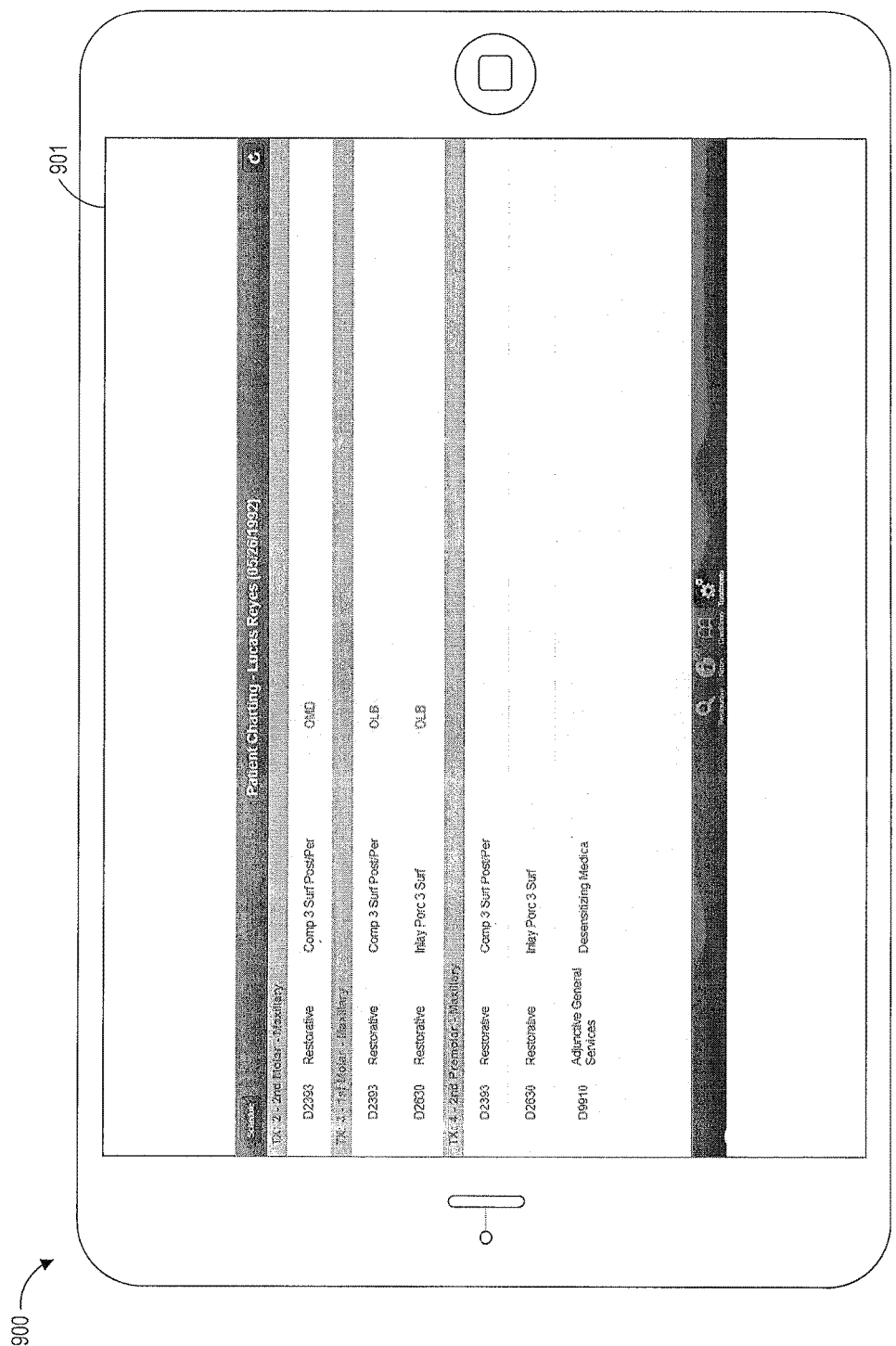
FIGS. 9A and 9B depict example user interfaces for utilizing various functionalities provided by the dental office management service.
Figure 9B:
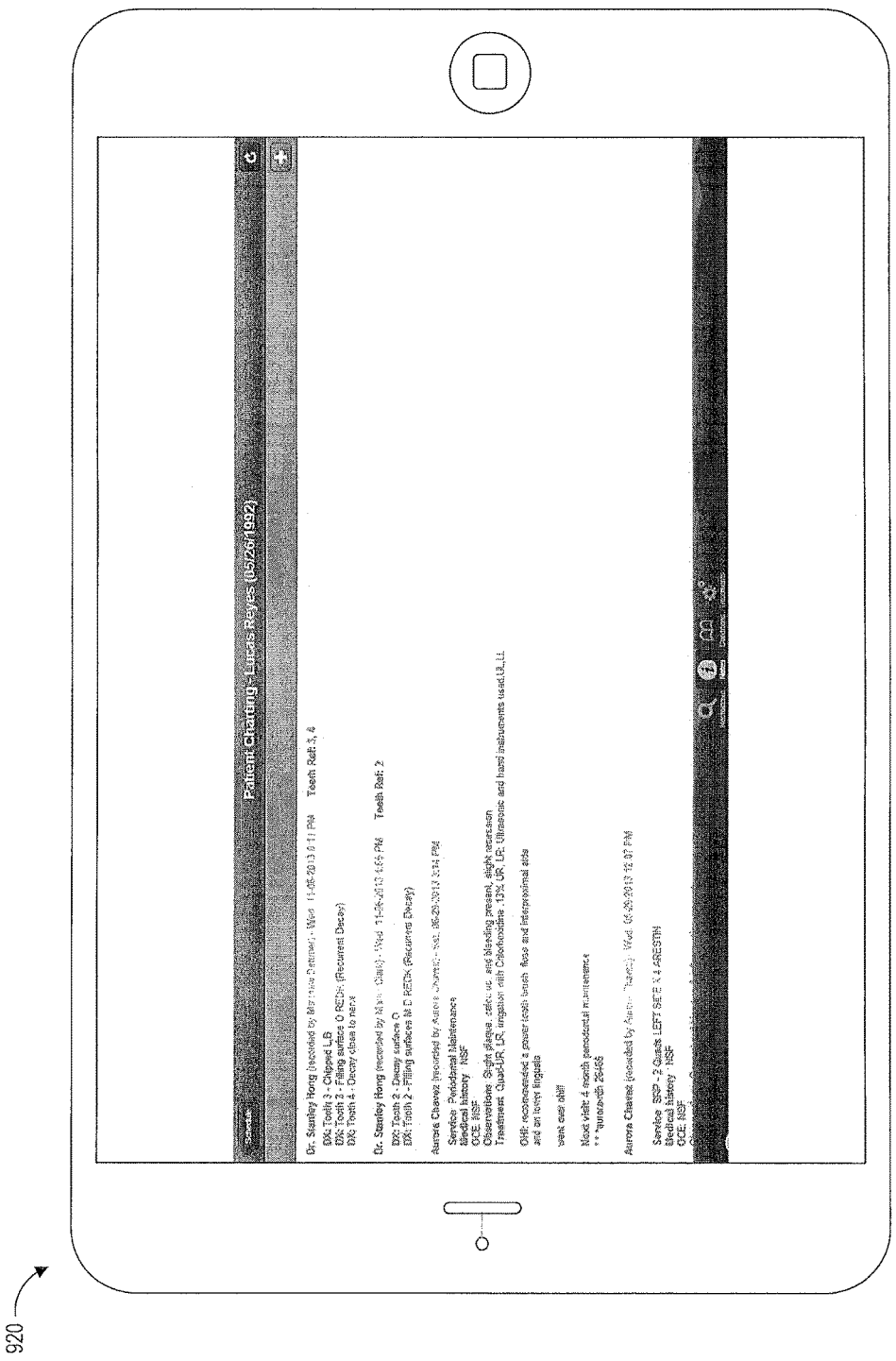

Turning to FIG. 9A, an example user interface 900 that may be presented in a mobile application 901 (or other application) is shown. The mobile application 901 may be installed on a user device such as one of the user devices 102. After the dentists review the treatment and review the automated clinical notes, they save the notes. They can then add restorative and clinical services notes to direct the treatment counselor on the order, priority, and options for treatment. In FIG. 9B, an example user interface 920 shows the notes for a patient that have been added by multiple clinicians.

Figure 10A:
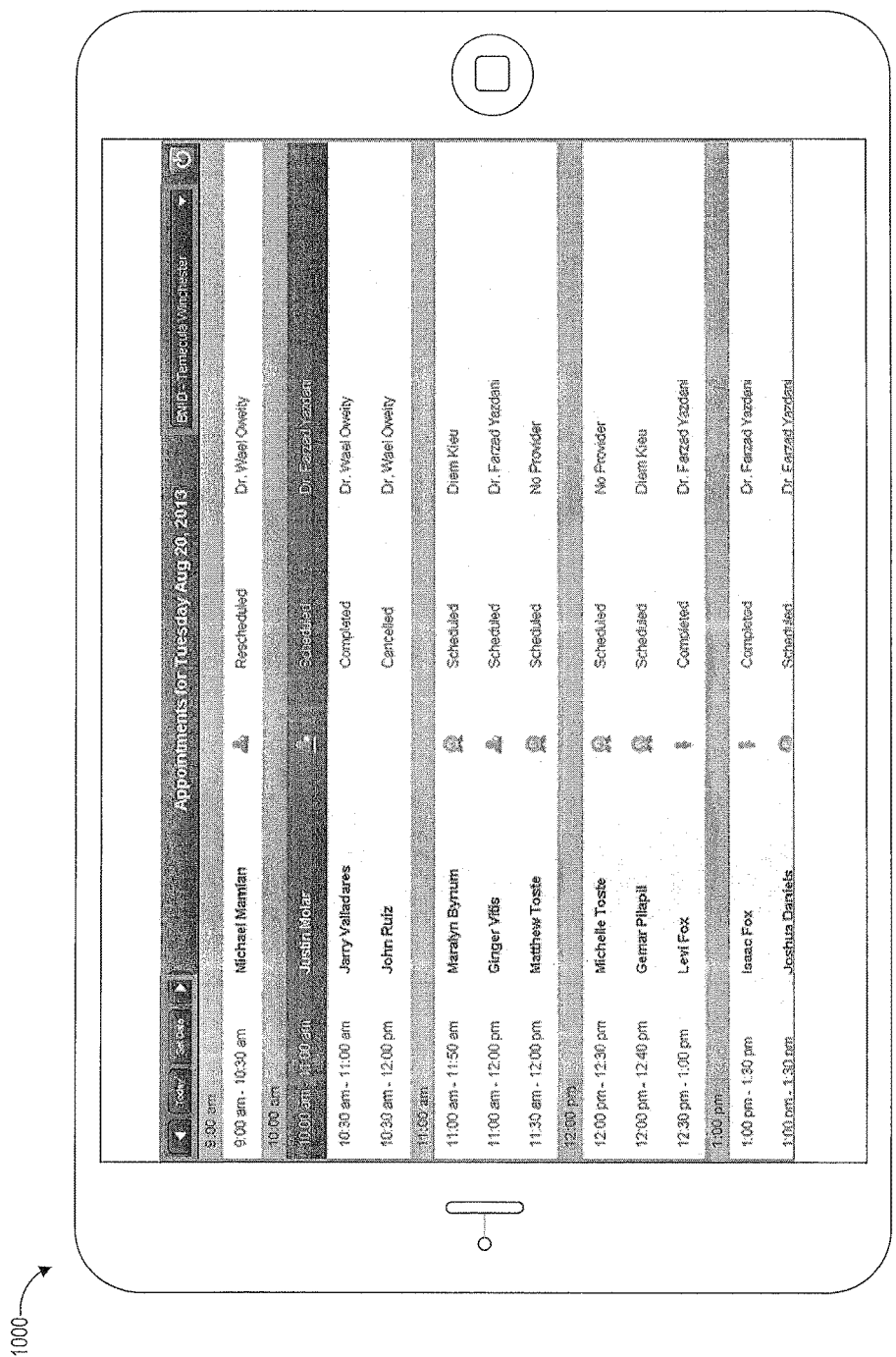
FIGS. 10A-10V depict example user interfaces for utilizing various functionalities provided by the dental office management service.
Figure 10B:
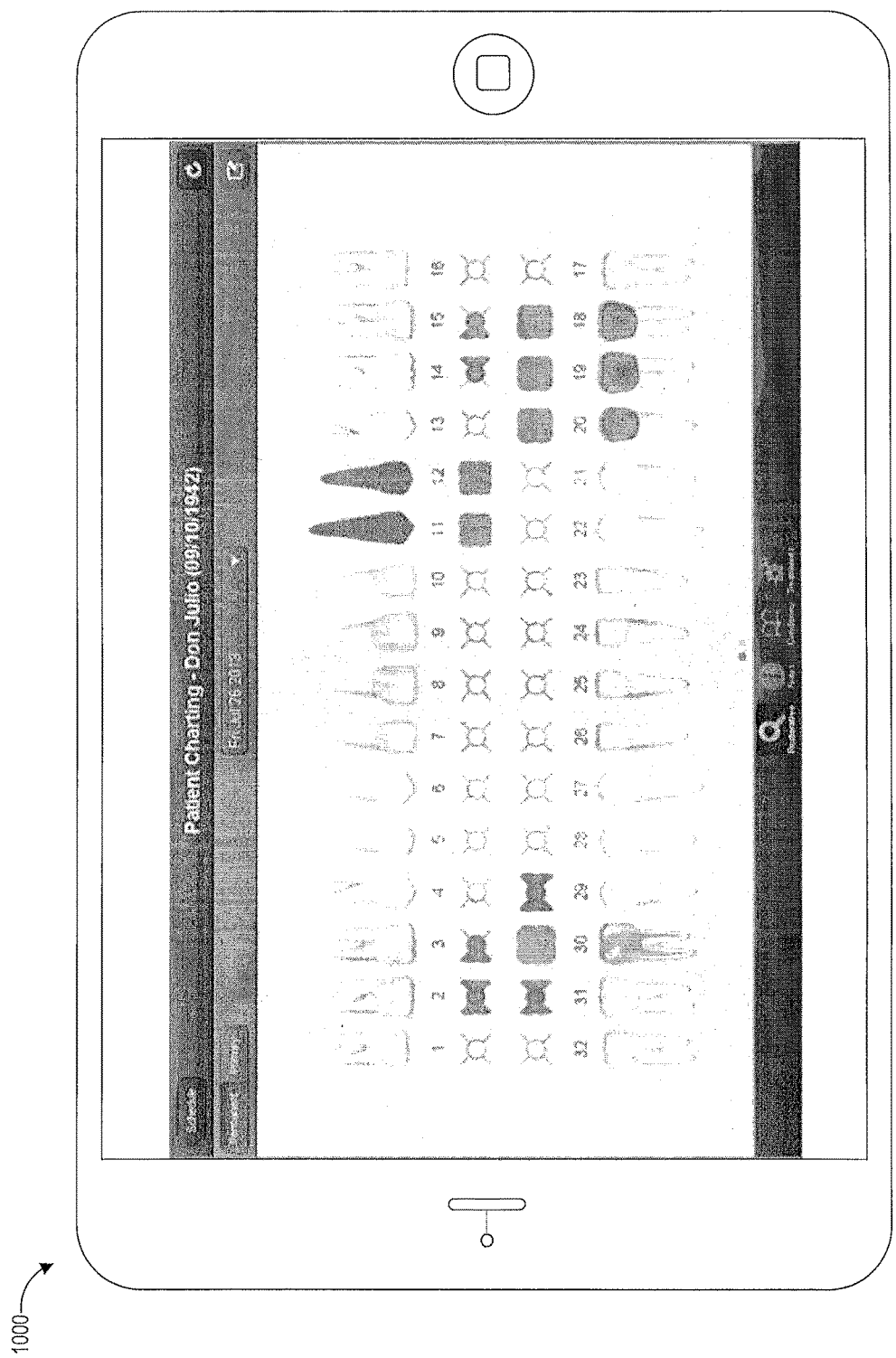
Figure 10C:
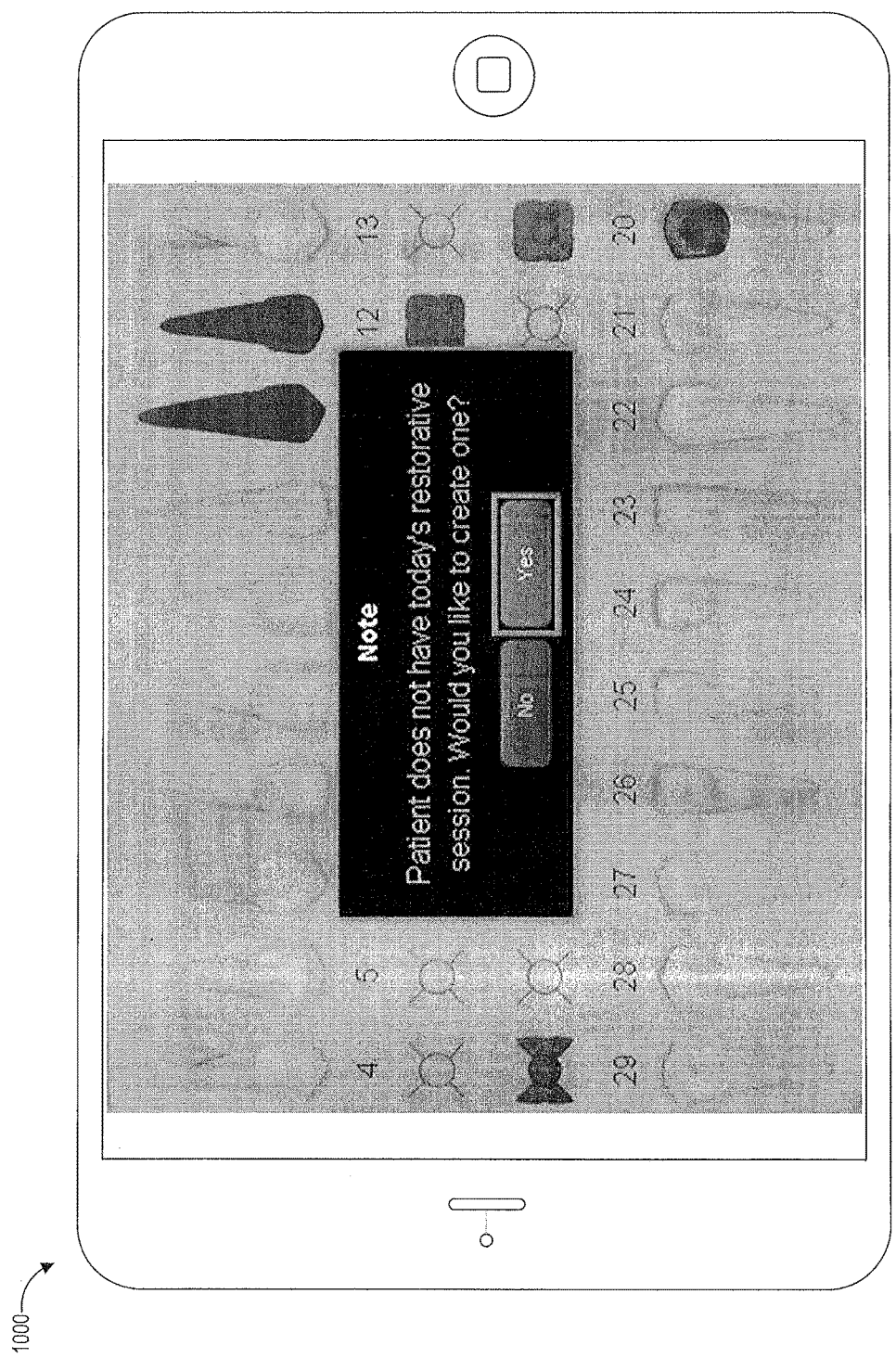
Figure 10D:
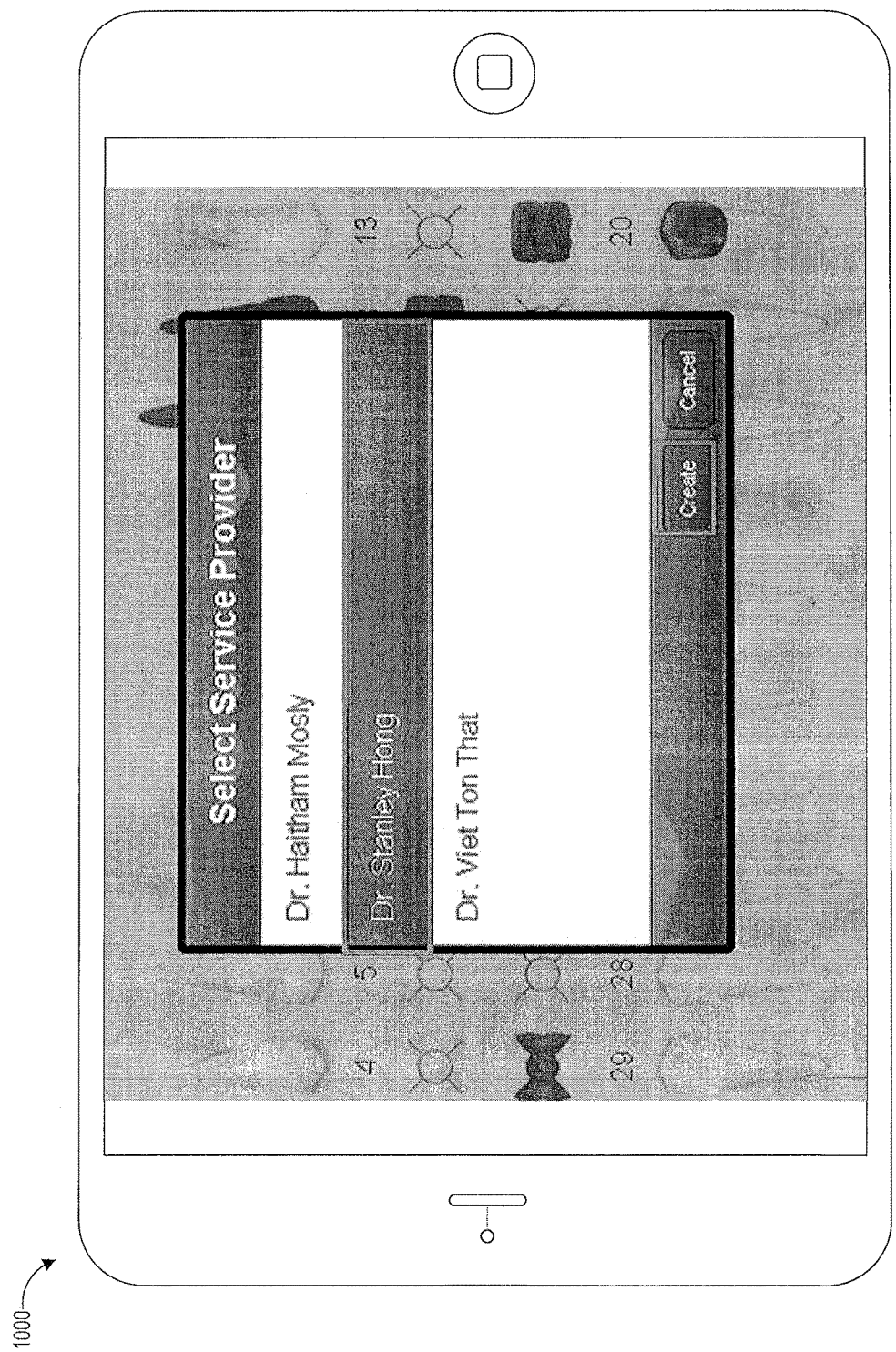
Figure 10E:
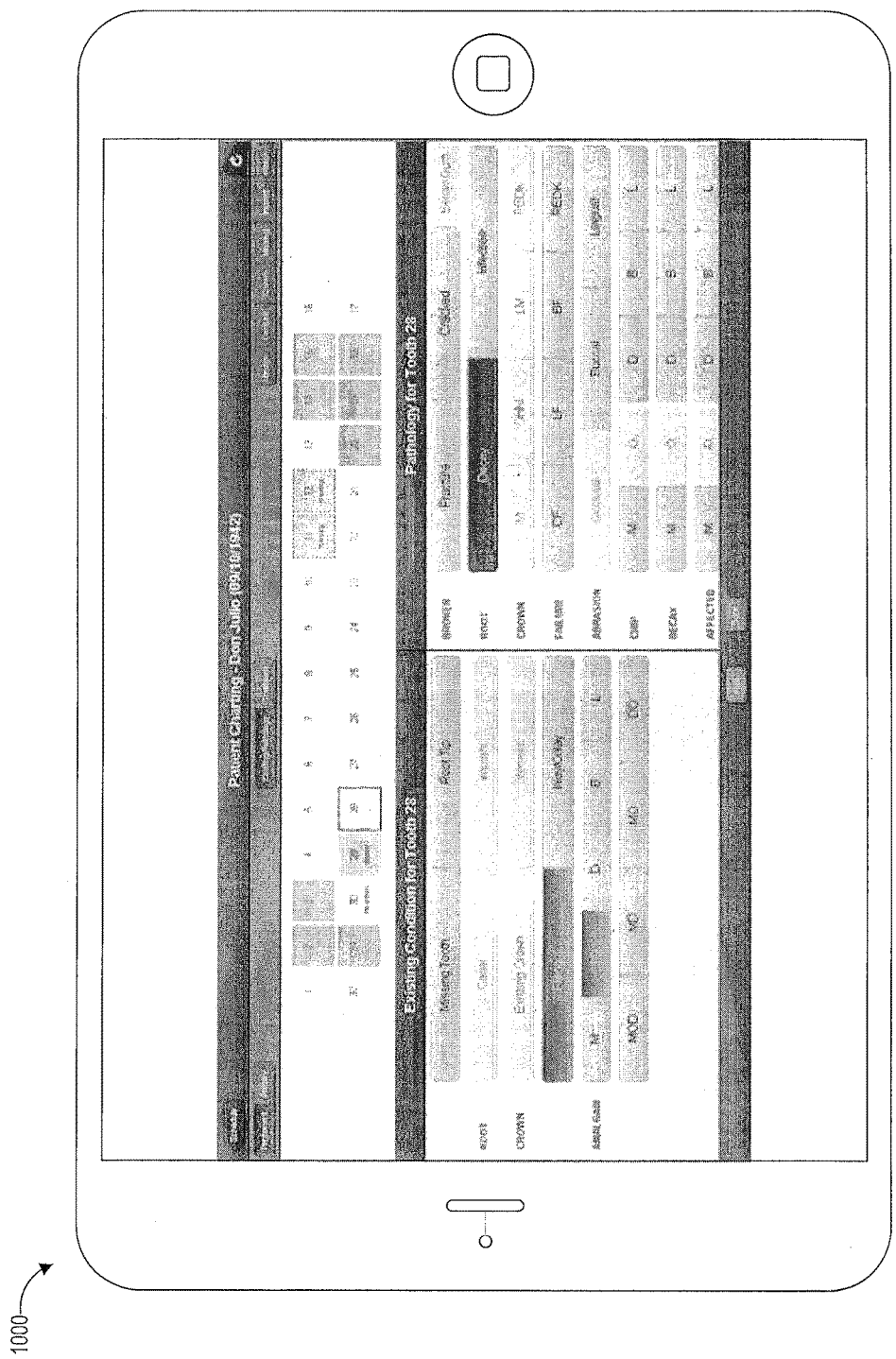
Figure 10F:
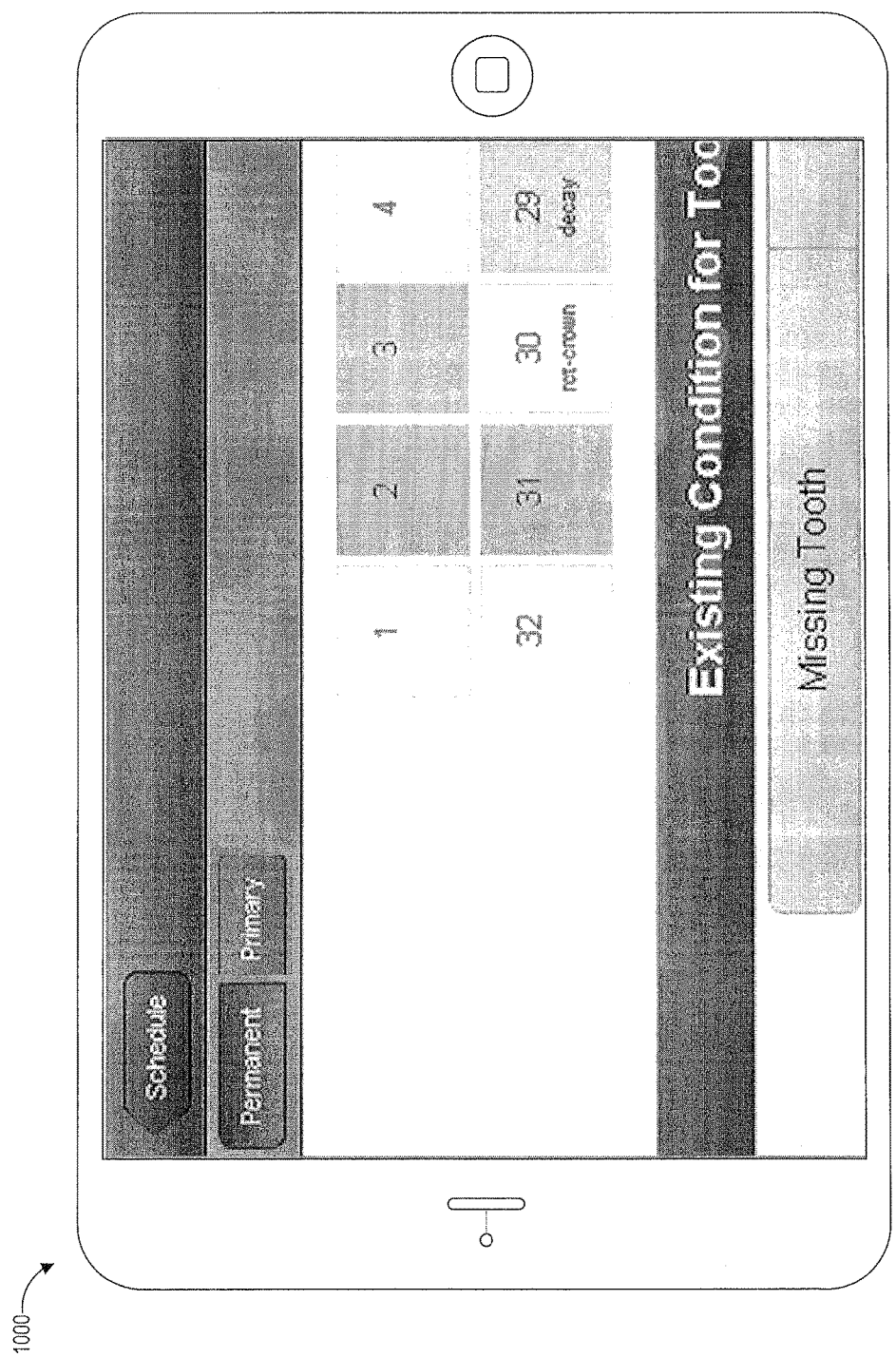
Figure 10G:
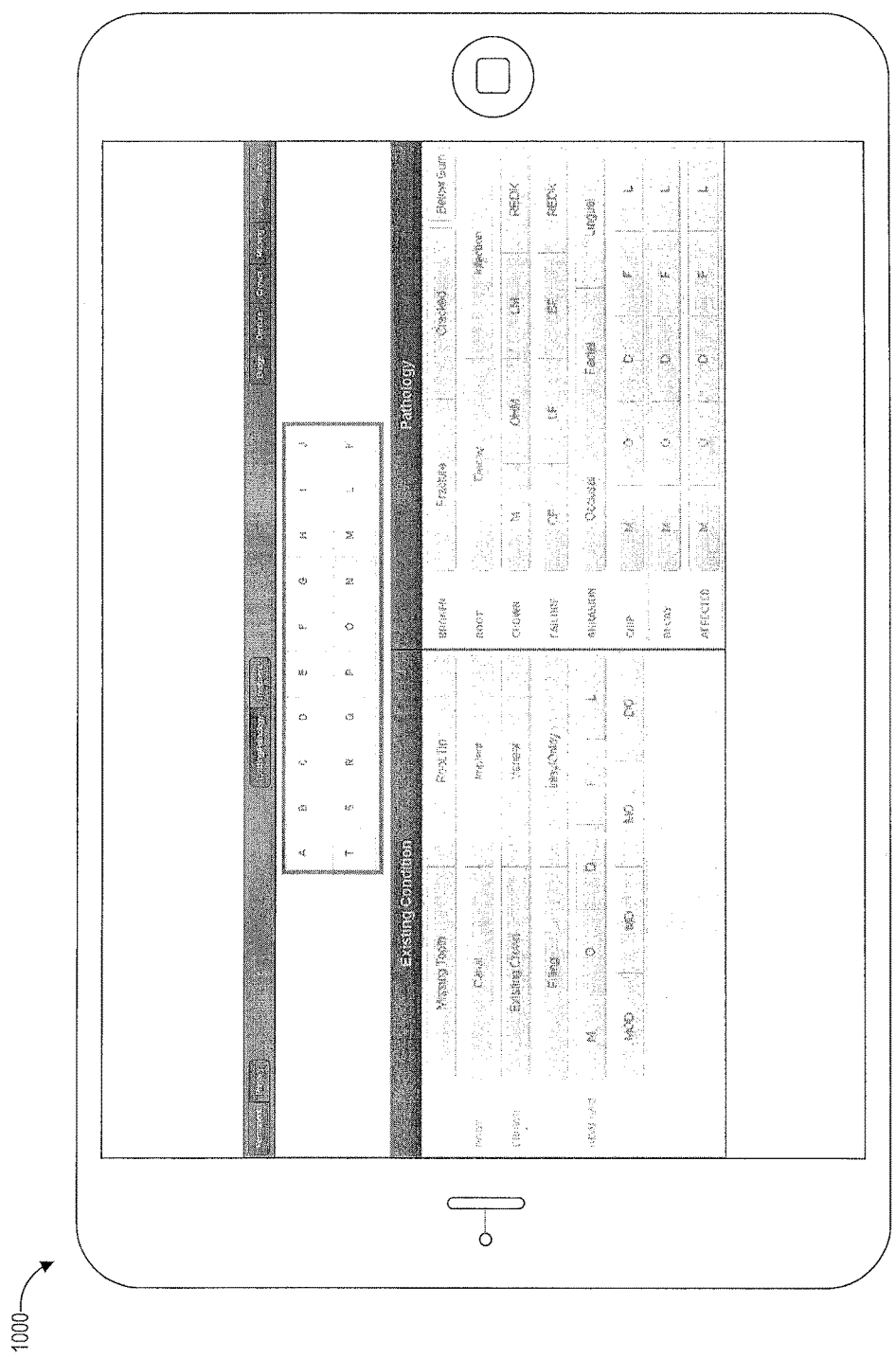
Figure 10H:
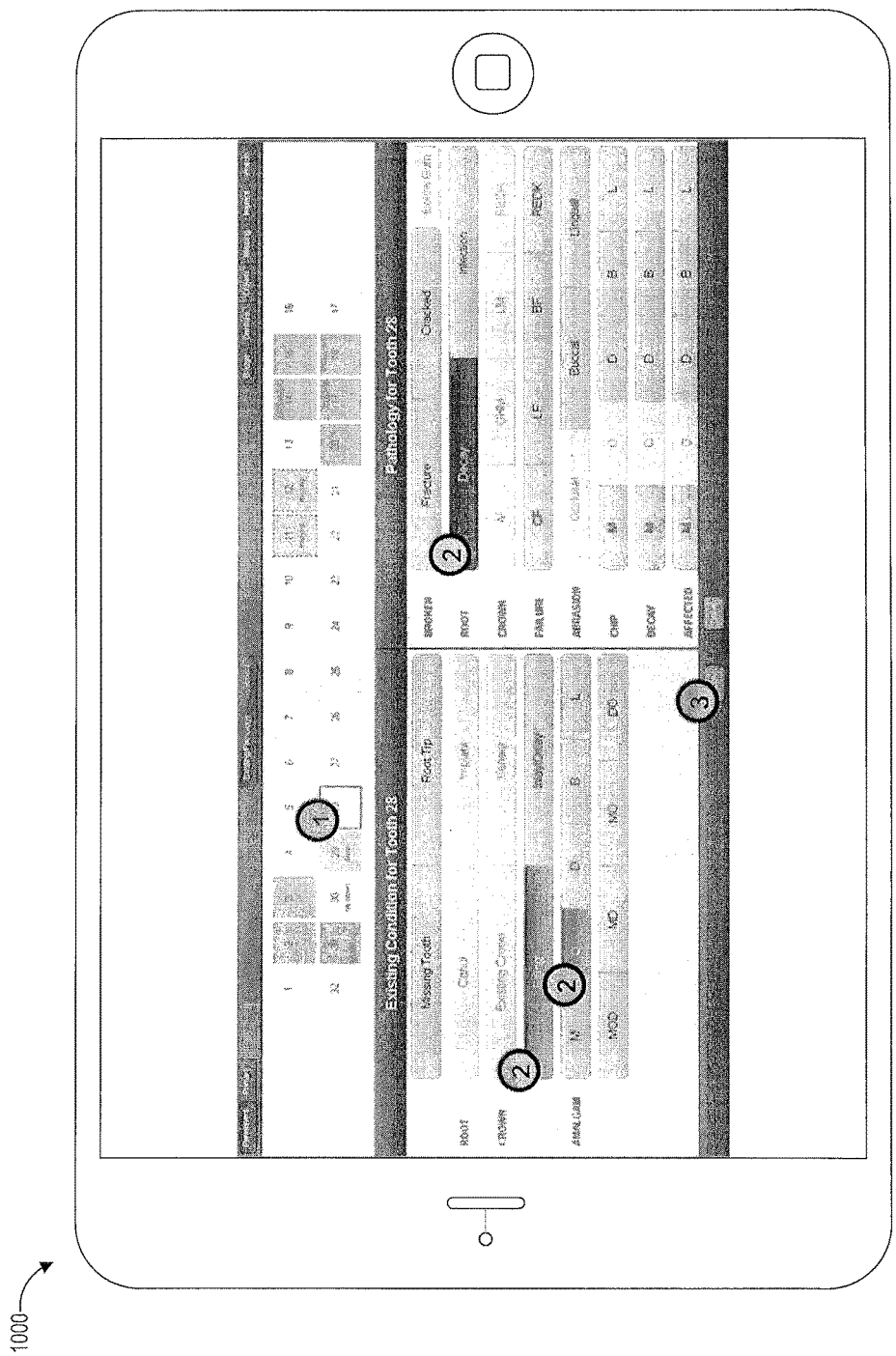
Figure 10I:
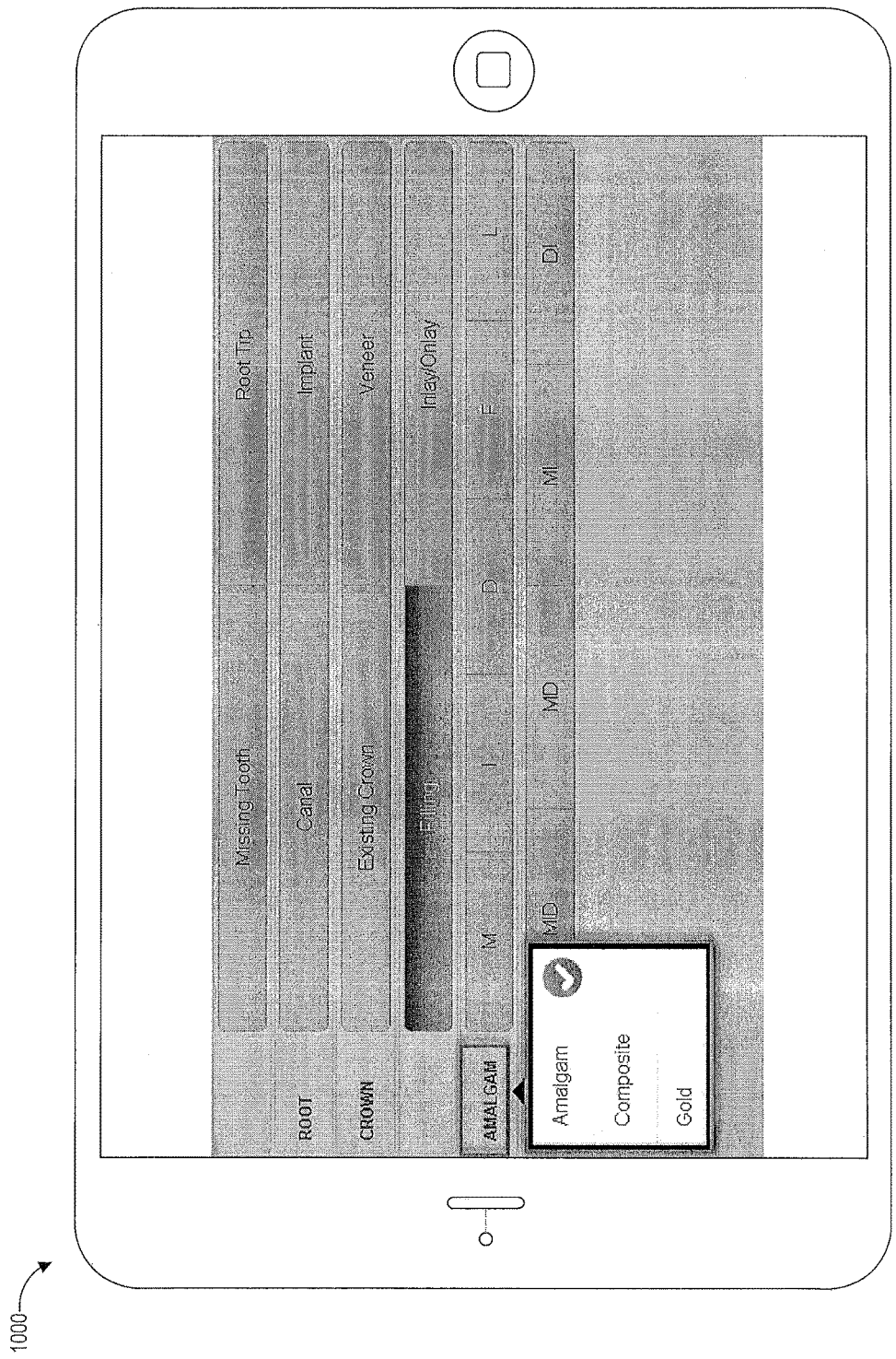
Figure 10J:
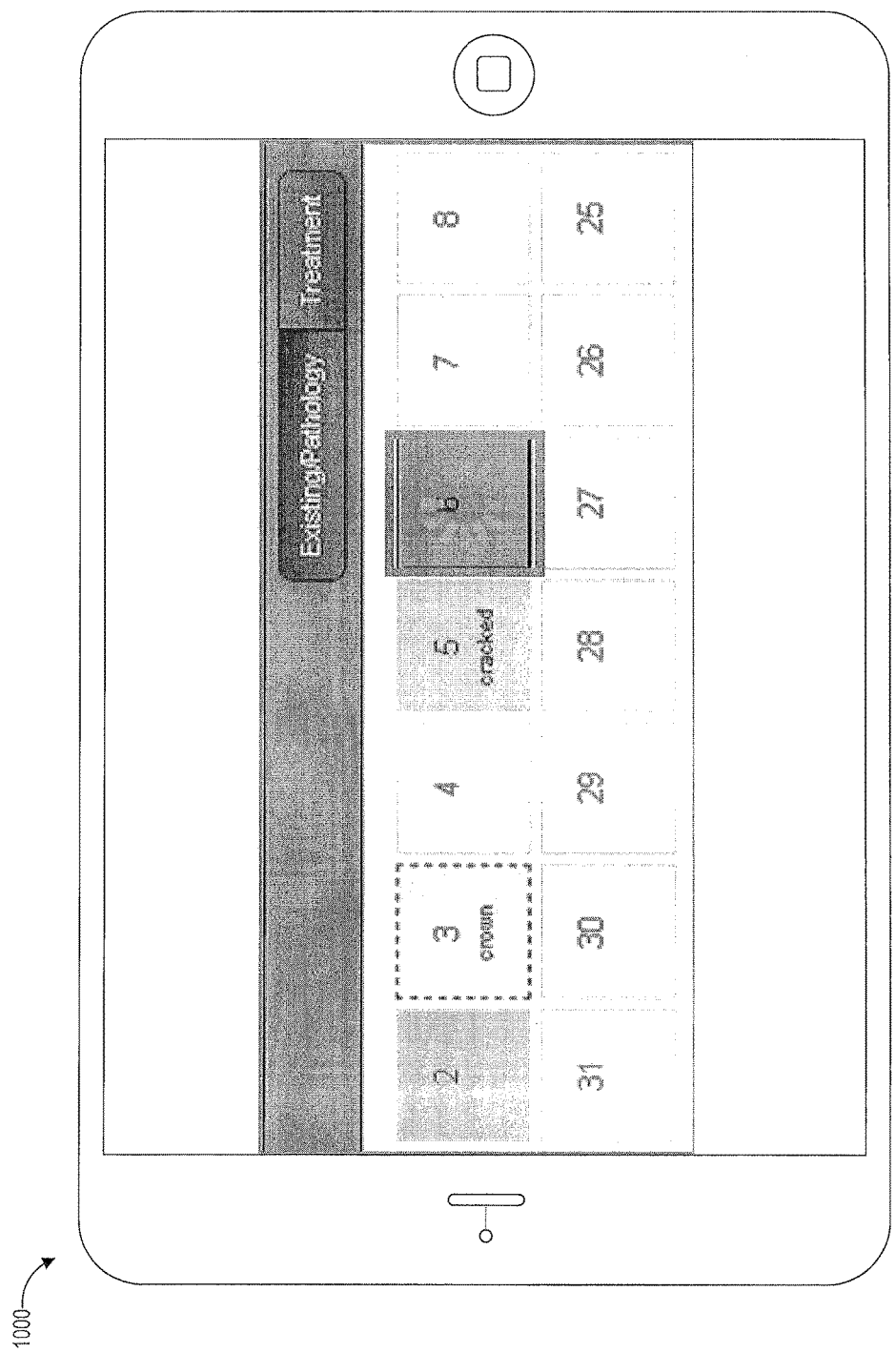
Figure 10K:
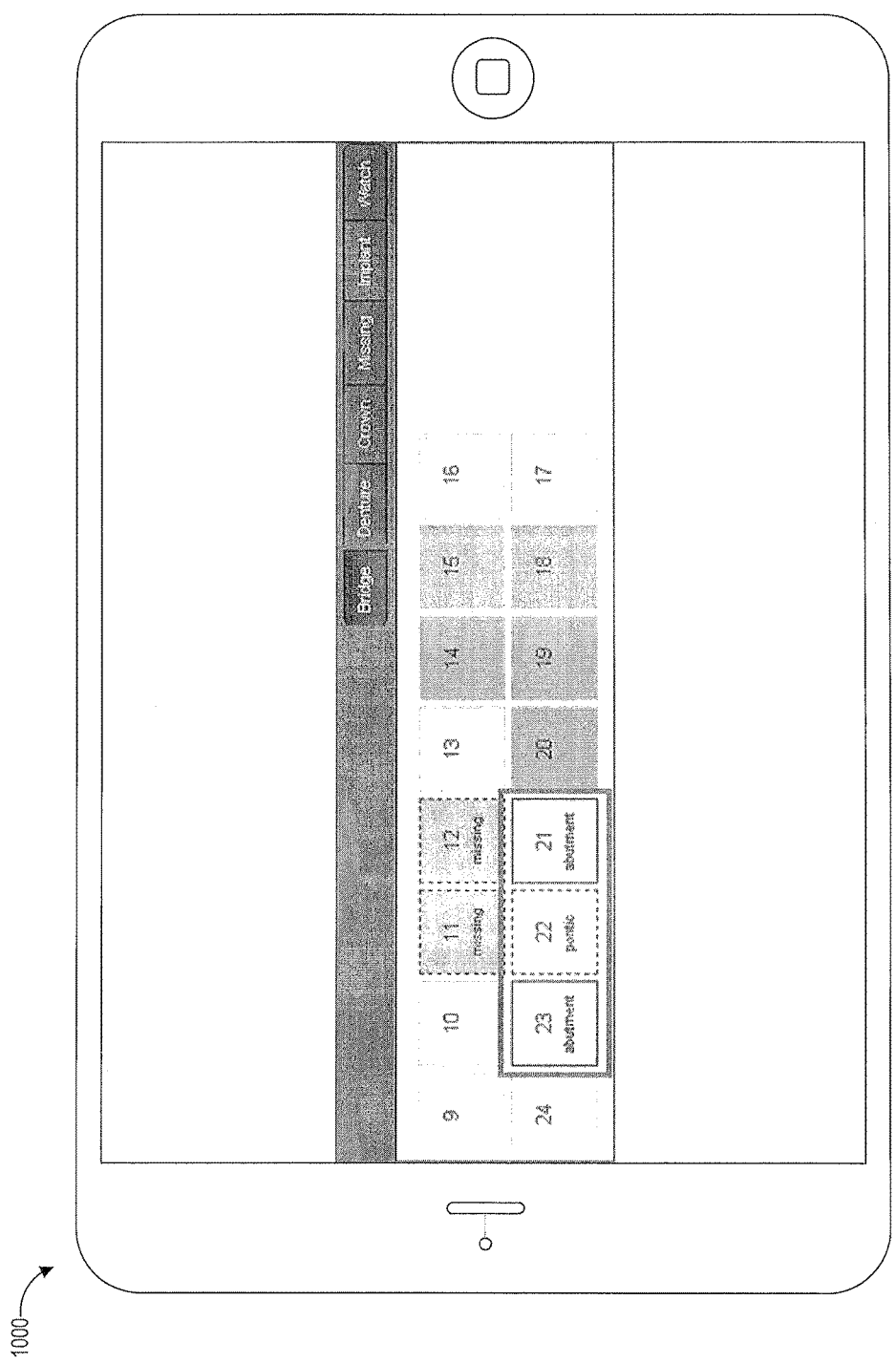
Figure 10L:
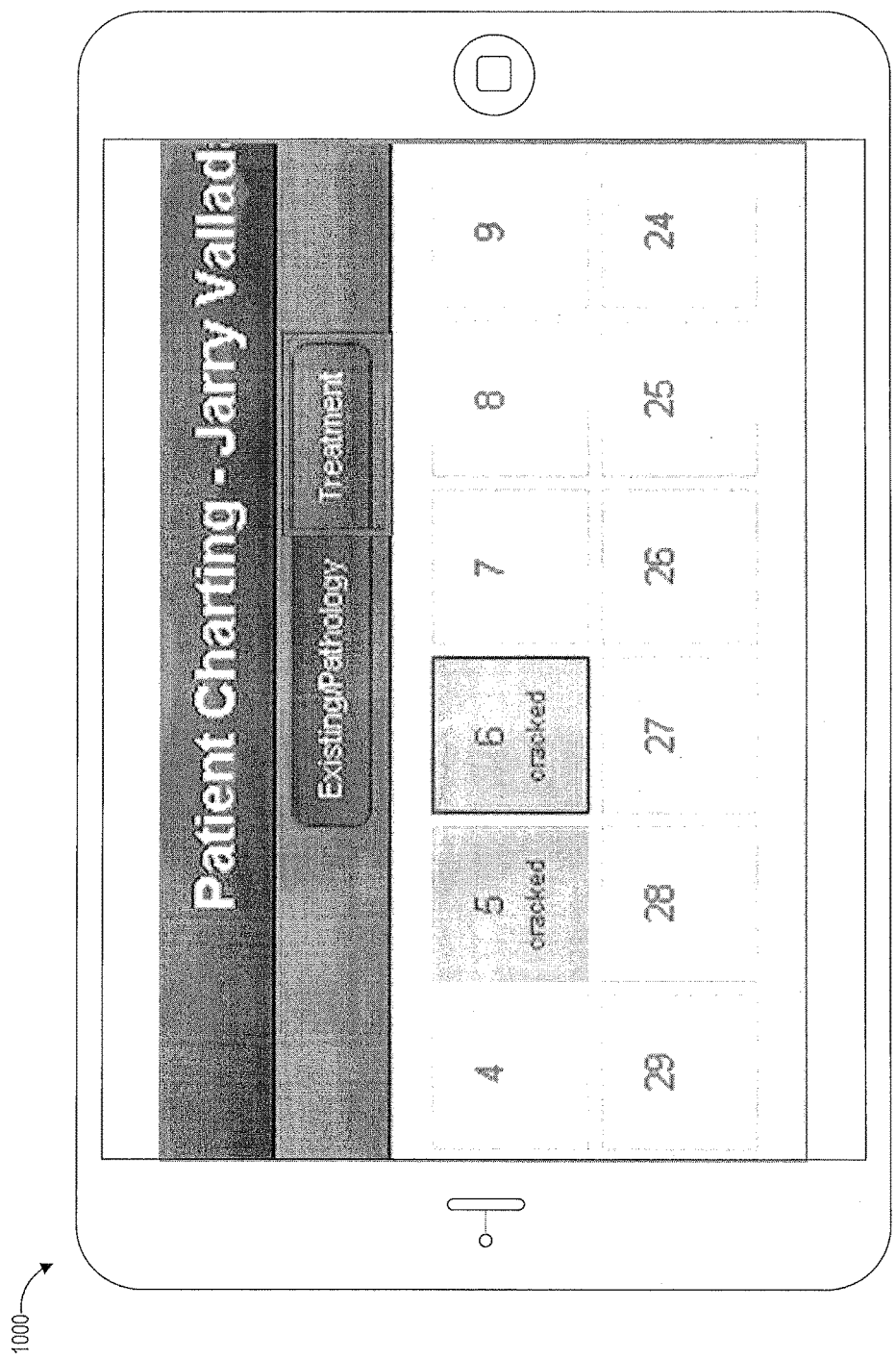
Figure 10M:
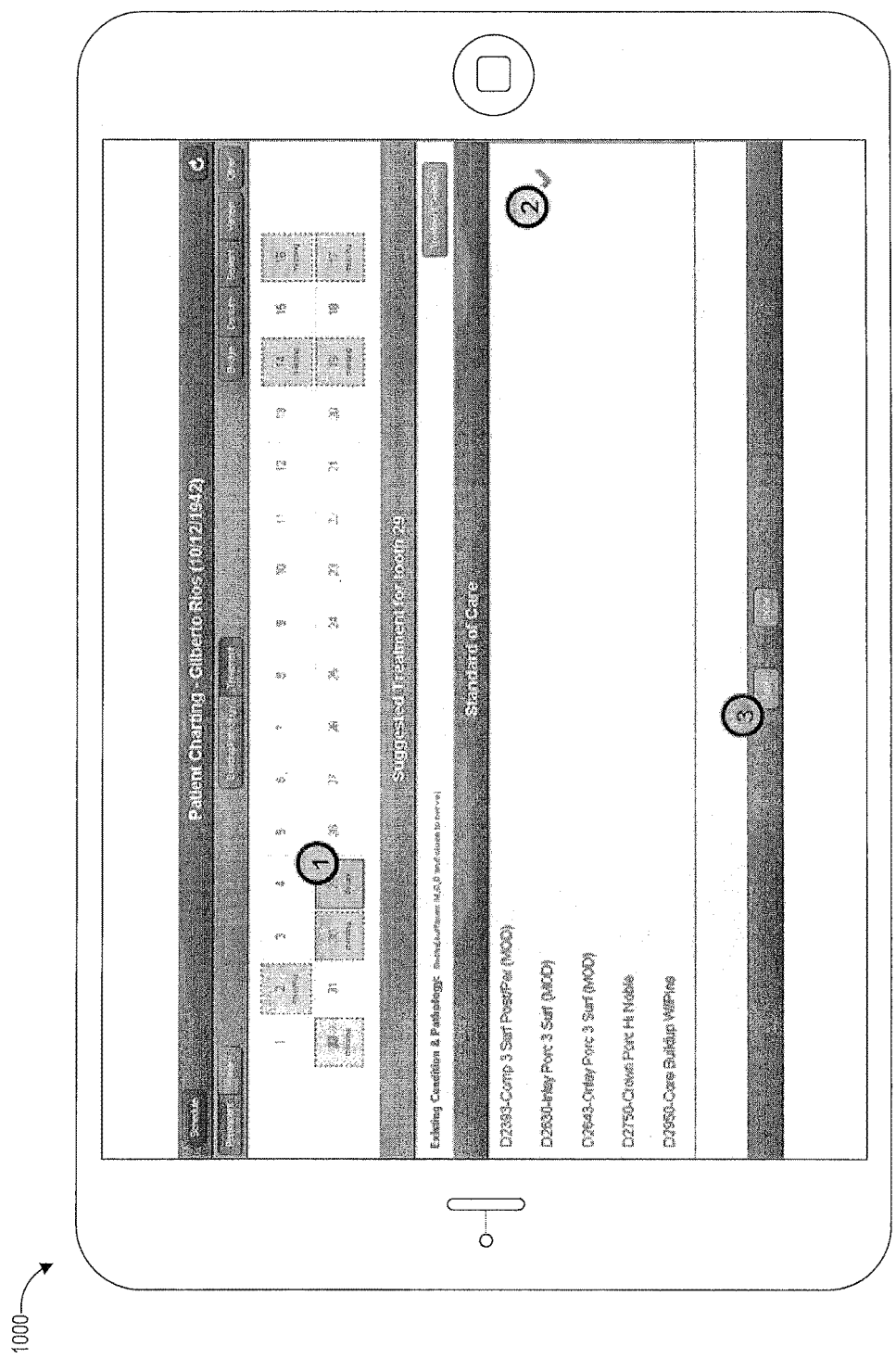
Figure 10N:
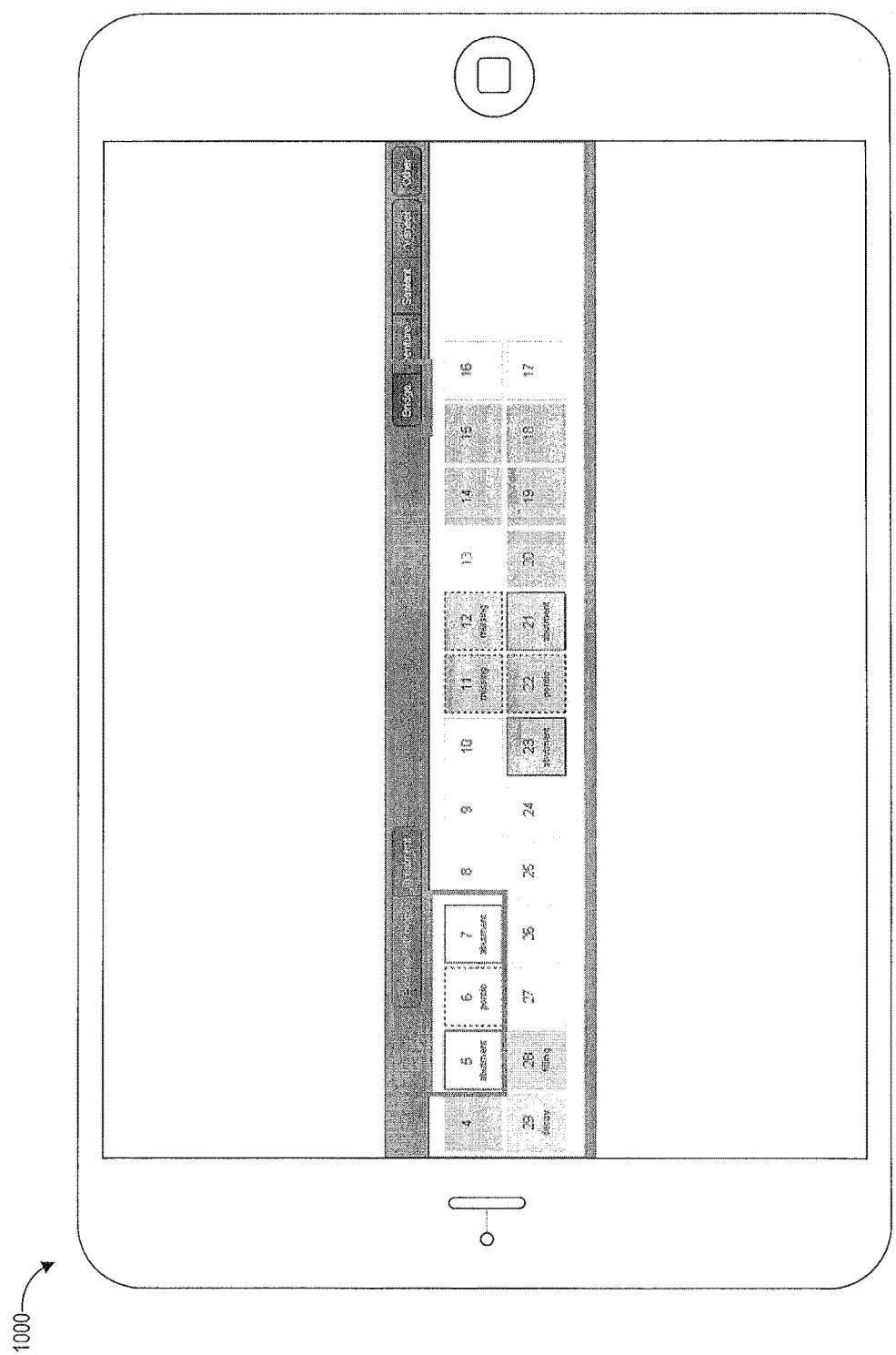
Figure 10O:
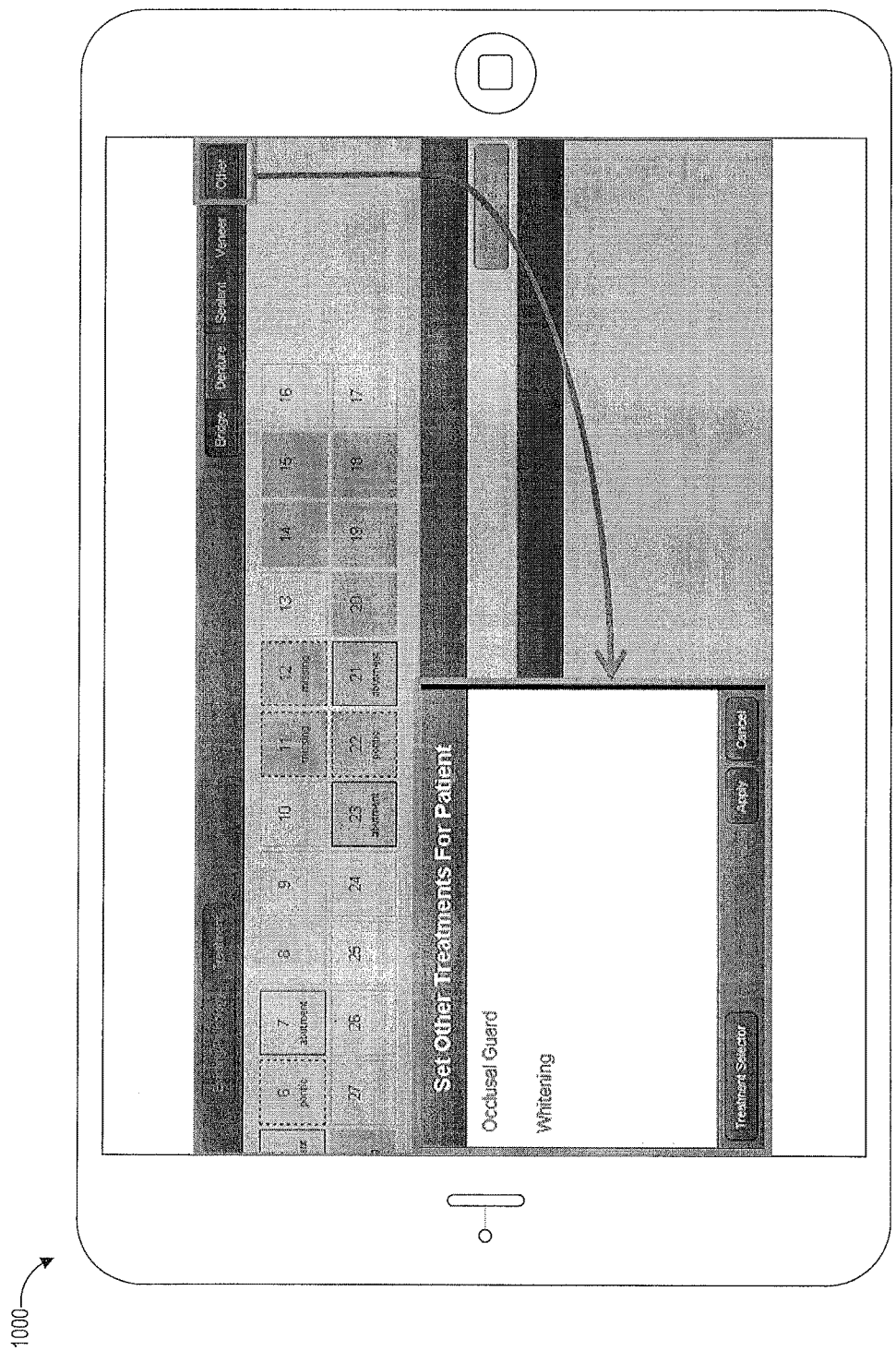
Figure 10P:
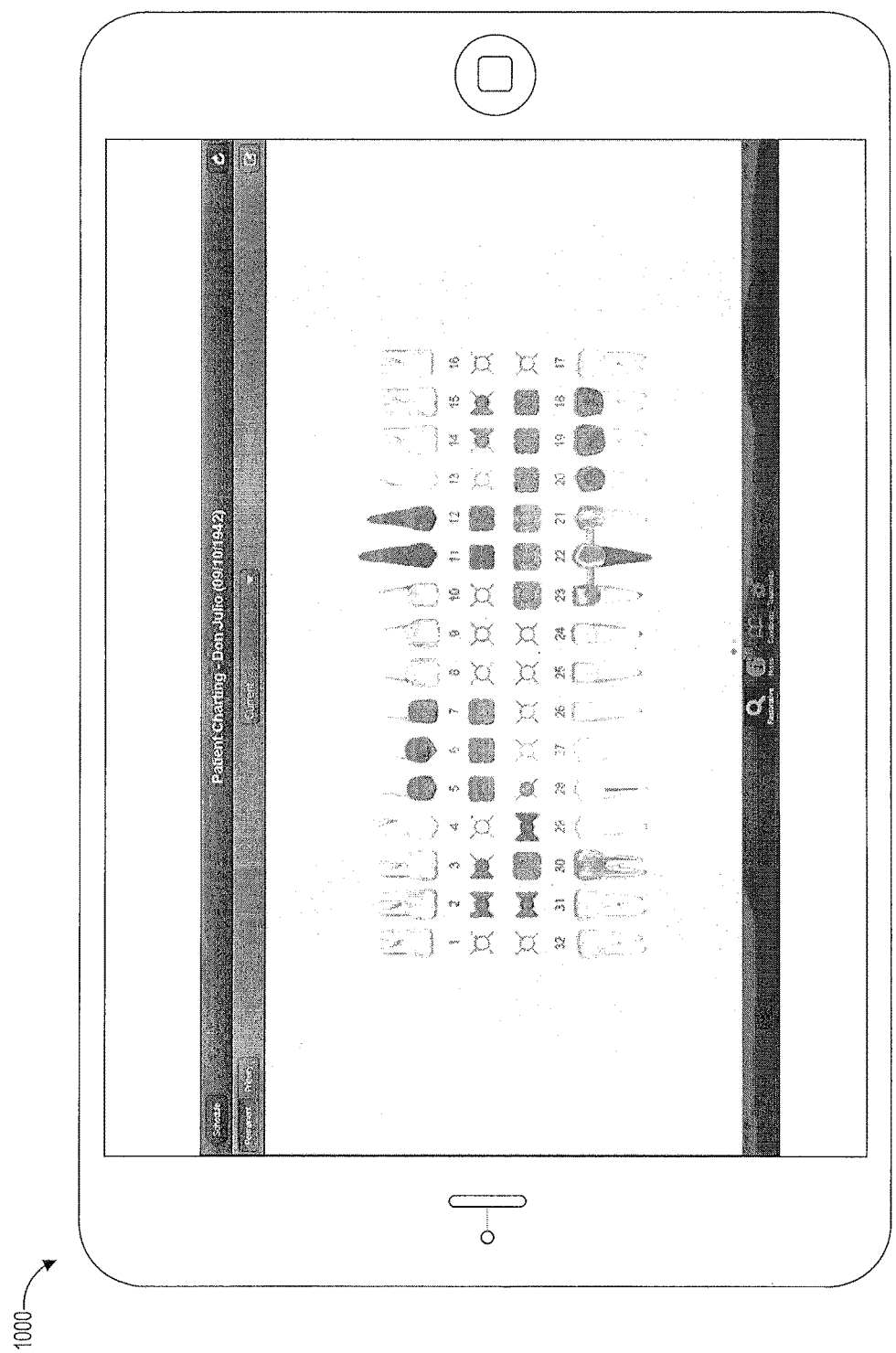
Figure 10Q:
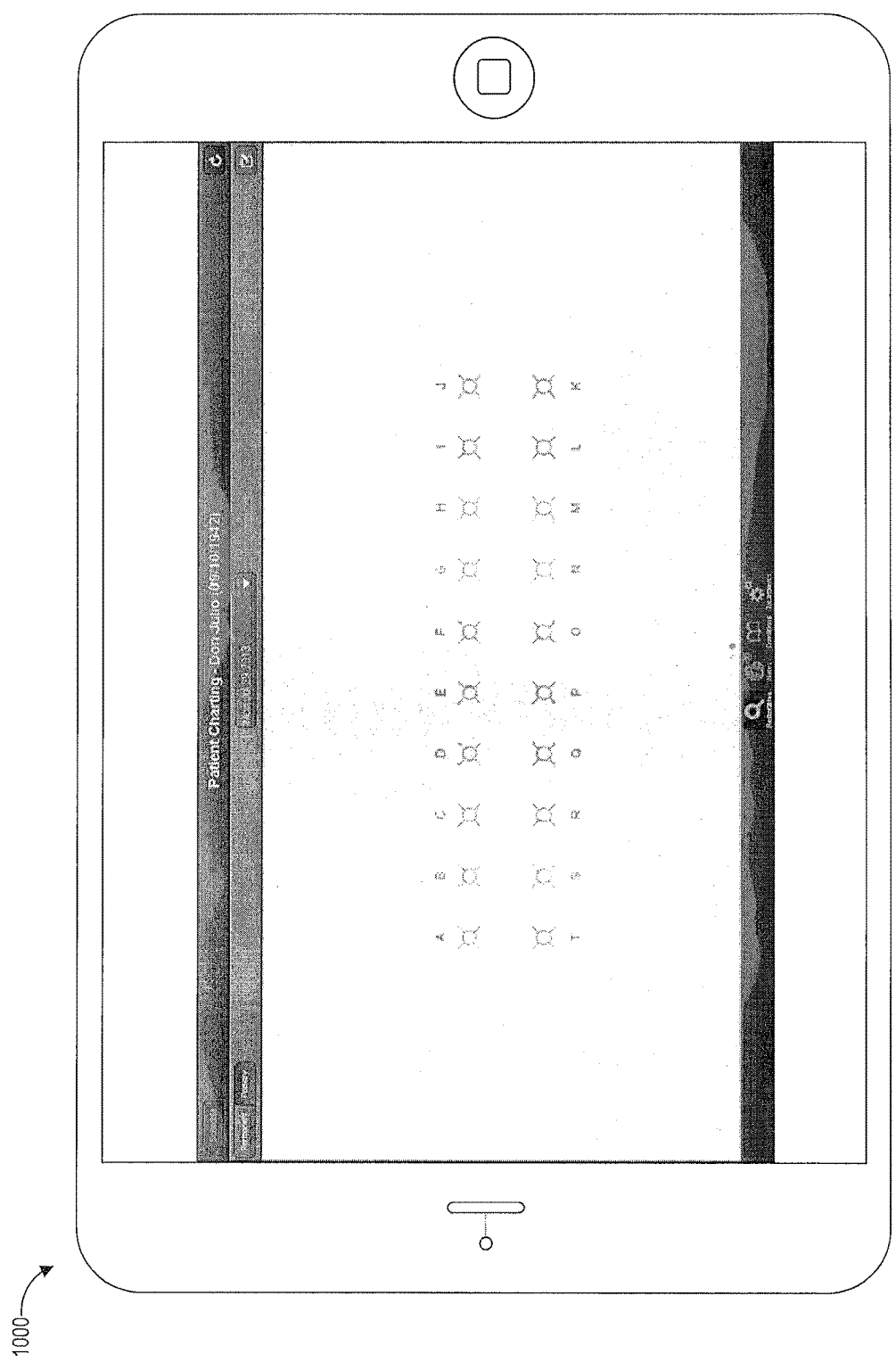
Figure 10R:
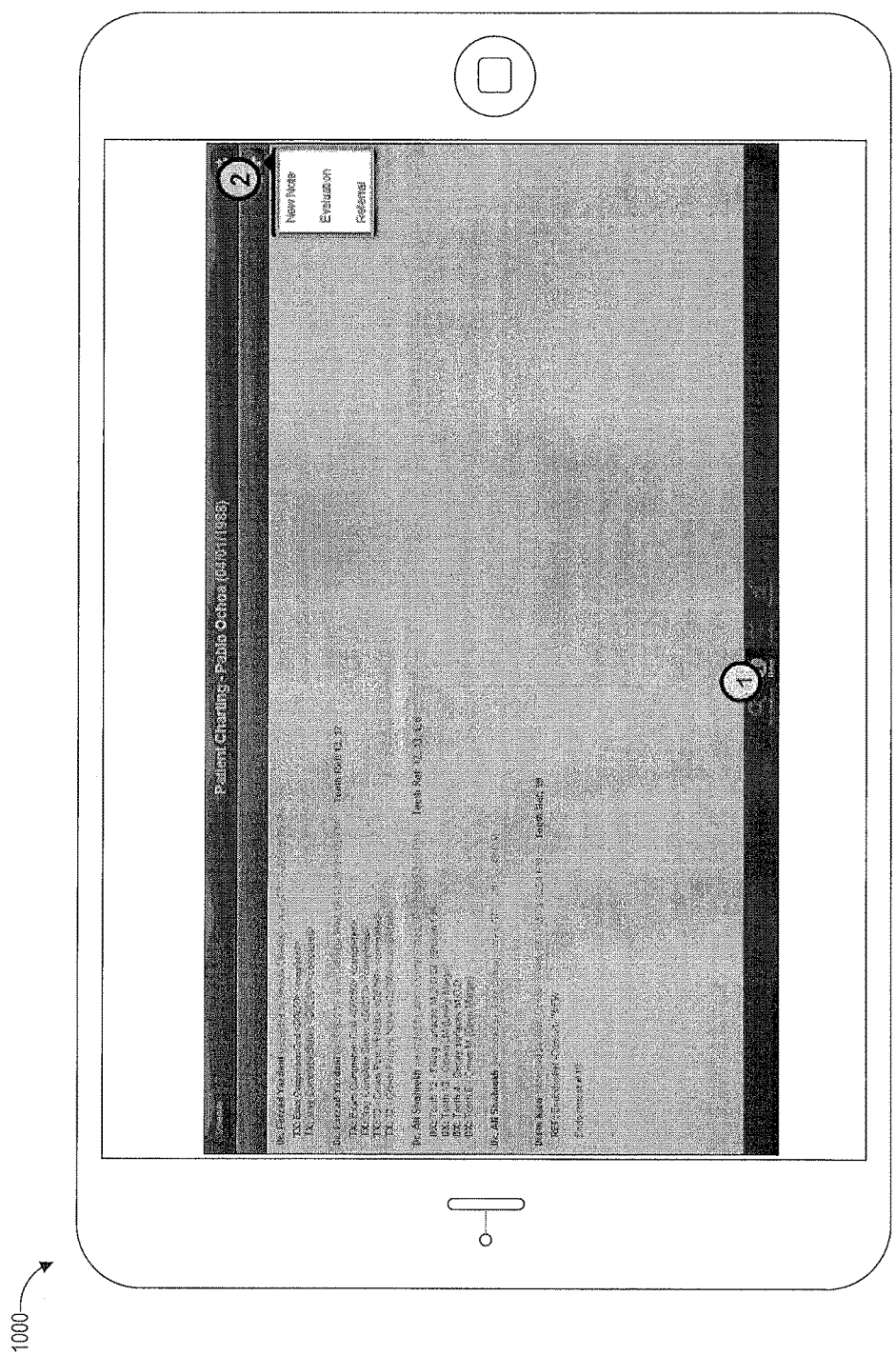
Figure 10S:
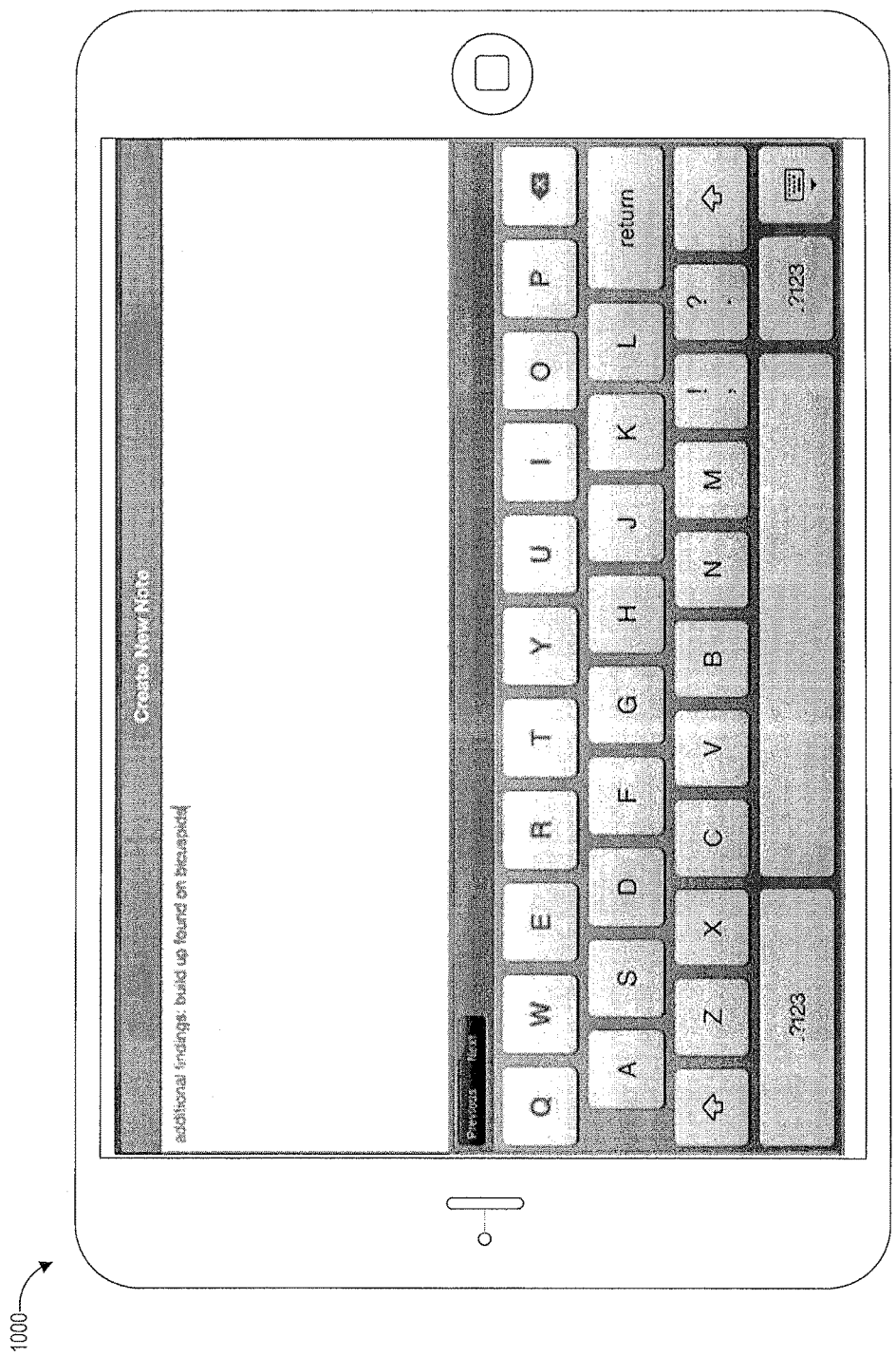
Figure 10T:
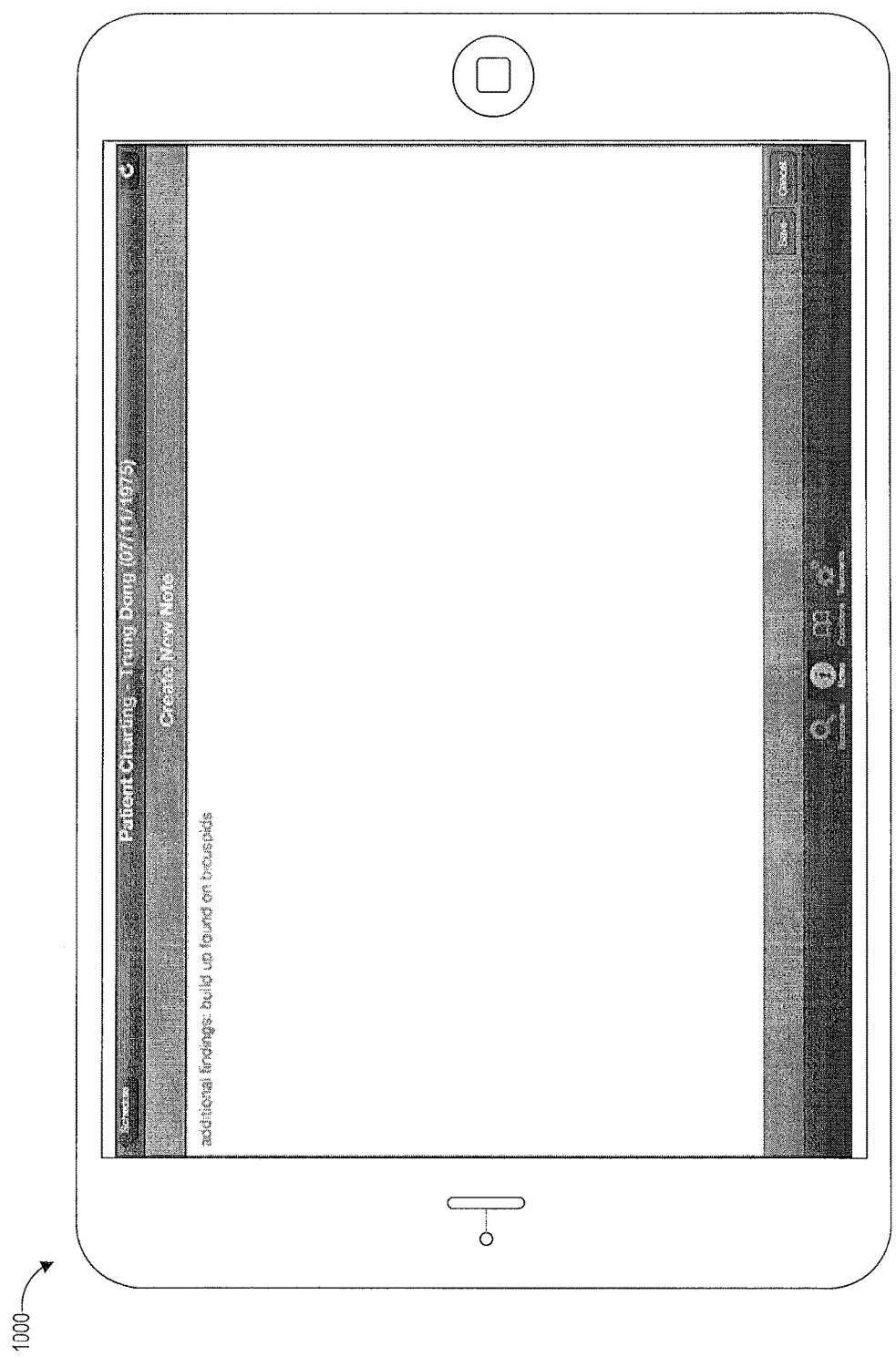
Figure 10U:
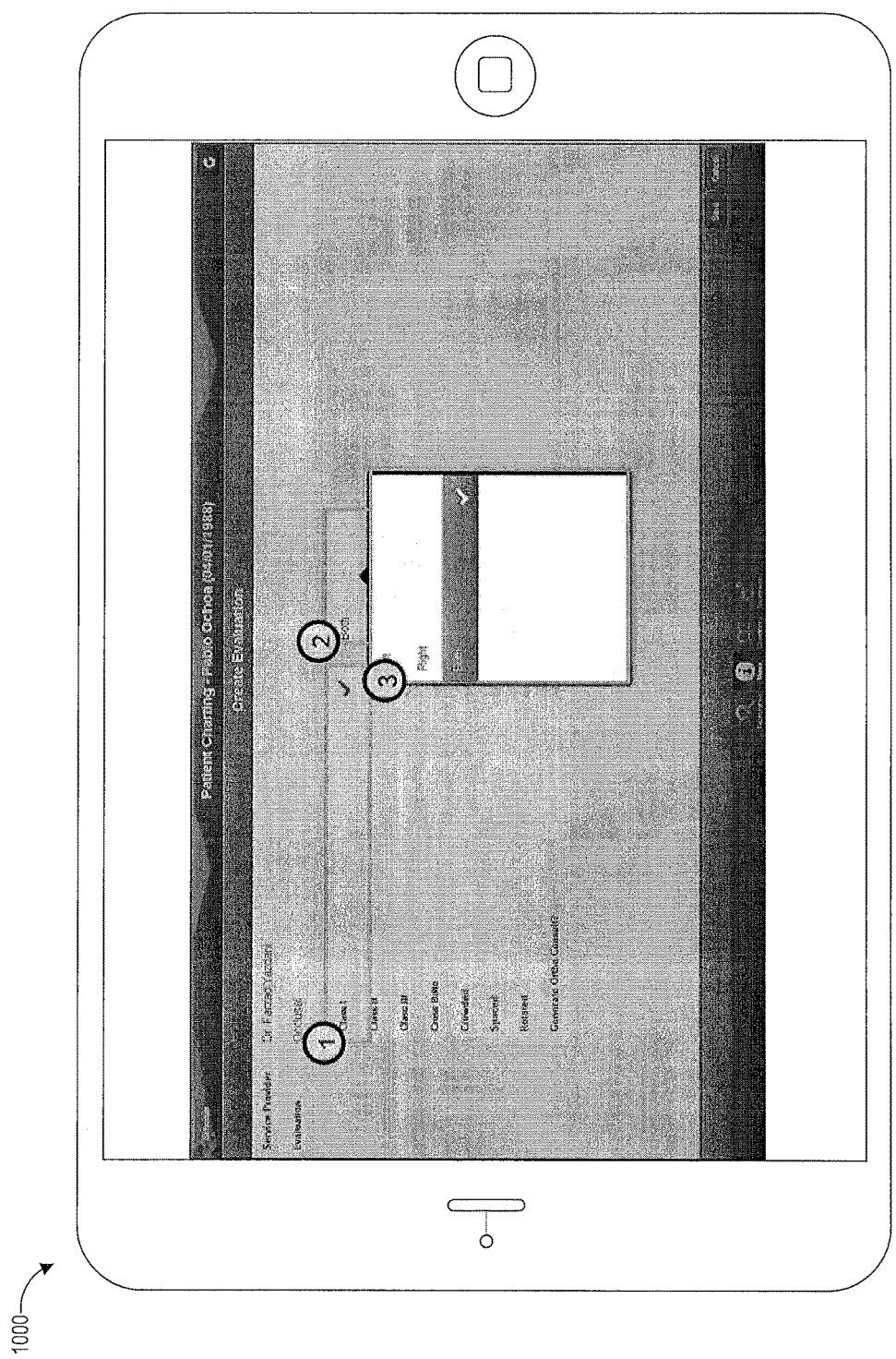
Figure 10V:
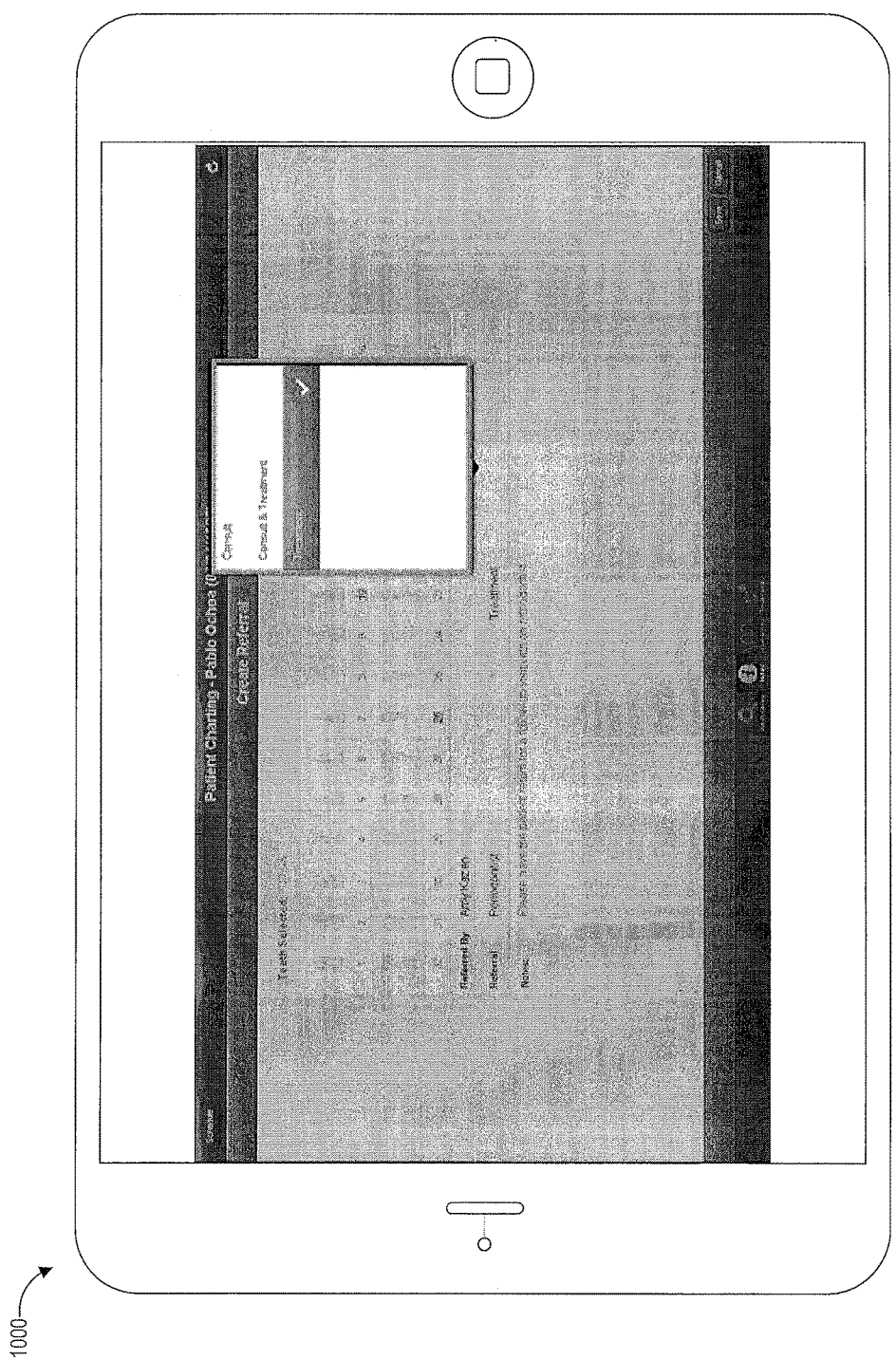

Turning to FIGS. 10A-10V, additional example functionalities provided by the dental office management service 130 (e.g., via user interface 1000) are described. In the example of FIG. 10A, scheduled patients are displayed. The office location is displayed at the top-right of the screen. The start screen defaults to the day's patients. The clinician may tap the left and right arrows or "Set Date" to go to another day's patients. In the user interface shown in FIG. 10A, the clinician may tap the patient's name to bring up the most recent restorative chart, as shown in FIG. 10B. If the first restorative chart is being created, a blank chart appears. When the clinician taps the pencil icon in FIG. 10B, a pop-up window shown in FIG. 10C is displayed. The clinician may tap "Yes" to create a restorative chart. When the clinician taps "Yes," a service provider selection pop-up window may be displayed, as shown in FIG. 10D. The clinician may select a service provider and tap "Create." Then, a screen appears for entering existing conditions, pathologies, and proposed treatments, as shown in FIG. 10E. The default restorative chart is for adults (permanent). For children, the clinician may tap "Primary," as shown in FIG. 10F, For example, the primary teeth are represented by letters, as shown in FIG. 10G. As discussed above, the clinician may tap a tooth, tap the existing condition and/or pathology, as shown in FIG. 10H, The clinician may tap "Apply" to save. In one example, after selecting "Filling," the clinician can long-press "Amalgam" to open a pop-up for selecting the type of filling, as shown in FIG. 10I. A spinner icon shown in FIG. 10J may be used to indicate that the existing condition and/or pathology is being applied.

To apply conditions to a group of teeth, the clinician may tap or otherwise select (for example) the "Bridge" button in the top-right corner of the screen, and then tap the group of teeth, and tap "Apply," as shown in FIG. 10K. (Tapping buttons is used herein as one example of selecting a user interface control. Other examples include mouse clicking, typing a keyboard shortcut, and the like.) To undo a selection, the clinician can tap the tooth to be unselected, re-tap the existing conditions and/or pathologies to "un-grey" them, and then tap "Apply." After completing existing conditions and/or pathologies, the clinician can tap the "Treatment" button at the top center of the screen to add treatments, as shown in FIG. 10L. To enter treatments, the clinician can tap a tooth, tap a suggested treatment, and tap "Apply," as shown in FIG. 10M. If the desired treatment is not displayed, the clinician can tap "Treatment Selector" to open the treatment selection window. The clinician can find and select the treatments and tap "Apply" to enter the selected treatment. In the top right corner of the screen, the clinician can tap one group option and then tap the teeth, as shown in FIG. 10N. For bridges, the clinician can double-tap a tooth for pontic.

Tapping "other" opens a list of additional treatments specific to the tooth selected. As shown in FIG. 10O, a menu for Occlusal Guard and Whitening treatments appears. The clinician may tap "Done" to return to the overall patient chart. In FIG. 10P, grey may indicate an existing condition, which could have been done at another dental company or before a predetermined time, red/pink may indicate pathological failure/issue that requires attention, green may indicate treatment proposed for the tooth, and blue may indicate treatment completed by the present dental company, or after a predetermined time.

The clinician may swipe left to see the primary teeth chart for minors, as shown in FIG. 10Q. The clinician may tap "Notes" at the bottom of the screen, and then tap the "+" button in the top-right corner and select one of the drop-down buttons to enter a new note, create an evaluation, or make a referral, as shown in FIG. 10R. In one example, a note about the order of treatment priority may be added for the treatment counselor. For example, such a note may explain what treatments are needed for the next visit, what are optional, and what are alternative treatments.

The clinician may tap "New Note" to enter a new note. When the clinician taps the white space, a keyboard appears, as shown in FIG. 10S. The clinician may enter the note, tap "return," and tap "save," as shown in FIG. 10T, to save the note and return to the home screen.

To make an evaluation, the clinician may tap "Notes," and then tap "+." When the menu appears, as shown in FIG. 10U, the clinician may tap "Evaluation," tap the drop-down arrow and checkmarks to open menus and select options. The clinician may tap "Save" to save the evaluation and return to the home screen.

To make a referral, the clinician may tap "Notes," and then tap "+." When the menu appears, the clinician may tap "Referral," tap the teeth to select them, tap the drop-down arrows to open menus and select options, Tap the notes section to display a keyboard and enter notes, as shown in FIG. 10V, and tap "Save" to save the referral and return to the home screen.

Figure 11A:
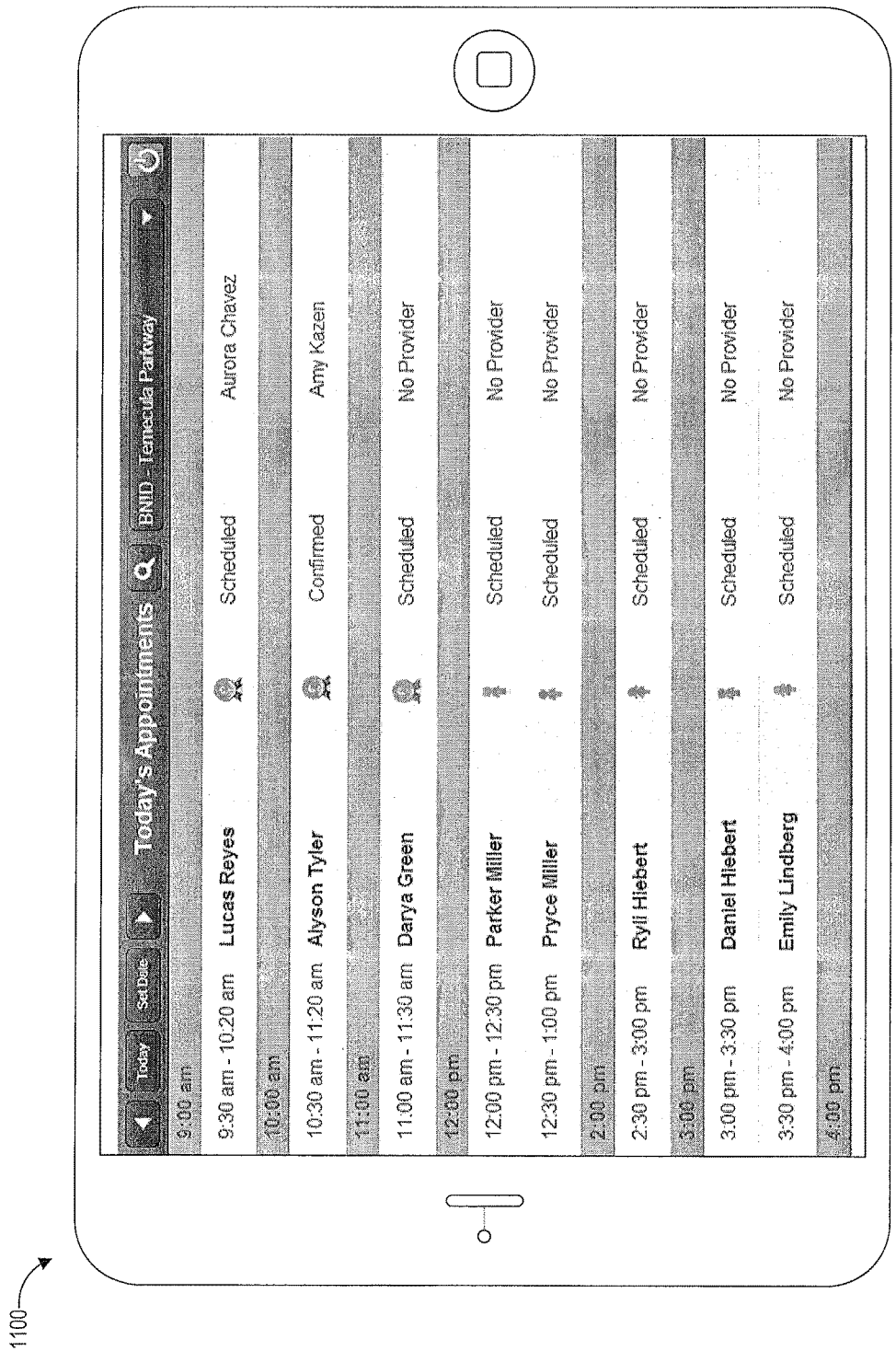
FIGS. 11A-11C depict example user interfaces for utilizing various functionalities provided by the dental office management service.
Figure 11B:
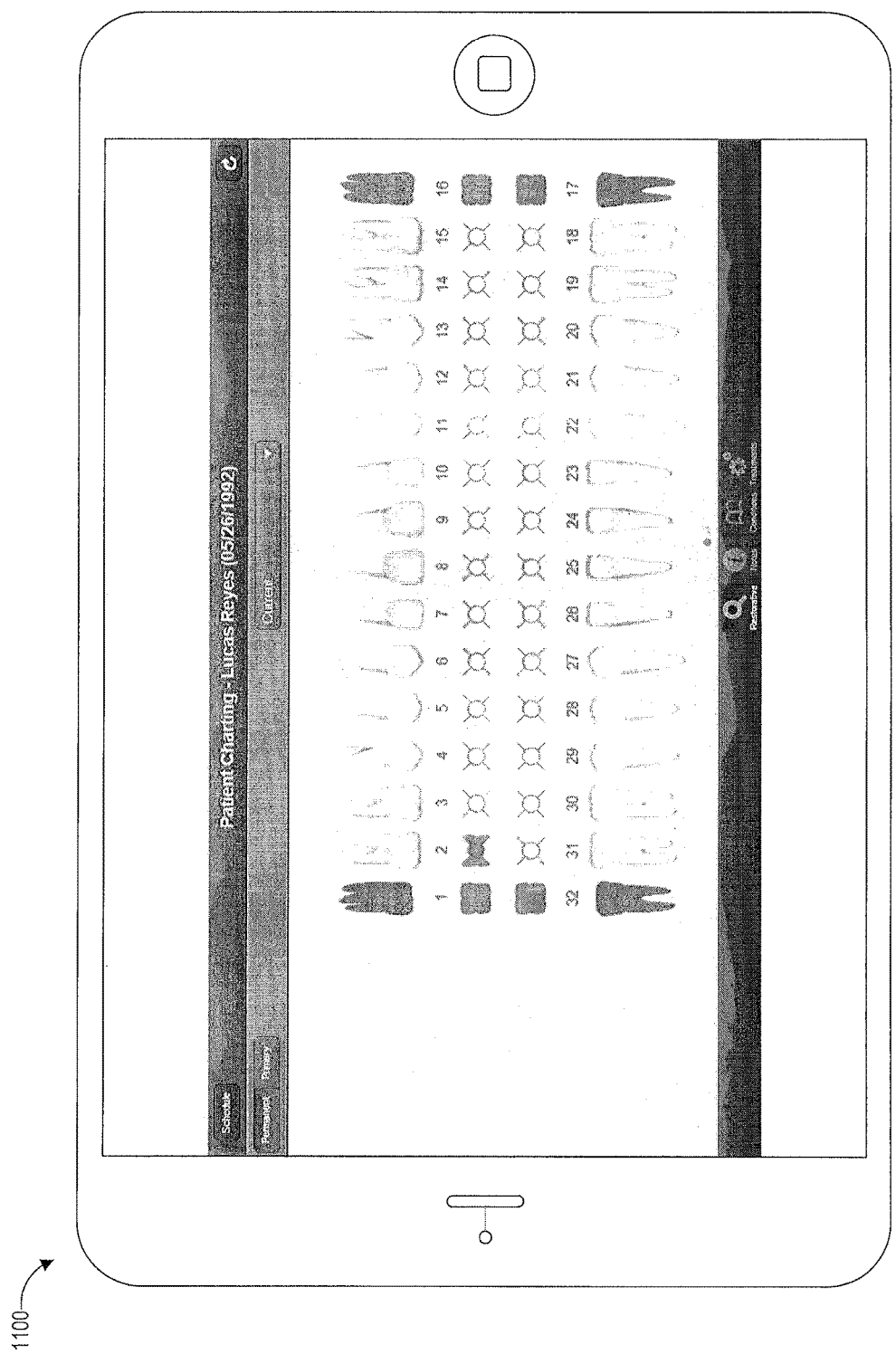
Figure 11C:
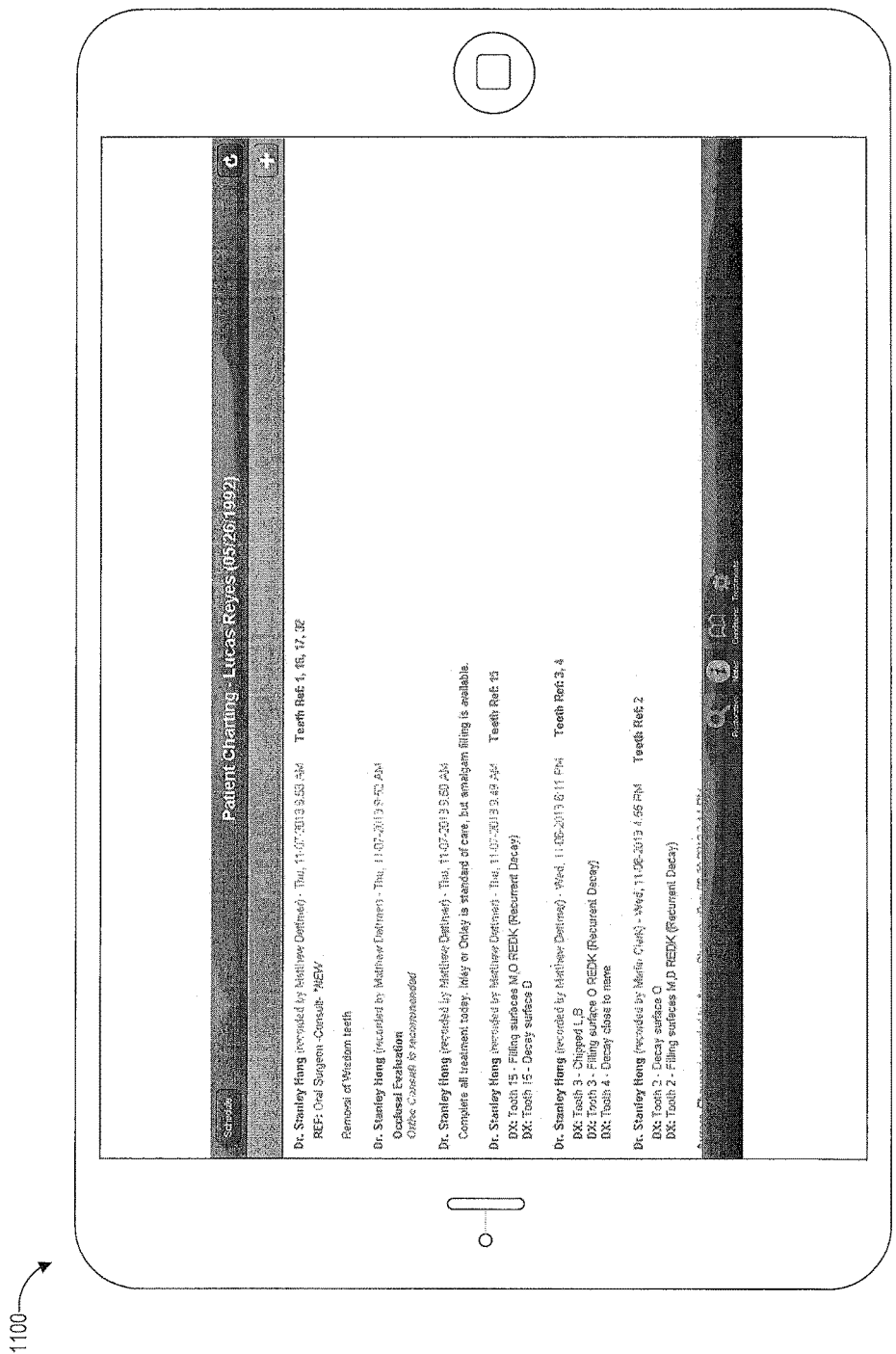

With reference to FIGS. 11A-11C, additional example functionalities provided by the dental office management service 130 (e.g., via user interface 1100) are described. For example, the patient's restorative chart is entered using a tablet by the dental assistant as the dentist completes the exam and reviews the x-rays. The initial screen shown in FIG. 11A allows the dental assistant to select the patient from the list of the day's scheduled patients. After selecting the patient, the assistant may start a new chart to enter the patients' existing conditions, pathologies, and treatments as directed by the dentist, as shown in FIG. 11B. After saving the treatment, the dentist may enter notes to direct the treatment counselor on how to group the treatments and present options to the patient, as shown in FIG. 11O. Some or all information may be transferred into the patient's file (e.g., stored in data repository 160) in the electronic computing system 110.

Figure 12A:
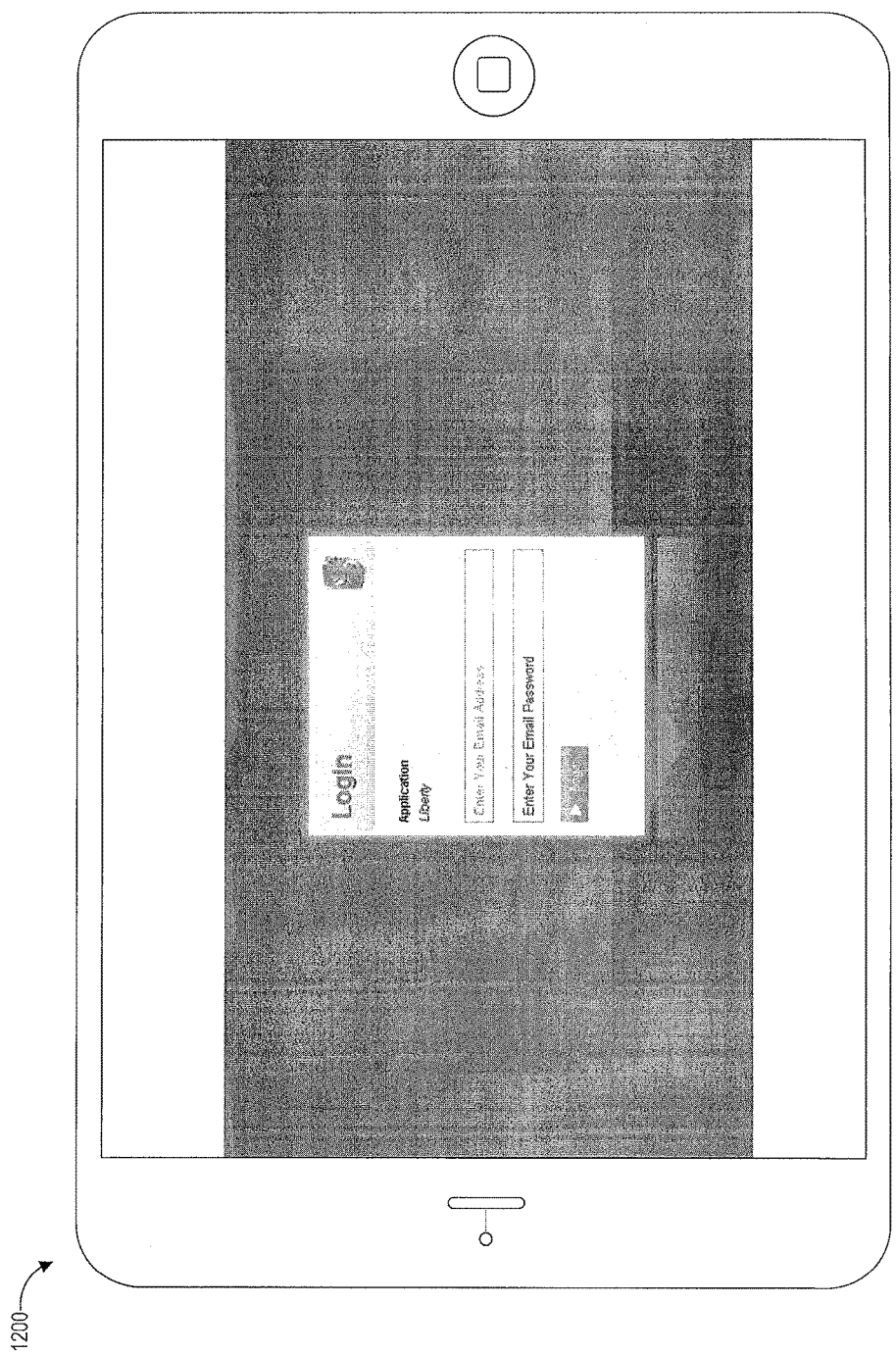
FIGS. 12A-12C depict example user interfaces for logging into the electronic computing system.
Figure 12B:
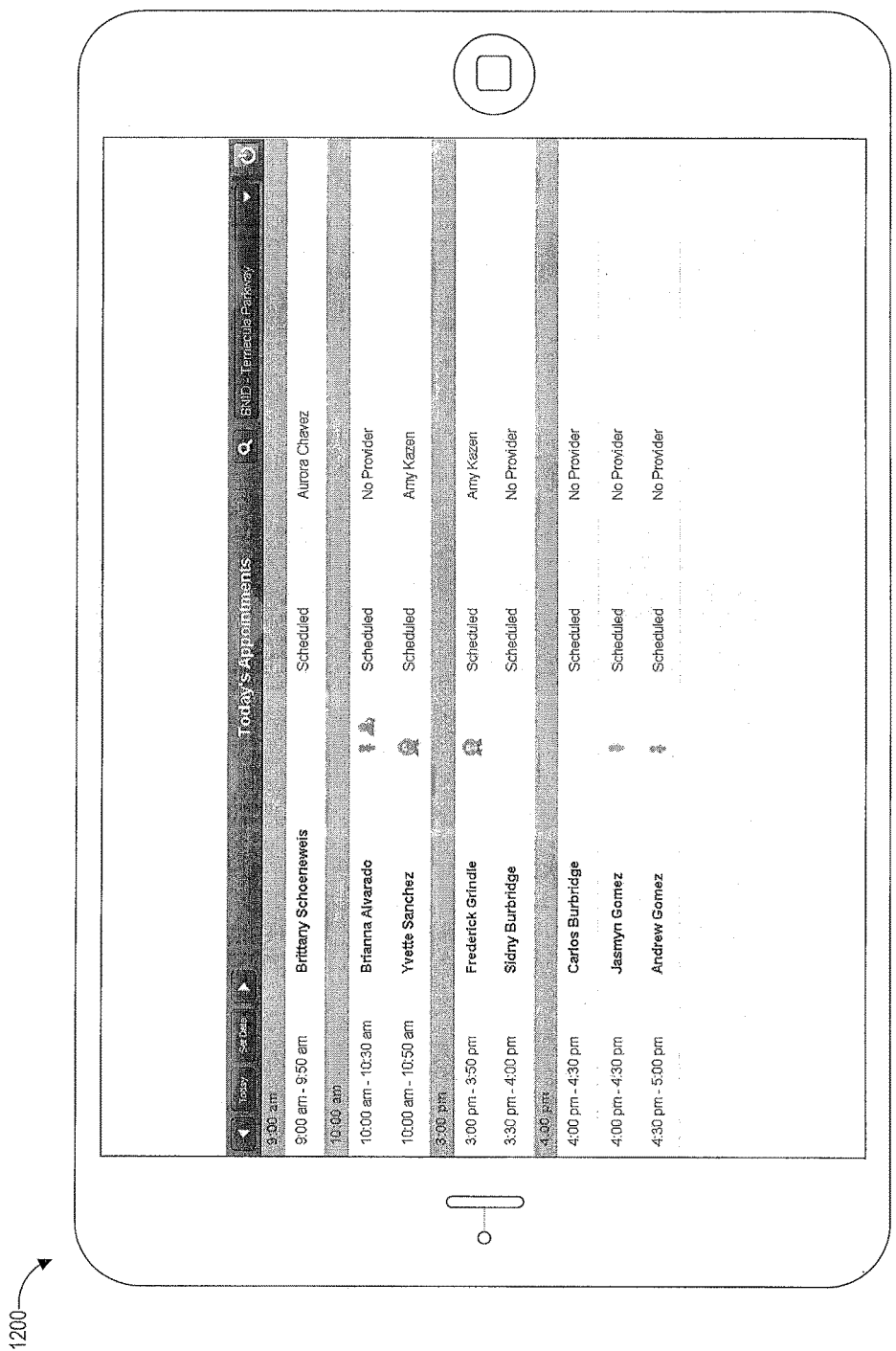
Figure 12C:
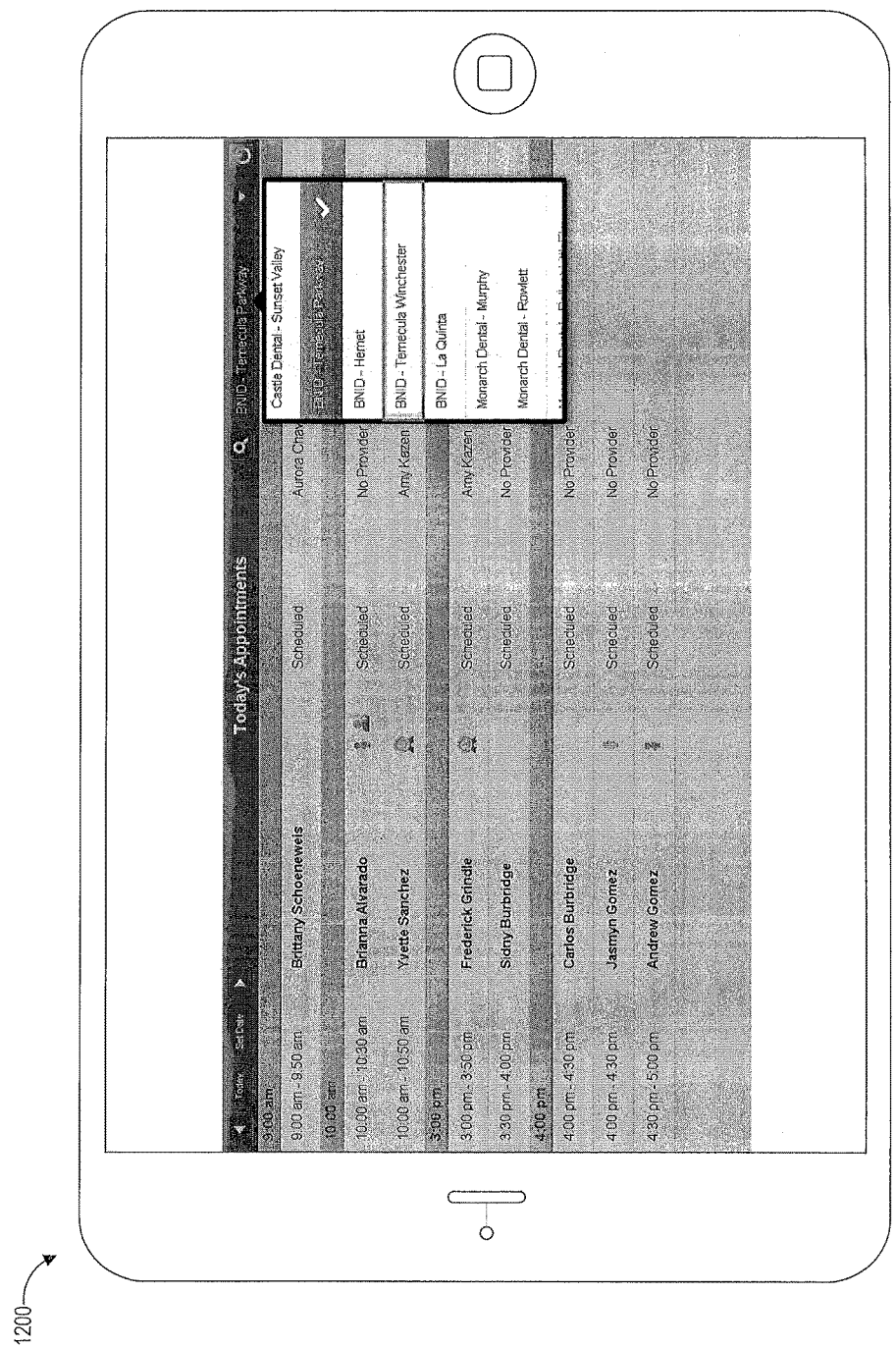

With reference to FIGS. 12A-12C, an example log-in process is described. On the tablet login screen shown in user interface 1200 of FIG. 12A, the clinician may enter his or her employee login credentials. After a successful login, the dental office management service 130 provides to the clinician a user interface for the home page shown in FIG.

12B. The home page may display a list of scheduled patients for the current day at the default office. In this example, the default office is Temecula Parkway. To switch offices, the clinician may tap the office name menu, swipe through the list to find the desired office, and then tap the office, as shown in FIG. 12C.

V. Additional Embodiments

Scalable Dental Office Management System:

In certain embodiments, a system and method is provided for scalable dental office management. The system can include hardware and/or software that enables dentists and dental office staff to manage patient data, appointment schedules, and the like. Advantageously, in certain embodiments, the system is highly scalable, allowing seamless operation across multiple dental offices, allowing for a provider to work in multiple offices seamlessly.

Some aspects of embodiments of the system that can promote scalability include a platform-agnostic design that allows the system to be implemented in any platform or operating system (including Microsoft Windows™, Unix environments, Linux, AIX, and the like). In addition, the use of web-based technologies such as Java, HTML5, CSS, and the like can allow the system to be hardware-independent and therefore able to scale with any hardware installation at a particular dentist's office. The system can also be implemented in a cloud platform to further increase scalability. For instance, the system can be implemented in an Infrastructure-as-a-Service, Platform-as-a-Service, or Software-as-a-Service environment such as Amazon AWS™, Microsoft Azure™, or the like. These platforms have massive compute capacity that can scale rapidly in response to rising demand. More generally, the system can be implemented in one or more servers and may be accessed by one or more client computers or mobile devices at dental office locations or in mobile situations. The system can also implement a web services architecture to enable seamless communication between components.

Scalability of the system is also promoted in certain embodiments by having a high capacity for transaction codes (e.g., 1000s or even up to a million or more transaction codes available). In addition, the system can be enterprise-based, providing access to a clinician with a single access code or login credentials in any dental office that implements the system. Further, the system can include a relational (or even NoSQL) database backend implemented, for example, using Oracle™, Postgres™ SQL Server™, or the like, for storing patient data and image data instead of using flat files, which are commonly used in the dental software industry. The system can also distribute data to a downstream server(s) at the dental office to allow for faster database access. Typically, dental offices have used flat files because a single dental office may not have need of an expensive database to store patient data. However, flat files become unworkable for managing dental records and data across multiple dental offices. In addition, the system can be scalable in part because the system can be implemented using a tiered application architecture that separates database functionality, business logic, and presentation or user interface functionality (among possibly others). This architecture can allow for extensibility and rapid maintenance and development.

Scheduling and Unified View:

Some example features of the system can include functionality for scheduling of dentists/doctors among multiple offices, which may be facilitated by doctors being assigned the single unique identifier described above. One of the features of the system in certain embodiments provides a set of functionality specifically for scheduling in a call center environment where the application interacts with the phone system to determine the location of the caller and the closest Dental Office, Provider or Specialist. Dentists often work among multiple offices but currently have to log in to existing software at separate offices using multiple identifiers. The resulting views and data presented to dentists in different offices are therefore siloed and fragmented, as a dentist can typically only see his or her patients and related data associated with the office the dentist is logged into. In contrast, the system described herein can present dentists with a unified view at any office dentists visit, enabling the dentists to view patients and data from multiple office locations more easily and efficiently. Office staff, dental assistants, and hygienists can benefit from the same functionality.

Charts and Touch Functionality:

In addition to the embodiments described above, the system can also present useful charts and information to dentists (and dental assistants, hygienists, and the like; collectively, "clinicians"), such as interactive periodontal charts, interactive restorative charts, and the like. For example, the interactive periodontal charts can include a voice input feature that allows clinicians to use voice commands to input data in a patient's chart. Moreover, the system can store patient's charts over time to allow a clinician to compare a patient's current chart with a previous chart to enable determination of a patient's progress over time. Further, these charts can include functionality for clinicians to create their own templates for describing patient conditions in a notes section of a patient's chart. In one embodiment, the system outputs a notes user interface that enables the clinician to drag and drop a standard template description of a patient condition into the notes section of the patient's chart supplement the standard note with additional treatment and/or diagnosis information The notes user interface can also include a user interface control that enables clinicians to select American Dental Association (ADA) codes for inclusion in a patient's chart.

Centralized Storage of Data:

The system can also provide highly scalable and portable centralized storage for image data, including x-rays, as well as patient data. In an embodiment, the system implements a messaging architecture that enables x-rays or other images taken at a dental office to be uploaded to a central repository, which may be implemented in cloud storage (such as Amazon's S3™ storage solution) or the like. The system can be location aware and can store x-rays in a tiered environment allowing the local office to retrieve x-rays locally. Subsequently, a clinician in any office can access x-rays or image data that were taken in any other office that uses the same system. Likewise, a clinician can use a mobile device either at the office or away from the office to view image data, patient records, and the like.

Intelligent Scheduling:

The system can also include intelligent patient scheduling features. For instance, in one embodiment, the system provides an intelligent queuing feature that triages incoming calls from new patients. The system may include, for example, an interactive voice response (IVR) system that determines patients' needs, prioritizes patients based on emergency and non-emergency needs, and identifies dentists with availability to see patients with emergencies as soon as possible. Further, the system can utilize Geo Coding to automatically identify dental offices that are close to a patient's location and recommend such dental offices to the patient, who may have been unaware of the close proximity of such offices. Similar functionality can also be provided without using an IVR, for instance, by automatically recommending a dental office and appointment time slot for an available clinician after a receptionist enters parameters about the new patient in the system (such as type of dental problem experienced, location, demographic info, and the like).

SMS or Text:

The system may also provide SMS or text functionality in certain embodiments that sends texts to patients confirming appointments and that allows patients to send return texts to confirm, reschedule, or cancel appointments.

VI. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, module, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, and the like, may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others.

What is claimed is:

1. A method for providing dental treatment recommendations, the method comprising:
   outputting a dental user interface to a user on a display, the dental user interface comprising first user interface controls selectable to specify tooth pathologies of a patient under examination by a clinician, each of the first user interface controls corresponding to a particular one of the tooth pathologies;
   receiving a user selection of one or more of the first user interface controls indicating a specified one of the tooth pathologies for a tooth of the patient and at least one of a location of the tooth or a surface of the tooth;
   programmatically causing a hardware processor to identify a subset of recommended dental treatments from a plurality of dental treatments available for the specified tooth pathology based at least in part on the location of the tooth or the surface of the tooth specified by the received user selection;
   outputting the subset of recommended dental treatments on the display as a list of the subset of recommended dental treatments, the list comprising second user interface controls selectable by the user to specify one of the subset of recommended dental treatments that matches an actual treatment recommended by the clinician, each of the second user interface controls corresponding to one of the subset of recommended dental treatments;
   determining whether one of the second user interface controls is selected by the user to specify a corresponding one of the subset of recommended dental treatments;
   in response to determining that one of the second user interface controls is selected by the user, adding the selected recommended dental treatment to a list of selected dental treatments to be performed on the patient;
   performing the selected recommended dental treatment on the tooth of the patient;
   outputting the list of selected dental treatments on the display, the list comprising third user interface controls selectable by the user to specify one of the selected dental treatments that has been completed, each of the third user interface controls corresponding to one of the selected dental treatments;
   determining whether one of the third user interface controls that corresponds to the selected recommended dental treatment performed on the tooth of the patient is selected by the user to specify that the selected recommended dental treatment has been completed; and
   in response to determining that the third user interface control that corresponds to the selected recommended dental treatment performed on the tooth of the patient is selected by the user, outputting an electronic treatment template corresponding to the selected recommended dental treatment on the display for editing by the user, wherein the electronic treatment template includes one or more default values based on the selected one of the second user interface controls, the one or more default values editable by the user to specify parameters actually used to complete the selected recommended dental treatment.

2. The method of claim 1, further comprising receiving custom notes from the user in the electronic treatment template and storing the custom notes and electronic treatment template in a record of the patient.

3. The method of claim 2, further comprising storing, in the record of the patient, an associated American Dental Association (ADA) code along with the selected recommended treatment.

4. The method of claim 2, wherein said receiving the custom notes further comprises receiving user input that modifies the one or more default values.

5. The method of claim 1, further comprising outputting a chart including a plurality of icons corresponding to teeth of the patient, wherein one or more of the plurality of icons indicate a current status of a corresponding one of the teeth of the patient.

6. The method of claim 1, further comprising:
   receiving a user request to output a list of dental treatments available for the specified tooth pathology;
   outputting the list of dental treatments available for the specified tooth pathology, the list including at least one dental treatment that is not in the list of the subset of recommended dental treatments;
   determining whether an alternative dental treatment is selected by the user from the list of dental treatments; and
   in response to determining that an alternative dental treatment is selected by the user, associating the selected alternative dental treatment with the specified tooth pathology for future recommendation in a subsequent listing of available dental treatments.

7. The method of claim 1, further comprising:
   determining that another one of the third user interface controls is selected by the user to specify another corresponding one of the selected dental treatments; and
   in response to determining that said another one of the third user interface controls is selected by the user, outputting another electronic treatment template corresponding to said another corresponding one of the selected dental treatments at a location on the display that is adjacent to a location of the electronic treatment template corresponding to the selected dental treatment on the display.

8. The method of claim 1, further comprising refraining from outputting one or more electronic treatment templates corresponding to a subset of the selected dental treatments on the display based on a nonselection of one or more of the third user interface controls corresponding to the subset of selected dental treatments.

9. The method of claim 1, wherein the dental user interface comprises a first set of user interface controls selectable to specify tooth pathologies of the patient and a second set of user interface controls selectable to specify pre-existing dental treatments of the patient.

10. The method of claim 9, wherein the first set of user interface controls and the second set of user interface controls are, when outputted on the display, displayed on the same screen of the display.

11. The method of claim 10, wherein the dental user interface comprises a third set of user interface controls selectable to specify a tooth of the patient for which tooth pathologies and pre-existing dental treatments are to be specified by the first set of user interface controls and the second set of user interface controls, respectively.

12. The method of claim 1, wherein the dental user interface comprises fourth user interface controls selectable to specify a tooth of the patient for which tooth pathologies and pre-existing dental treatments are to be specified.

13. The method of claim 12, further comprising:
subsequent to determining that one of the second user interface controls is selected by the user for the tooth of the patient, receiving another user selection of one of the third set of user interface controls to specify another tooth of the patient; and
in response to receiving said another user selection, outputting the first user interface controls selectable to specify tooth pathologies for said another tooth of the patient.

14. The method of claim 13, wherein the outputted first user interface controls selectable to specify tooth pathologies for said another tooth do not reflect any prior selection made by the user with respect to any other tooth of the patient.

15. The method of claim 1, wherein the dental user interface comprises one or more selection indicator elements for indicating, for a given tooth of the patient, whether a recommended dental treatment has been selected by the user.

16. The method of claim 1, wherein the dental user interface comprises one or more status indicator elements for indicating, for a given tooth of the patient, a current status of the tooth.

17. The method of claim 1, wherein the subset of recommended dental treatments outputted on the display does not include at least some dental treatments included in the plurality of dental treatments that are accessible via an additional user interface control outputted on the same screen of the display as the second user interface controls.

18. The method of claim 17, further comprising:
receiving a user selection of the additional user interface control; and
outputting a list of categories of available treatments on the display.

19. The method of claim 18, further comprising:
receiving a user selection of one of the categories from the list of categories of available treatments; and
outputting a list of selectable treatments on the display.

20. The method of claim 18, further comprising:
receiving a user selection of one of the categories from the list of categories of available treatments; and
outputting a list of sub-categories of selectable treatments on the display.

* * * * *